US008008021B2

(12) United States Patent
Jin

(10) Patent No.: US 8,008,021 B2
(45) Date of Patent: Aug. 30, 2011

(54) N-TERMINAL TRUNCATION OF CARDIAC TROPONIN SUBUNITS AND THEIR ROLES IN CARDIOVASCULAR DISEASE

(75) Inventor: Jian-Ping Jin, Northbrook, IL (US)

(73) Assignee: Evanston Northwestern Healthcare, Evanston, IL (US)

( * ) Notice: Subject to any disclaimer, the term of this patent is extended or adjusted under 35 U.S.C. 154(b) by 738 days.

(21) Appl. No.: 11/828,259

(22) Filed: Jul. 25, 2007

(65) Prior Publication Data

US 2008/0032929 A1 Feb. 7, 2008

Related U.S. Application Data

(60) Provisional application No. 60/833,084, filed on Jul. 25, 2006.

(51) Int. Cl.
*G01N 31/00* (2006.01)
*G01N 33/53* (2006.01)
(52) U.S. Cl. ........... 435/7.1; 422/50; 530/300; 530/350; 436/501; 436/506; 436/518
(58) Field of Classification Search .................. None
See application file for complete search history.

(56) References Cited

U.S. PATENT DOCUMENTS

2006/0134698 A1 6/2006 Jin et al.

OTHER PUBLICATIONS

Biesiadecki et al. (The Journal of Biological Chemistry, vol. 277, No. 21, May 24, 2002, pp. 18459-18468).*
Jin et al. (Biochemistry, 2000, vol. 39, pp. 11702-11713).*
Biesiadecki et al. The Journal of Biological Chemistry, vol. 277, No. 21, May 24, 2002, pp. 18459-18468.*
Biesiadecki et al. (Journal of Biophysics, Feb. 15, 2005, p. 360a).*
Anderson et al., Molecular basis of human cardiac troponin T isoforms expressed in the developing, adult, and failing heart. *Circ. Res.* 76: 681-6 (1995).
Barbato et al., Proteolytic N-terminal truncation of cardiac troponin I enhances ventricular diastolic function. *J. Biol. Chem.* 280: 6602-9 (2005).
Biesiadecki et al. N-terminal truncation of cardiac troponin T by restricted proteolysis in myocardial ischemia-reperfusion. *Biophys. J.* 88:360a (2005).
Biesiadecki et al., Cardiac troponin T variants produced by aberrant splicing of multiple exons in animals with high instances of dilated cardiomyopathy. *J. Biol. Chem.* 277: 50275-85 (2002).
Biesiadecki et al., Exon skipping in cardiac troponin T of turkeys with inherited dilated cardiomyopathy. *J. Biol. Chem.* 277: 18459-68 (2002).
Breitbart et al., Complete nucleotide sequence of the fast skeletal troponin T gene. Alternatively spliced exons exhibit unusual interspecies divergence. *J. Mol. Biol.* 188: 313-24 (1986).
Chandra et al., The N-terminal region of troponin T is essential for the maximal activation of rat cardiac myofilaments. *J. Mol. Cell Cardiol.* 31: 867-80 (1999).

Colantonio et al., Stunned peri-infarct canine myocardium is characterized by degradation of troponin T, not troponin I. *Cardiovasc. Res.* 63:217-25 (2004).
Communal et al., Functional consequences of caspase activation in cardiac myocytes. *Proc. Natl. Acad. Sci. U.S.A.* 99: 6252-6 (2002).
Cong et al., The role of autolysis in activity of the Ca2+-dependent proteinases (mu-calpain and m-calpain). *J. Biol. Chem.* 264: 10096-103 (1989).
Di Lisa et al., Specific degradation of troponin T and I by mu-calpain and its modulation by substrate phosphorylation. *Biochem. J.* 308:57-61 (1995).
Foster et al., C-terminal truncation of cardiac troponin I causes divergent effects on ATPase and force: implications for the pathophysiology of myocardial stunning. *Circ. Res.* 93: 917-24 (2003).
Fujita et al., Expression in *Escherichia coli* and a functional study of a beta-troponin T 25 kDa fragment of rabbit skeletal muscle. *J. Biochem.* 112: 306-8 (1992).
Goll et al., The calpain system. *Physiol. Rev.* 83: 731-801 (2003).
Gomes et al., Cardiac troponin T isoforms affect the $Ca^{2+}$ sensitivity and inhibition of force development. Insights into the role of troponin T isoforms in the heart. *J. Biol. Chem.* 277: 35341-9 (2002).
Guttmann et al., Oxidation inhibits substrate proteolysis by calpain I but not autolysis. *J. Biol. Chem.* 272: 2005-12 (1997).
Hinkle et al., Roles for the troponin tail domain in thin filament assembly and regulation. A deletional study of cardiac troponin T. *J. Biol. Chem.* 274: 7157-64 (1999).
Hirano et al., Regulation of myosin phosphorylation and myofilament $Ca^{2+}$ sensitivity in vascular smooth muscle. *J. Smooth Muscle Res.* 40: 219-36 (2004).
Huang et al., Fast skeletal muscle troponin T increases the cooperativity of transgenic mouse cardiac muscle contraction. *J. Physiol. (London)* 520: 231-42 (1999).
Huang et al., Genomic sequence and structural organization of mouse slow skeletal muscle troponin T gene. *Gene* 229: 1-10 (1999).
Jin et al., Rapid purification of mammalian cardiac troponin T and its isoform switching in rat hearts during development. *J. Biol. Chem.* 263: 7309-15 (1988). Jin et al., Expression of cDNAs encoding mouse cardiac troponin T isoforms: characterization of a large sample of independent clones. *Gene* 168: 217-21 (1996).
Jin et al., A role for serine-175 in modulating the molecular conformation of calponin. *Biochem. J.* 350:579-588 (2000).
Jin et al., Cloned rat cardiac titin class I and class II motifs. Expression, purification, characterization, and interaction with F-actin. *J. Biol. Chem.* 270: 6908-16 (1995).
Jin et al., Complete nucleotide sequence and structural organization of rat cardiac troponin T gene. A single gene generates embryonic and adult isoforms via developmentally regulated alternative splicing. *J. Mol. Biol.* 227: 1269-76 (1992).
Jin et al., Conformational modulation of slow skeletal muscle troponin T by an NH(2)-terminal metal-binding extension. *Am. J. Physiol. Cell Physiol.* 279: C1067-77 (2000).
Jin et al., Evolution of a metal-binding cluster in the NH(2)-terminal variable region of avian fast skeletal muscle troponin T: functional divergence on the basis of tolerance to structural drifting. *J. Mol. Evol.* 52: 103-16 (2001).

(Continued)

*Primary Examiner* — Lisa Cook
(74) *Attorney, Agent, or Firm* — Marshall, Gerstein & Borun LLP

(57) ABSTRACT

Methods for diagnosing, determining the likelihood of developing cardiac disease by measuring the level of a truncated form of cardiac Troponin T are provided. Also provided are methods for preventing treating or ameliorating a symptom associated with cardiac disease by administering a therapeutically effective amount of a modulator of the posttranslational production of N-terminally truncated forms of cardiac troponin T.

15 Claims, 16 Drawing Sheets

OTHER PUBLICATIONS

Jin et al., Modulation of troponin T molecular conformation and flexibility by metal ion binding to the $NH_2$-terminal variable region. *Biochemistry* 39: 11702-13 (2000).

Jin et al., The highly conserved COOH-terminus of troponin I forms a $Ca^{2+}$ modulated allosteric domain in the troponin complex. *Biochemistry* 40: 2623-31 (2001).

Jin et al., Three alternatively spliced mouse slow skeletal muscle troponin T isoforms: conserved primary structure and regulated expression during postnatal development. *Gene* 214: 121-9 (1998).

Jin et al., Truncation by Glu180 nonsense mutation results in complete loss of slow skeletal muscle troponin T in a lethal nemaline myopathy. *J. Biol. Chem.* 278: 26159-65 (2003).

Jossi et al., All troponins are not created equal. *Intern. Med. J.* 36: 325-7 (2006).

Kitamura et al., Mechanism of production of troponin T fragments during postmortem aging of porcine muscle. *J. Agric. Food Chem.* 53: 4178-81 (2005).

Layland et al., Regulation of cardiac contractile function by troponin I phosphorylation. *Cardiovasc. Res.* 66: 12-21 (2005).

Leavis et al., Thin filament proteins and thin filament-linked regulation of vertebrate muscle contraction. *CRC Crit. Rev. Biochem.* 16: 235-305 (1984).

Lin et al., Monoclonal antibodies against chicken tropomyosin isoforms: production, characterization, and application. *Hybridoma* 4: 223-42 (1985).

Martin, Turnover of cardiac troponin subunits. Kinetic evidence for a precursor pool of troponin-1. *J. Biol. Chem.* 256: 964-8 (1981).

Murphy et al., Transgenic mouse model of stunned myocardium. *Science* 287: 488-91 (2000).

Murphy, Heart failure, myocardial stunning, and troponin: a key regulator of the cardiac myofilament. *Congest Heart Fail.* 12: 32-8; quiz 39-40 (2006).

Ogut et al., Developmentally regulated, alternative RNA splicing-generated pectoral muscle-specific troponin T isoforms and role of the $NH_2$-terminal hypervariable region in the tolerance to acidosis. *J. Biol. Chem.* 273: 27858-66 (1998).

Ohtsuki et al., A 26K fragment of troponin T from rabbit skeletal muscle. *J. Biochem.* 95: 1337-42 (1984).

Pan et al., Deletion of the first 45 NH2-terminal residues of rabbit skeletal troponin T strengthens binding of troponin to immobilized tropomyosin. *J. Biol. Chem.* 266: 12432-8 (1991).

Pearlstone et al., Binding of troponin-T fragments to several types of tropomyosin. Sensitivity to Ca2+ in the presence of troponin-C. *J. Biol. Chem.* 257: 10587-92 (1982).

Pearlstone et al., The interaction of rabbit skeletal muscle troponin-T fragments with troponin-I. *Can. J. Biochem.* 63: 212-8 (1985).

Perry, Troponin T: genetics, properties and function. *J. Muscle Res. Cell Motil.* 19: 575-602 (1998).

Piper et al., Cellular mechanisms of ischemia-reperfusion injury. *Ann. Thorac. Surg.* 75: S644-8 (2003).

Smillie, Preparation and identification of alpha- and beta-tropomyosins. *Methods Enzymol.* 85: 234-41 (1982).

Solaro et al., The purification of cardiac myofibrils with Triton X-100. *Biochim. Biophys. Acta.* 245: 259-62 (1971).

Sumandea et al., Molecular and integrated biology of thin filament protein phosphorylation in heart muscle. *Ann. NY Acad. Sci.* 1015: 39-52 (2004).

Takeda et al., Structure of the core domain of human cardiac troponin in the Ca(2+)-saturated form. *Nature* 424: 35-41 (2003).

Tobacman, Thin filament-mediated regulation of cardiac contraction. *Annu. Rev. Physiol.* 58: 447-81 (1996).

Vinogradova et al., Ca(2+)-regulated structural changes in troponin. *Proc. Natl. Acad. Sci. U.S.A.* 102: 5038-43 (2005).

Wang et al., An alpha-mercaptoacrylic acid derivative is a selective nonpeptide cell-permeable calpain inhibitor and is neuroprotective. *Proc. Natl. Acad. Sci. U.S.A.* 93: 6687-92 (1996).

Wang et al., Comparative studies on the expression patterns of three troponin T genes during mouse development. *Anat. Rec.* 263: 72-84 (2001).

Wang et al., Conformational modulation of troponin T by configuration of the $NH_2$-terminal variable region and functional effects. *Biochemistry* 37: 14519-28 (1998).

Wang et al., Primary structure and developmental acidic to basic transition of 13 alternatively spliced mouse fast skeletal muscle troponin T isoforms. *Gene* 193: 105-114 (1997).

Yu et al., A proteolytic $NH_2$-terminal truncation of cardiac troponin I that is up-regulated in simulated microgravity. *J. Biol. Chem.* 276: 15753-60 (2001).

Yu et al., Role of myofilament protein isofrm regulation in the decreases in contractile force and tolerance to fatigue of slow skeletal muscles after unloading. *Biophys. J.* 82: 394a (2002).

Zhang et al., Selective deletion of the $NH_2$-terminal variable region of cardiac troponin T in ischemia reperfusion by myofibril-associated μ-Calpain cleavage. *Biochemistry* 45: 11681-94 (2006).

Zot et al., Structural aspects of troponin-tropomyosin regulation of skeletal muscle contraction. *Annu. Rev. Biophys. Biophys. Chem.* 16: 535-59 (1987).

* cited by examiner

US 8,008,021 B2

N-TERMINAL TRUNCATION OF CARDIAC TROPONIN SUBUNITS AND THEIR ROLES IN CARDIOVASCULAR DISEASE

The invention was made with U.S. Government support under contract nos. HL078773, AR048816 and HD044824 awarded by the National Institutes of Health. The U.S. Government has certain rights to this invention.

FIELD OF THE INVENTION

The invention generally relates to diagnostic and therapeutic methods for cardiopulmonary health.

BACKGROUND OF THE INVENTION

Cardiovascular disease remains a major health problem throughout the developed world, annually ranking at or near the top in terms of human cost in poor health or death, and in terms of financial cost for treatment and prevention. Despite enormous efforts on the parts of both medical practitioners and basic researchers in human health and related fields, cardiovascular disease continues to be a significant problem. The prevalence and persistence of this medical ill has led to steadily increasing efforts to combat it, including molecular biological investigations of the physiological events attending cardiovascular health and disease.

Actin-activated myosin ATPase (i.e., the actomyosin ATPase) powers muscle contraction in a process regulated by Ca2+ binding to the thin filament-associated proteins, tropomyosin and the troponin complex. The current model for striated muscle (i.e., cardiac and skeletal muscle) contraction has contraction initiated by a rise in the cytoplasmic calcium concentration [Ca2+], which results in binding of Ca2+ to troponin C (TnC). Ca2+-TnC binding induces a series of allosteric changes in TnC, TnI, TnT, the three subunits of troponin, and tropomyosin. These conformational changes allow the myosin head to form a strong cross-bridge with the actin filament. This interaction activates the myosin ATPase, displacing the thin filaments relative to the thick filaments, thus leading to a shortening of the sarcomere and contraction of the muscle.

Cardiac and skeletal muscle contraction is activated by $Ca^{2+}$ via troponin-tropomyosin in the actin thin filament regulatory system (1-3). Troponin C (TnC) is the Ca2+-binding subunit, troponin T (TnT) is the tropomyosin-binding subunit, and troponin I (TnI) is the inhibitory subunit. Troponin T (1) is the anchoring subunit of the troponin complex (4). Three muscle type-specific TnT isoform genes have evolved in higher vertebrates (5-7) and alternative RNA splicing further produces multiple protein isoforms (8-10). The various TnT isoforms mainly differ in their $NH_2$-terminal structures. The amino acid sequence of the $NH_2$-terminal region of TnT is hypervariable among the cardiac, slow and fast skeletal muscle TnT isoforms and is regulated by alternative splicing during perinatal heart and muscle development (8, 9).

The $NH_2$-terminal region of TnT does not contain any known binding sites for other thin filament proteins (11-13). Nonetheless, deletion of the $NH_2$-terminal cTnT fragment decreases contractility of the heart (14, 16). Deleting the $NH_2$-terminal variable region does not diminish the regulatory activity of troponin (14-16), suggesting that the $NH_2$-terminal variable region of TnT may function as a modulatory or regulatory structure. Supporting this view are alterations in the TnT $NH_2$-terminal structure that affect the $Ca^{2+}$-regulation of muscle contraction. It has been reported that $NH_2$-terminal alternatively spliced TnT isoforms convey significant changes in the activation of actomyosin ATPase (17). Aberrant splicing of cardiac TnT (cTnT) in the $NH_2$-terminal region is found in both hypertrophic and failing human hearts (18) and in animal models with dilated cardiomyopathy (19, 20). Consistent with the functional effects, studies showed that $NH_2$-terminal alterations in TnT alter the overall protein conformation (21, 22), and the binding of TnT to tropomyosin, TnI and TnC (21, 23).

Serum cardiac troponin T has been used in the diagnosis of acute myocardial infarction for some time. Commercially available assays for serum cTnT, however, have two intrinsic problems. First, there are conserved, or similar, regions common to cardiac and skeletal muscle TnTs, and any assay dependent on the conserved region of cTnT will be compromised by detection of skeletal TnTs, resulting in false positives and reduced measurement accuracy. Second, commercially available diagnostic kits provide materials for immunoassays that rely on antibodies raised against intact, full-length cTnT, an environment in which the highly cardiac-specific N-terminal variable region of full-length cTnT lacks significant immunogenicity.

Like the TnT subunit, the TnI subunit shows a core structure conserved in all TnI isoforms. Cardiac TnI (cTnI) has an approximately 30-amino-acid N-terminal extension that is not present in fast and slow skeletal muscle TnIs. This N-terminal extension does not contain binding sites for other thin filament proteins, but contains serine residues 23 and 24 which are protein kinase A (PKA) substrates. With β-adrenergic stimulation, phosphorylation of these serine residues facilitates myocardial relaxation by decreasing the affinity of TnC for Ca2+.

Notwithstanding this understanding of molecular events implicated in cardiovascular disease, and despite recognition that troponin measurements are central to the diagnosis, management and risk stratification of acute cardiovascular events, existing troponin assays have proven inaccurate and insufficiently reliable. For example, a comparison of the measured troponin found in blood samples using three troponin I assays (Centaur, Architect and point-of-care iSTAT) and one troponin T assay (Roche Elecys) revealed significant discrepancies in the measured quantities of troponin. Jossi et al., Intern. Med. J. 36:326-327 (2006).

Thus, there remains a need in the art for methods of preventing, diagnosing and treating cardiovascular diseases and disorders, as well as methods of screening for therapeutics useful in such methods.

SUMMARY

The invention satisfies at least one of the aforementioned needs in the art by providing methods of preventing, diagnosing and treating a variety of cardiopulmonary diseases, disorders and conditions, by monitoring, or manipulating the level of, a posttranslationally processed form of cardiac troponin T found in vivo. In particular, the methods comprise monitoring and/or manipulating the level of an N-terminally truncated form of cTnT, e.g., by detecting that truncated cTnT, by detecting the N-terminal fragment lost from intact, holo-cTnT, and/or by monitoring the relative level of intact, holo-cTnT.

In one aspect, the invention provides a method of determining the likelihood of developing, or diagnosing, a cardiac disease comprising (a) obtaining a biological sample from a subject; (b) measuring the level of at least one truncated form of cardiac troponin T in the sample; and (c) determining the likelihood of developing, or diagnosing, a cardiac disease based on the measured level of at least one truncated form of cardiac troponin T in the sample.

In the aforementioned aspect of the invention, the subject may be a human patient, or an animal such as a mammal, e.g., domesticated mammals, zoo animals, pets, and the like. Further, this aspect comprehends a truncated form of cardiac troponin T in the form of any of the N-terminally truncated cTnT forms disclosed herein or known in the art, such as $cTnT_{72-291}$ lacking the N-terminal 71 amino acids of human complete cardiac troponin T. Additionally, determining the likelihood of developing, or diagnosing, a cardiovascular disease may be based on measurements of the free N-terminal cTnT fragment released from the core cTnT during truncation. Suitable for these methods are any biological samples in which one of skill in the medical arts would reasonably expect to find a cTnT, such as a blood sample, saliva sample, or other body fluid or tissue sample. Any technique known in the art for measuring a truncated form of a protein, such as truncated cTnT, may be used in these methods, including any of a variety of immunoassays (e.g., solution-based or solid-phase, single antibody or sandwich assay, fluoroimmunoassay or radioimmunoassay, and the like). In some embodiments, the immunoassay comprises a specific binding partner, such as an antibody, that selectively binds to the truncated form of cardiac troponin T, i.e., that exhibits a detectable preference for binding to a truncated form of cTnT relative to binding to the full-length, whole cTnT. In some embodiments, the truncated form of cTnT is human $cTnT_{72-291}$.

In some embodiments, the immunoassay methods comprise a differential measurement of a truncated cTnT based on measures of the levels of at least two forms of cTnT in the sample. For example, the invention comprehends immunoassays in which a truncated form of cTnT (e.g., an N-terminally truncated cTnT or the N-terminal peptide released from core cTnT in the process of truncation, which is itself C-terminally truncated) is measured and in which the full-length, whole cTnT is measured, with the two measurements being compared to arrive at a differential measurement of the truncated cTnT. In some of these embodiments, the differential measurement comprises detecting antibody binding and distinguishing cTnT forms by size, for example by performing a Western blot analysis on a sample. In other embodiments, the differential measurement comprises a comparison of the measured quantities of a truncated cTnT and a full-length cTnT.

Another aspect of the invention is a method of preventing a cardiac disease comprising administering a therapeutically effective amount of a compound selected from the group consisting of a truncated cTnT (i.e., an N-terminally truncated cTnT) and an inducer of posttranslationally truncated cTnT. A related aspect of the invention further comprises administering a therapeutically effective amount of a compound selected from the group consisting of an inducer of posttranslationally truncated cTnI, a truncated cTnI, a $Ser_{23}$-phosphorylated cTnI and a $Ser_{24}$-phosphorylated cTnI.

Yet another aspect of the invention provides a method of treating a cardiac disease comprising administering a therapeutically effective amount of a compound selected from the group consisting of a truncated cTnT and an inducer of posttranslationally truncated cTnT. A related aspect of the invention further comprises administering a therapeutically effective amount of a compound selected from the group consisting of a truncated cTnI (N-terminally truncated), an inducer of a posttranslationally truncated cTnI (N-terminally truncated), a $Ser_{23}$-phosphorylated cTnI and a $Ser_{24}$-phosphorylated cTnI.

Still another aspect of the invention is drawn to a method of ameliorating a symptom associated with a cardiac disease comprising administering an ameliorative amount of a compound selected from the group consisting of a truncated cTnT (N-terminally truncated) and an inducer of posttranslationally truncated cTnT (N-terminally truncated). A related aspect of the invention further comprises administering an ameliorative amount of a compound selected from the group consisting of a truncated cTnI (N-terminally truncated), an inducer of a posttranslationally truncated cTnI (N-terminally truncated), a $Ser_{23}$-phosphorylated cTnI and a $Ser_{24}$-phosphorylated cTnI.

For the preventive, therapeutic and ameliorative methods of the invention, any N-terminally truncated form of cTnT may be administered, such as human $cTnT_{72-291}$ (i.e., human truncated cTnT missing the N-terminal 71 amino acids of the full-length cTnT). In each of these methods, moreover, the inducer may be a reagent that removes, deactivates or inhibits a Calpain inhibitor, such as a mu-Calpain inhibitor, associated with a targeting composition selected from the group consisting of a targeting molecule and a targeting vehicle. A targeting composition is any composition capable of specifically interacting with a desired target, such as a cardiomyocyte. In some embodiments, the targeting composition specifically interacts with a cardiomyocyte membrane-bound polypeptide or protein. The specific interaction will typically be a result of a specific binding interaction, such as antigen-antibody or ligand-receptor binding. It is contemplated that the targeting composition may be a targeting molecule, such as an antibody to a cardiomyocyte-specific polypeptide antigen (e.g., a cardiomyocyte membrane-bound polypeptide), or may be a targeting vehicle, such as a liposome, provided that the vehicle can target a cardiomyocyte, for example by incorporating a target molecule, e.g., an antibody or ligand, in the liposomal membrane. Other targeting compositions known in the art are suitable for use in the invention.

In yet another aspect, the invention provides a method of screening for a modulator of posttranslational, N-terminal truncation of cTnT comprising (a) incubating a mixture of a candidate modulator and a full-length cTnT polypeptide; (b) detecting the pattern of cTnT forms in the mixture; and (c) identifying the candidate modulator as a modulator of posttranslationally truncated cTnT when the pattern of cTnT forms in the presence of the candidate modulator differs from the pattern of cTnT forms in the absence of the candidate modulator. In some embodiments, the patterns of cTnT forms reflects cTnTs of different sizes; in other embodiments, the patterns reflect different quantities of approximately same-sized cTnT forms. In some embodiments, the modulator is an inducer of posttranslational N-terminal truncation of cTnT. In some embodiments, the relative sizes of cTnT forms are determined by migration rate differences during gel electrophoresis.

As noted above, the invention provides combination therapies for the treatment of a cardiac disease, disorder or condition. For example, the invention provides a method for treating a cardiac disease comprising administering a therapeutically effective amount of an N-terminally truncated TnT and delivering a therapeutically effective amount of a protein selected from the group consisting of N-terminally truncated TnT and a modified TnI, to a subject in need thereof. As would be understood by practitioners in the field, a "therapeutically effective amount" of an individual therapeutic used in a combination therapy may differ from the therapeutically effective amount of that therapeutic when used alone, due to additive or synergistic effects of the combination of therapeutics.

In related aspects, the invention provides a method for treating a cardiac disorder comprising producing a therapeutically effective amount of an N-terminally truncated troponin T in a host cell of a patient or non-human animal in need of treatment. The invention further comprehends the administration of a polynucleotide encoding an N-terminally truncated troponin T, such as an N-terminally truncated cTnT. The production results from expression of the polynucleotide, or nucleic acid, encoding an N-terminally truncated cardiac troponin T in a host cell of an organism being treated. Further, the invention provides for combination therapies in which polynucleotides encoding an N-terminally truncated TnT (e.g., cTnT) and an N-terminally truncated TnI (e.g., cTnI) are administered to a host cell of a patient or non-human animal in need, thereby providing for the recombinant production of a therapeutically effective amount of an N-terminally truncated troponin T (e.g., cTnT) and a therapeutically effective amount of an N-terminally truncated troponin I (e.g., cTnI).

For all combination therapies disclosed herein, it is contemplated that each therapeutic will be administered at the same, or different, time(s) and will be administered as part of a single therapeutic composition or as physically distinct compositions, whether co-administered or not. For administration schedules that provide the therapeutics separated in time, all possible temporal spacings and orders of administration are contemplated.

Other features and advantages of the present invention will be better understood by reference to the following detailed description, including the drawing and the examples.

DETAILED DESCRIPTION

Figure 1:
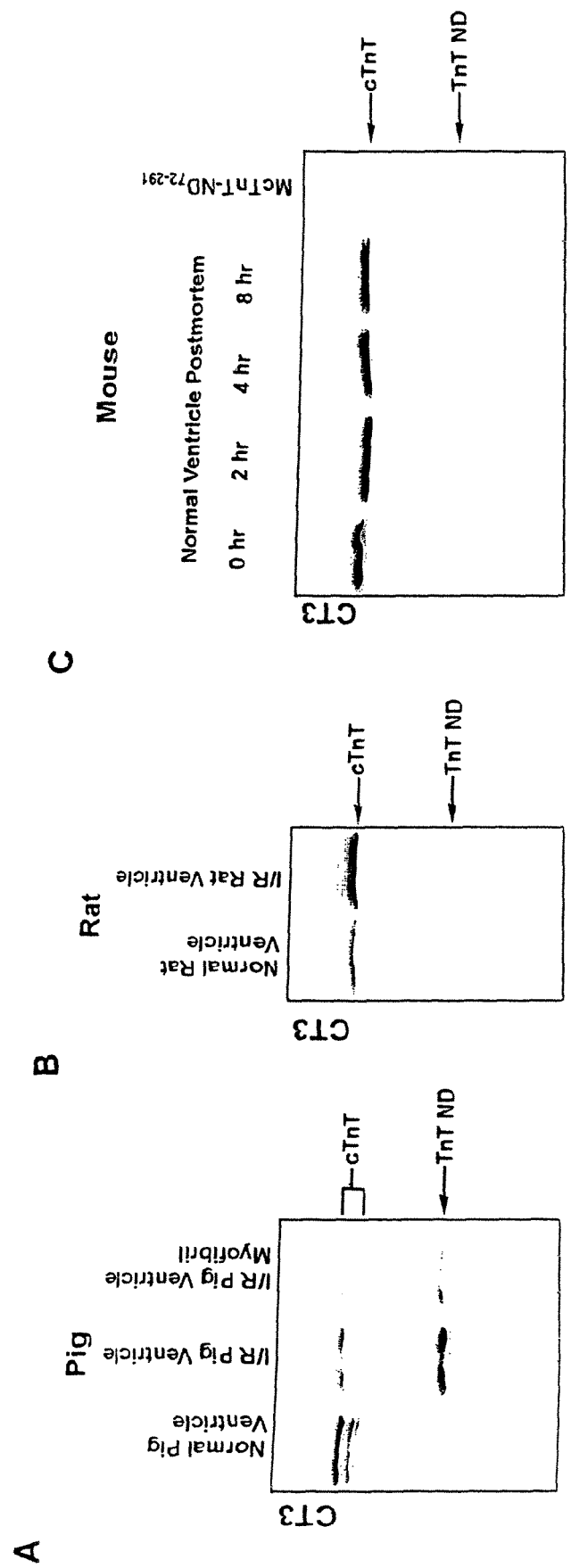
FIG. 1. A cTnT fragment found in ischemia-reperfused cardiac muscle. A. Western blot of cTnT in a normal pig ventricle using CT3 mAb Western blot showed cTnT and a specific cTnT fragment in working pig heart preparations after ischemia-reperfusion treatment. B. While there was no detectable degradation of cTnT in rat heart after one-hour in vitro perfusion, CT3 mAb Western blot showed that a specific cTnT fragment was produced in working rat heart preparations after ischemia-reperfusion treatment. C. Cardiac muscle samples from adult C57BL/6 mice were prepared at 0, 2, 4, and 8 hours postmortem and analyzed by SDS-PAGE and CT3 mAb Western blotting. The results showed that there was no detectable degradation of cardiac TnT due to the postmortem ischemia.

Removal of the N-terminal variable region of cTnT decreases the contractility of the heart, and this proteolytic modification of cTnT provides a rapid mechanism to adjust muscle contractility under stress conditions. This removal of the N-terminal variable region, or truncation, occurs in vivo within a few minutes of the heart undergoing ischemia reperfusion. In acute forms of cardiovascular disease, such as acute myocardial infarction, this transient adjustment protects the cardiac muscle by diminishing or preventing contracture-induced injury, a common feature of cardiovascular insult such as ischemia reperfusion. As noted in U.S. Ser. No. 11/311,472, incorporated herein by reference, modification of the N-terminal region of cTnI, either by proteolytic cleavage of an N-terminal peptide or by derivatizations such as phosphorylation (e.g., phosphorylation at $Ser_{23}$ and/or $Ser_{24}$ of cTnI) improves cardiac relaxation.

Accordingly, the methods and compositions of the invention provide more sensitive, specific and reliable approaches to detecting cardiovascular diseases and disorders, particularly acute cardiovascular events like myocardial infarction. Cardiac TnT is cleaved in vivo to yield a cardiac-specific N-terminal cTnT peptide fragment, and an N-terminally truncated cTnT. Analogously, cardiac TnI is modified in vivo and an N-terminal fragment of cTnI is cleaved from holo cTnI to yield truncated peptides. Although the N-terminal peptides lack significant immunogenicity when present in the intact cardiac troponin subunits, isolation of these N-terminal peptide fragments facilitates efforts to obtain binding partners, e.g., antibodies, specific to each N-terminal fragment. These specific binding partners are useful in diagnostic assays for troponin levels indicative of cardiovascular disease and in methods of monitoring treatments to address such disease.

The invention also provides binding partners specific for truncated cTnI or for truncated cTnT, which are also useful in diagnostic and monitoring methods. Also contemplated are comparative diagnostic and/or monitoring methods comprising binding partners for any two or more forms of cTnT (i.e., full-length cTnT or holo cTnT, N-terminal fragment of cTnT, truncated form of cTnT) and/or cTnI (i.e., full-length cTnI or holo cTnI, N-terminal fragment of cTnI, truncated cTnI, functionally truncated form of cTnI through, e.g., phosphorylation at $Ser_{23}$ and/or $Ser_{24}$). Beyond the aforementioned diagnostic and monitoring methods, the invention provides screening methods for modulators of cTnT truncation and/or cTnI truncation. Also provided by the invention are compositions (e.g., prophylactics, therapeutics and kits of same) comprising the N-terminal cTnT fragment, the N-terminal cTnI fragment, or both fragments, optionally in combination with a pharmaceutically acceptable carrier, diluent or adjuvant.

Regulated development from embryonic to adult TnT isoforms establishes the functional significance of the $NH_2$-terminal structural variation of cTnT. In contrast to the relatively slow response at the gene regulation and RNA splicing levels, posttranslational regulation provides a mechanism for rapid adaptation to acute stress. The most prominently studied posttranslational mechanism of myofilament protein adaptation is phosphorylation (25-27). Proteolysis is usually associated with muscle deterioration under physiological or pathological stress conditions (28, 29). However, restricted proteolysis of cardiac troponin subunits, such as cardiac troponin T (cTnT) and/or cardiac troponin I (TnI), is disclosed herein and in U.S. Ser. No. 11/311,472 (incorporated herein by reference) as beneficial adaptations to stress conditions.

With respect to cTnI, a deletion of the $NH_2$-terminal phosphorylation sites has been found in rat cardiac muscle under simulated microgravity conditions (30). This specific structural modification of cardiac TnI has been demonstrated to enhance the relaxation of cardiac muscle as compensation to the decrease in cardiac preload in the microgravity model (31). It has been reported that $NH_2$-terminal truncated fast skeletal muscle TnT is produced during postmortal proteolysis in rabbit (32) and porcine muscle (33). It is not known whether this modification occurs in vivo.

Relevant to cTnT truncation is calpain, a calcium activated cysteine protease that has been found to play a regulatory role through the modification of proteins by proteolytic cleavage. Two major calpain isoforms have been identified in muscle cells. The μ-calpain (calpain 1) requires micromolar concentrations of calcium to activate and the m-calpain (calpain 2) requires millimolar concentrations of calcium (34, 35). Mu-Calpain is a myofibril-associated enzyme (34). It has been observed that μ-calpain can degrade TnT and TnI in vitro (36).

The data disclosed herein establish that a truncated cTnT is produced during myocardial ischemia-reperfusion, a stress condition that results in cardiac muscle injuries (37). Amino acid sequencing and protein fragment reconstruction revealed that the truncated cTnT is generated by a posttranslational modification to selectively remove the $NH_2$-terminal variable region and preserve the conserved core structure of TnT. TRITON® X-100 extraction of cardiac muscle fibers promoted the production of the $NH_2$ terminal-truncated cTnT (cTnT-ND), consistent with a myofibril-associated proteolytic activity. Supporting a role for μ-calpain in producing cTnT-ND, calpain inhibitors reduced cTnT-ND production in Triton-extracted myofibrils. Mu-Calpain treatment of cardiac myofibril and troponin complex reproduced cTnT-ND. Mu- Calpain treatment of isolated cTnT resulted in non-specific degradation, indicating that this structural modification is relevant to physiological structures of the myofilament. TRITON® X-100 treatment on transgenic mouse cardiac myofibrils overexpressing fast skeletal muscle TnT produced similar NH$_2$-terminal truncations of the exogenous and endogenous TnTs, despite the different amino acid sequences at the cleavage site, indicating that it is the myofilament structure that determines the specific cleavage. With the functional consequences of removing the NH$_2$-terminal variable region of TnT, the μ-calpain-mediated proteolytic modification of TnT provides an acute mechanism to adjust muscle contractility under stress conditions. In contrast to the commonly observed proteolytic destruction during ischemia-reperfusion injury (28), these data demonstrate a specific modification of troponin structure as a potentially functional adaptation.

Disclosed herein is a restricted proteolytic NH$_2$-terminal modification of cTnT in myocardial ischemia-reperfusion. This structural modification selectively removes the NH$_2$-terminal variable region and preserves the TnT core structure with functional implications. From characterizing its production by μ-calpain cleavage, the following observations suggest the significance of this study.

Regulatory role of the NH$_2$-terminal variable region of TnT. TnT is known as a protein with extended conformation in which the NH$_2$-terminal variable region is a part of the "tail" domain of troponin. The presence of TnI and TnC binding sites in the TnT COOH-terminal domain is confirmed by the X-ray crystallographic three-dimensional structure of partial cardiac (51) and skeletal muscle (52) troponins. The NH$_2$-terminal amino acid sequence is hypervariable among TnT isoforms and regulated by alternative RNA splicing during heart and skeletal muscle development. This region does not contain binding sites for other thin filament proteins but its structural alteration shows fine tuning effects on the Ca$^{2+}$-regulation of muscle contraction. It has been proposed that the NH$_2$-terminal variable region has its functional effects by modulating the molecular conformation and activity of other regions of TnT (21-23).

The fact that the NH$_2$-terminal region of TnT does not contain binding sites for other thin filament proteins allows for its high sequence variability and forms the foundation for a wide range of modulating effects. The NH$_2$-terminal truncated cTnT produced during myocardial ischemia-reperfusion selectively removes the entire NH$_2$-terminal variable region while retaining the conserved core structure of TnT. This mechanism represents the most extreme modification of TnT in comparison to the developmental (8) and pathological (20) alternative splicing variants. The molecular evolution of the TnT NH$_2$-terminal variable region demonstrates an increase in length and complexity (53). Therefore, the removal of the entire NH$_2$-terminal variable region in cTnT may be a mechanism to resume a default fundamental functional state of troponin as a compensatory response to stress conditions.

Figure 3:
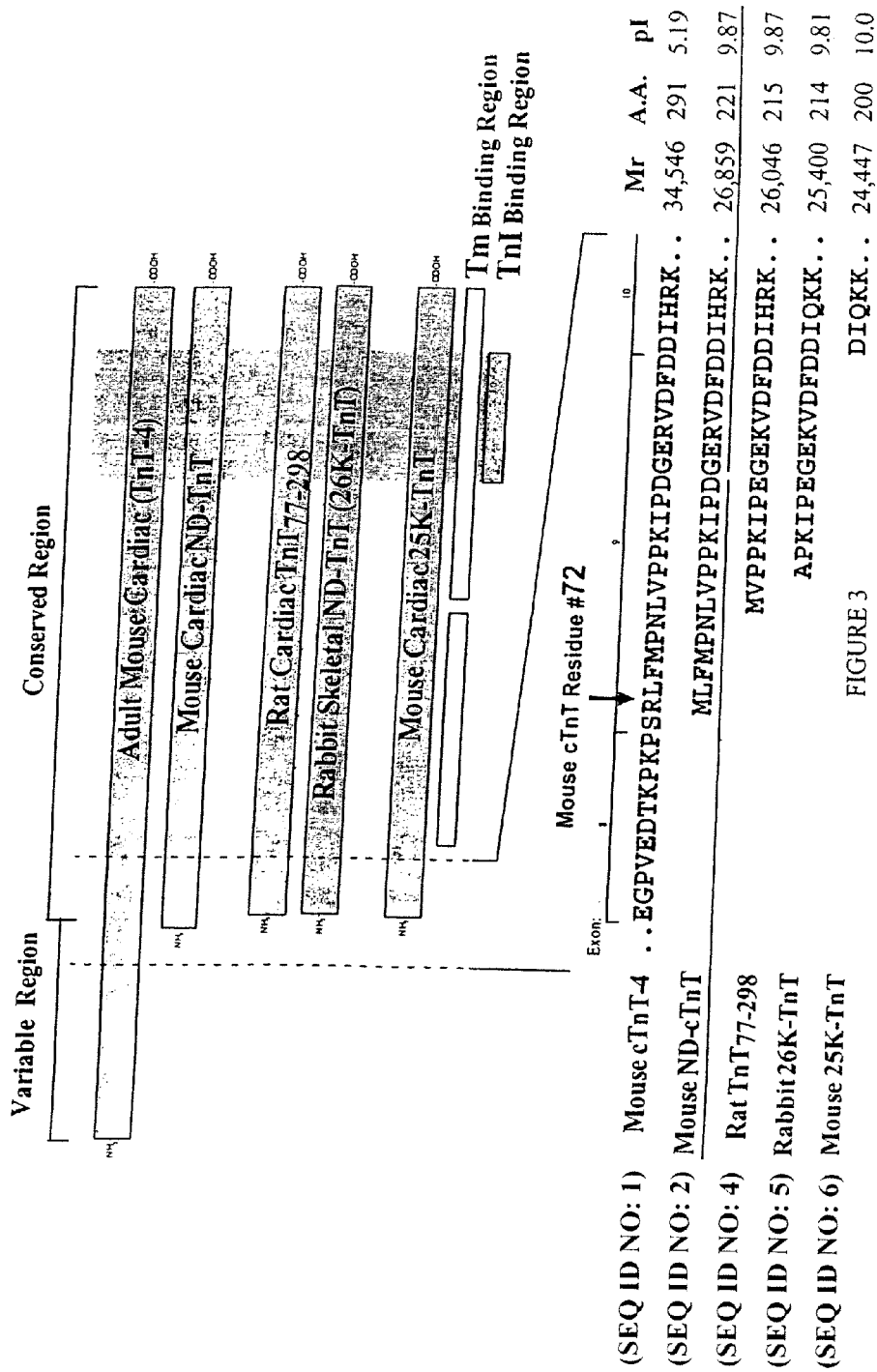
FIG. 3. $NH_2$-terminal truncations of cTnT. $NH_2$-terminal amino acid sequencing of the cTnT fragment revealed a single truncation site between residues $Arg_{71}$ and $Leu_{72}$. Amino acid sequence alignment demonstrated that the cTnT $NH_2$-terminal truncation removes the entire variable region (FIG. 5), similar to the $NH_2$-terminal truncated fast TnT previously isolated from rabbit skeletal muscle (rabbit 26-kDa fsTnT, 32) and a molecular model previously studied (Rat $cTnT_{77-298}$, 16). In contrast, a caspase cleavage-produced cTnT fragment (Rat 25-kDa cTnT, 29) involves the deletion of a part of the conserved region.

Expected functional consequences of selective deletion of the NH$_2$-terminal variable region of cTnT. Investigations into the structure-function relationship of TnT have revealed TnT molecules with NH$_2$-terminal deletions, consistent with the structure of human cTnT-ND$_{72-291}$ (FIG. 3). For example, a naturally occurring NH$_2$-terminal truncation of rabbit fast skeletal muscle TnT fragment (the TnT 26K fragment, 32) is known. This fragment is able to form a functional troponin complex that exhibits a higher binding strength to tropomyosin compared with that of troponin containing the intact TnT. Reconstituted troponin complex containing the NH$_2$-terminal truncated fast TnT also conferred a decrease in the maximum activation of actomyosin-S1 MgATPase (14). The results disclosed herein show that cTnT-ND$_{72-291}$ also has an increased affinity for tropomyosin (FIG. 12B), indicating similar functional effects. Further studies using an NH$_2$-terminal deleted cTnT in reconstituted myofilaments demonstrated that the removal of an NH$_2$-terminal domain resulted in decreased myofibril force development (16). These data are consistent with the NH$_2$-terminal truncation of TnT not being a form of destructive damage, but a form of regulatory control in both cardiac and skeletal muscles, which is expected to have a fundamental role in modulating contractility during physiological and pathological adaptations.

cTnT-ND$_{72-291}$ is retained in the myofibrils of ischemia-reperfused cardiac muscle and, therefore, is expected to participate in the thin filament regulatory function. A consensus change found in previous studies due to the presence of NH$_2$-terminal truncated TnT is a decreases in the maximum Ca$^{2+}$-activated actomyosin ATPase activity and myofibril force (14-16). Such a decrease of Ca$^{2+}$ activation by deleting the NH$_2$-terminal domain of cTnT during myocardial ischemia-reperfusion is expected to contribute to the depressed function after ischemia, but may also provide a protection against Ca$^{2+}$ overload-induced injuries (54). The observation that the NH$_2$-terminal truncated cTnT plays a compensatory rather than destructive function is supported by the observation that transgenic mice over-expressing high levels of cTnT-ND$_{72-291}$ in cardiac muscle did not show apparent cardiac dysfunction (37).

Figure 8:
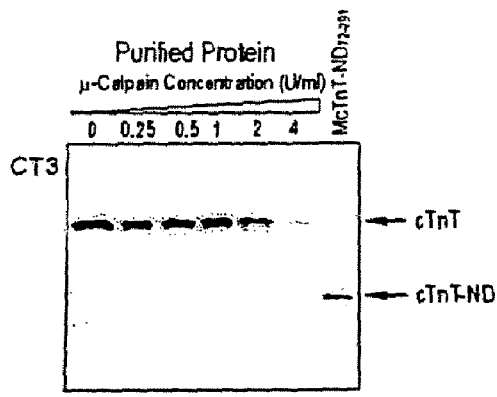
FIG. 8. μ-Calpain treatment of cardiac myofibril reproduced the NH$_2$-terminal truncated cTnT fragment. A. Western blot using anti-cTnT mAb CT3 showed that μ-calpain treatment effectively degraded purified bovine cTnT as that reported previously (36), but did not produce a specific fragment. B. In contrast, μ-calpain treatment of bovine cardiac myofibrils effectively reproduced the cTnT-ND fragment. The results demonstrate that the cTnT-ND modification by μ-calpain is dependent on the myofibril structure. Densitometry plots of the accompanying SDS-PAGE gel showed no apparent degradation of other major myofibrillar proteins, including myosin, actin and Tm, under the μ-calpain treatment conditions.
Figure 8:
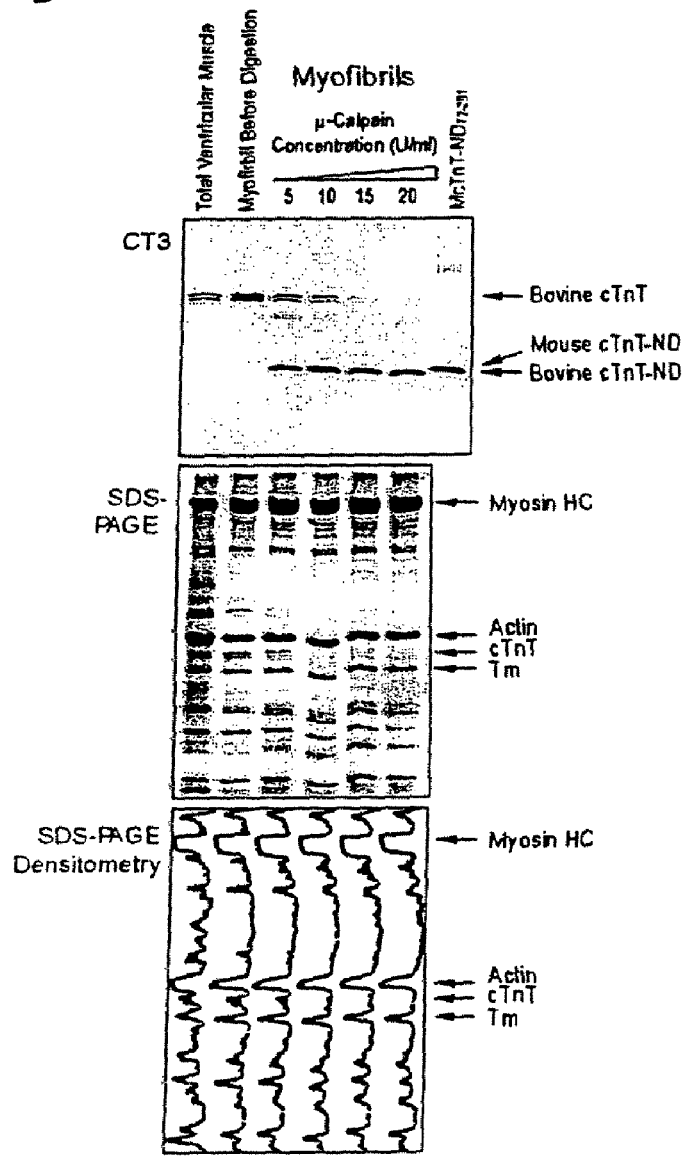
Figure 10:
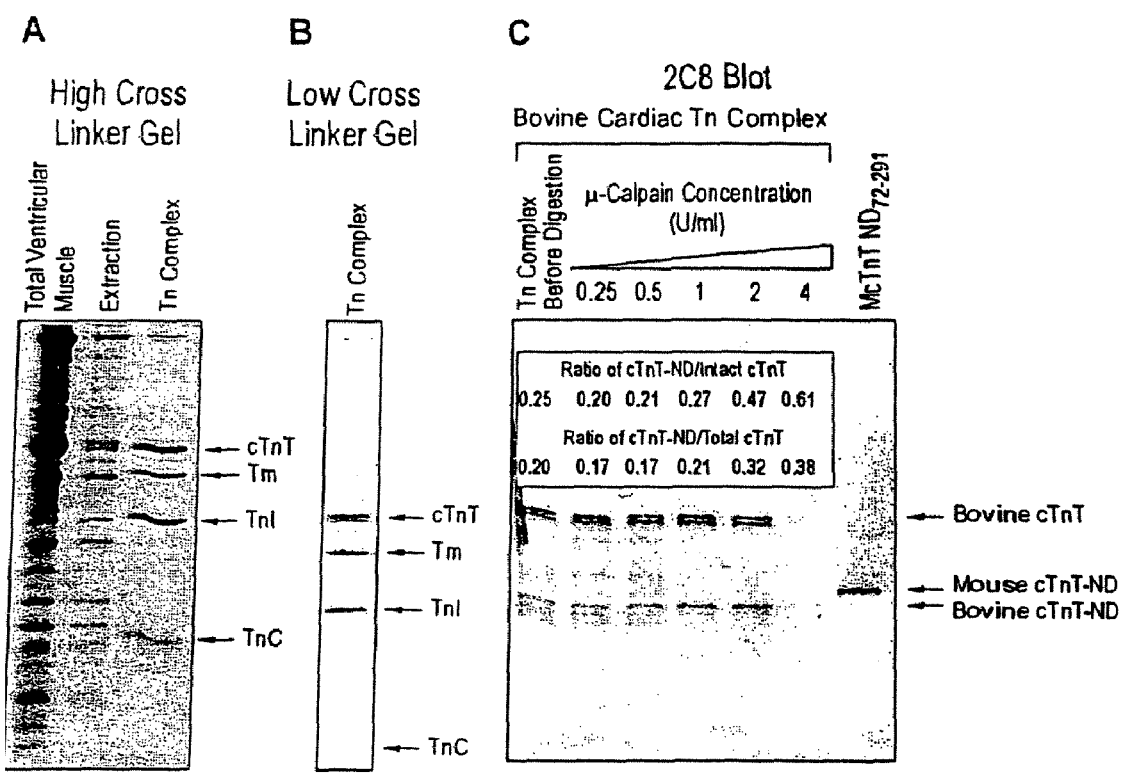
FIG. 10. Isolation and μ-calpain treatment of bovine cardiac troponin complex. A. SDS-PAGE (15% high cross linker gel) showed the effective isolation of troponin (Tn) complex from bovine ventricular muscle homogenate by immunoaffinity chromatography. The TnI-1 mAb affinity column fraction contained 1:1:1 ratio of TnT, TnI and TnC. Some tropomyosin (Tm) was co-isolated with the troponin complex, reflecting the native binding between troponin and tropomyosin in the thin filament. B. 14% Low cross linker SDS-PAGE gel shows the isolated bovine troponin complex contains both of the two adult cTnT isoforms (8), indicating a native state. C. Western blot using anti-cTnT mAb 2C8 showed that μ-calpain treatment of isolated bovine cardiac troponin reproduced a single cTnT-ND fragment from the two NH$_2$-terminal alternatively spliced cTnT isoforms. The insert table shows relative amounts of cTnT-ND produced. It is worth noting that while the troponin structure preserved the TnT core structure against calpain digestion in contrast to that in free cTnT, the protection was less effective than that in intact myofibrils (FIG. 8B). Altogether, the results are consistent with the role of cTnT conformation in determining this selective structural modification under physiological conditions.

Myofibril-associated calpain activity as a rapid regulation of myocardial function. TRITON® X-100 extraction of cardiac muscle fibers induced the production of cTnT-ND, as shown in the following examples, indicating a myofibril-associated proteolytic activity. This effect was independent of the presence or absence of Ca$^{2+}$ in the incubation buffers. Ca$^{2+}$ concentration in living cardiac muscle cells rises periodically to reach a level sufficient for μ-calpain activation. Therefore, the myofilament-associated μ-calpain may have been Ca$^{2+}$-primed in the myocytes before skinning. TRITON® X-100 extraction may have removed an endogenous calpain inhibitor or altered the myofilament conformation to activate the specific cleavage of cTnT. Exogenous calpain inhibitors suppressed the production of cTnT-ND in TRITON® X-100-extracted myofibrils. Consistently, the μ-calpain treatment of cardiac myofibrils reproduced the cTnT-ND$_{72-291}$ fragment. In contrast, μ-calpain treatment of purified cTnT resulted in non-specific degradation, in agreement with that seen in a previous study (36). Although the specific production of cTnT-ND is seen in the μ-calpain treatment of isolated cardiac troponin complex, the protection of the TnT core structure was much less effective than that in the intact myofibril (FIGS. 8 and 10). Therefore, the specific modification of TnT by μ-calpain cleavage is based on the physiological structure of the myofilament. Despite sequence differences, similar NH$_2$-terminal truncation of chicken fast skeletal muscle TnT is produced by endogenous calpain proteolysis in transgenic mouse cardiac muscle (FIG. 11), further supporting the myofilament structure-based specific removal of the TnT NH$_2$-terminal region by calpain cleavage.

Together with the functional effects of removing the NH$_2$-terminal variable region of TnT, the μ-calpain-mediated proteolytic modification of TnT presents a rapid short term mechanism to adjust muscle function under stress conditions. The cleavage occurs within minutes after myocardial ischemia-reperfusion, which is apparently much faster than regulations by altering TnT isoform regulation and/or alternative splicing as that seen in the adaptation of skeletal muscle to unloading (24). Since myofilamental TnT has a half-life of only 4-5 days (55), the functional effect would be transient, suitable for compensation to a usually short-lived ischemia-reperfusion stress event.

Proteolytic modifications of cTnT and cTnI have been shown to have pathological effects on myocardial contractility (28, 56). A caspase-catalyzed fragmentation of cardiac TnT has been found to reduce force production (29). $Ca^{2+}$ overload in cardiomyocytes caused by ischemia-reperfusion has been proposed to activate proteolytic cleavage of cTnI at amino acid 192 to remove the COOH terminus (57). The $cTnI_{1-192}$ fragment reduces the maximal isometric tension of the myocardium and causes a stunning phenotype in the hearts of transgenic mice (28). However the production of $cTnT-ND_{72-291}$ by µ-calpain modification is most likely a functional regulation rather than a detrimental destruction. The presence of low amounts of $cTnT-ND_{72-291}$ in normal cardiac muscle also supports the hypothesis that the myofibril associated µ-calpain activity functions in the physiological regulation of contractility.

Tuning thin filament function in myocardial adaptation under stress conditions. The up-regulation of the $NH_2$-terminal truncated cTnT in ischemia-reperfusion indicates that modification of the thin filament function may play a role in the adaptation of cardiac muscle in stress conditions. By decreasing maximum contractile activation, the deletion of the $NH_2$-terminal domain of cTnT may reduce the work of the cardiac muscle during ischemia-reperfusion as a protective mechanism against permanent damage. This observation suggests that reducing the thin filament $Ca^{2+}$ activation may be a potential target for the prevention or reduction of myocardial infarction damage following an ischemia-reperfusion event. Further studies are needed to investigate this hypothesis.

Posttranslational modification is an effective mechanism to confer transient functional changes in a protein. Posttranslational regulation of cTnT $NH_2$-terminal structure represents an effective immediate responsive mechanism for myocardial adaptation to functional demands and pathological conditions. To date, this level of myocardial regulation has been studied primarily in the context of phosphorylation modifications (25). Restricted proteolytic regulation of cTnT represents a new and different form of regulating protein activity, including the regulation of proteins involved in cardiac muscle adaptation and diseases. These studies will also contribute to the development of new preventative and therapeutic strategies for acute coronary inefficiency. Beyond the commonly recognized protein destruction in myocardial ischemia-reperfusion, the present study laid a foundation for further investigations into the functional significance of cTnT modification in ischemic heart disease.

"Immunoassay" and "antibody" are given the broadest definitions consistent with their respective meanings in the art. An immunoassay may be any relative or absolute measure of binding pair interaction, e.g., antigen-antibody binding, including fluoroimmunoassay, radioimmunoassay, single-antibody or sandwich immunoassay, ELISA or solution-based assays, or any other form of immunoassay known in the art. An "antibody" as used herein may be a protein, polypeptide, peptide or fragment thereof, capable of binding to at least one binding partner, such as a proteinaceous or non-proteinaceous antigen. Antibodies include members of the immunoglobulin superfamily of proteins, of any species, of single- or multiple-chain composition, and variants, analogs, derivatives and fragments of such molecules. Specifically, an "antibody" includes any form of antibody known in the art, including but not limited to, monoclonal and polyclonal antibodies, chimeric antibodies, CDR-grafted antibodies, humanized antibodies, single-chain variable fragments, bi-specific antibodies, diabodies, antibody fusions, and the like.

The following examples provide illustrative embodiments and are not intended to limit either the scope or spirit of the invention.

EXAMPLE 1

Materials and Methods

Cardiac muscle tissues. Fresh bovine cardiac muscle was obtained from local slaughterhouse and kept on ice for about 1.5 hours before being frozen at −80° C. prior to use. Fresh rodent cardiac muscles were obtained from Sprague-Dawley rats, Balb/c mice and C57BL/6 transgenic mice that over-express the embryonic cTnT and/or exon 7-deleted cTnT (20) or chicken fast skeletal muscle TnT (38) in the heart.

Double transgenic mice expressing both embryonic and exon 7 deleted cTnT in the adult heart were produced by crossing between homozygous single transgenic parent bearing each of the transgene alleles. The F1 offspring were verified for the double transgenic genotype by PCR analysis of genomic DNA extracted from tail tissue as described previously (20).

All animal procedures were approved by the Institutional Animal Care and Use Committee and were conducted in accordance with the Guiding Principles in the Care and Use of Animals, as approved by the Council of the American Physiological Society.

Anti-TnT antibodies. A mouse monoclonal antibody (mAb) CT3 was previously developed by immunization with purified bovine cTnT (23). mAb CT3 cross reacts to slow skeletal muscle TnT but not fast skeletal muscle TnT. The distinct mobility of cTnT and slow TnT in SDS-polyacrylamide gel electrophoresis (SDS-PAGE) allows an easy identification of cTnT in Western blots. The CT3 epitope has been mapped in the central region of TnT (23).

A polyclonal rabbit anti-TnT antiserum (RATnT) was previously generated by immunization with purified chicken breast muscle TnT (21). The RATnT antiserum recognizes multiple epitopes on TnT (21). It strongly recognizes the chicken fast skeletal muscle TnT and cross reacts with avian and mammalian cardiac and slow skeletal muscle TnTs.

A mouse mAb (2C8) was previously developed by immunization with human cTnT (39). mAb 2C8 recognizes cardiac, slow, and fast TnTs almost equally in Western blots (39). The 2C8 mAb epitope is located in the central region of TnT.

SDS-PAGE and Western blotting. Ventricular muscle tissues or myocytes were homogenized in Laemmli SDS-PAGE sample buffer containing 2% SDS, heated at 80° C. for 5 min, and clarified by centrifugation. Total protein extracts were resolved by 14% Laemmli gel with an acrylamide:bisacrylamide ratio of 180:1 (low cross linker) or by 15% Laemmli gel with an acrylamide:bisacrylamide ratio of 29:1 (high cross linker). The gels were stained with Coomassie Brilliant Blue R250 to reveal the resolved protein bands. Duplicate gels were electrically blotted to nitrocellulose membranes, as described previously (21). After blocking in Tris-buffered saline (TBS) containing 1% bovine serum albumin (BSA), the membrane was incubated with anti-TnT mAbs CT3, 2C8, or polyclonal antibody RATnT. The membranes were then washed with high stringency using TBS containing 0.5% TRITON® X-100 and 0.05% SDS, incubated with alkaline phosphatase-conjugated anti-mouse IgG or anti-rabbit IgG second antibodies (Sigma), washed again, and developed in 5-bromo-4-chloro-3-indolylphosphate/nitro blue tetrazolium substrate solution, as described previously (21).

Ex vivo ischemia-reperfusion of working rat heart preparations. The Langendorff-Neely working heart preparation was used to perfuse isolated rat hearts and apply in vitro ischemia-reperfusion. As described previously (31), rats were anesthetized with sodium pentobarbital (50 mg/kg body weight, intraperitoneally). The heart was removed and placed in chilled Krebs-Henseliet Buffer (118 mM NaCl, 4.7 mM KCl, 2.25 mM $CaCl_2$, 2.25 mM $MgSO_4$, 1.2 mM $KH_2PO_4$, 0.32 mM EGTA, 11 mM D-glucose and 25 mM $NaHCO_3$) aerated with 95% $O_2$, 5% $CO_2$ (pH 7.4 at 37° C.). The aorta was cannulated with a 16-gauge needle and the apex of the heart placed in 37° C. Krebs-Henseliet Buffer to maintain physiological temperature. The heart was then perfused in a retrograde manner with aerated and warmed Krebs-Henseliet Buffer at a pressure of 70 mmHg for 15 minutes to stabilize the heart. During this period the left atrium was cannulated with a 16-gauge atrial cannula set at a filling pressure of 15 mmHg. The heart was then converted to working mode by switching the tube delivering retrograde perfusion from 70 mmHg to an open column and initiating flow through the atrial cannula. The heart was stabilized in the working mode for 30 minutes at an afterload pressure of 55 mmHg. Following stabilization, the left anterior descending coronary artery was ligated within the middle portion to produce ischemia in an area of the left ventricular free wall. During ischemia the heart was kept at working mode and the cardiac output was monitored for moderate decreases. Following the 20-minute ischemic period, left anterior descending coronary artery perfusion was resumed by removing the ligation, returning the afterload to 55 mmHg for 40 minutes. At the end of the perfusion protocol the heart was removed from the cannula, flash frozen in liquid nitrogen and stored at −80° C. for SDS-gel and Western blot analysis. Control samples of working hearts not subjected to ischemia-reperfusion were otherwise maintained as for the experimental samples and were used after 105 minutes of such maintenance.

Murine ex vivo working hearts subjected to conditions modeling large myocardial infarctions were treated in a like manner to those ex vivo working hearts described as being subjected to conditions modeling small myocardial infarctions, except that with the former hearts, the left anterior descending coronary artery was ligated near its root to result in ischemia in a large area of the left ventricular free wall. The large infarct was evident by the significant decrease in cardiac out put during the ischemia treatment.

As a control of simple myocardial ischemia, eight-week-old C57/BL6 mice were euthanized by cervical dislocation and the bodies placed at room temperature (22° C.) in a sealed plastic bag to prevent dehydration. The hearts were removed at 0, 2, 4, and 8 hours post-mortem and homogenized in SDS-PAGE sample buffer for SDS-gel and Western blot analysis to determine degradation of cTnT resulting from postmortem ischemia.

Ischemia-reperfusion treatment of mouse cardiomyocytes. To induce ischemia-reperfusion damage in cardiac myocytes, mouse ventricular myocytes were isolated in low oxygen buffer followed by incubation in oxygenated buffer. Similar to that previously described (20), cardiomyocytes were isolated from transgenic mouse hearts over expressing embryonic cTnT or exon 7-deleted cTnT by retrograde perfusion with $Ca^{2+}$ free Joklik solution containing 1% BSA and collagenase without oxygenation. Following isolation, the cardiac myocytes were incubated at room temperature without oxygenation for 30 minutes before initiating re-oxygenation and returning $Ca^{2+}$ to 1.25 mM stepwise over a 35 minute period. Once $Ca^{2+}$ had been restored oxygenation was continued and the myocytes incubated at room temperature for an additional 30 minutes when the myocytes were collected by centrifugation, washed in TBS and lysed in SDS-Sample Buffer for Western blot analysis.

Isolation of cTnT fragment from $NH_2$-terminal sequencing. To investigate the primary structure of the ischemia-reperfusion-produced cTnT fragment, mouse cardiac myocytes treated with ischemia-reperfusion were homogenized in TBS and fractionated by ammonium sulfate precipitation. The 30-50% saturation fraction was dialyzed against 0.1 mM EDTA for three changes at 4° C. After dialysis, the precipitated material was collected by centrifugation at 25,000 g, 4° C., for 30 min. The cTnT fragment in the low salt precipitate was further purified by a two step preparative SDS-PAGE procedure. The sample was first resolved by electrophoresis on high cross linker gel (12% Laemmli gel with an acrylamide-to-bisacrylamide ratio of 29:1). The resulting gel was stained with Coomassie Brilliant Blue R-250 and the band containing the cTnT fragment as determined by parallel Western blot using the CT3 mAb was cut out. The protein contents were recovered from the gel slices by electrophoresis elution in SDS-gel running buffer. After dialysis against 0.1% formic acid and concentrated by lyophilization, the protein sample was re-dissolved in SDS-gel sample buffer and further resolved by electrophoresis on low cross linker SDS-PAGE (14% Laemmli gel with an acrylamide-to-bisacrylamide ratio of 180:1). The resulting gel was electronically transferred to PVDF membrane and stained with Amido Black to visualize the protein bands. A parallel strip of the membrane was subjected to Western blot using the anti-cTnT mAb CT3 as described above. The CT3 positive band of the Western blot was aligned to the Amido Black stained membrane and the corresponding band was excised for $NH_2$-terminal sequencing at the Biotechnology Resource Laboratory Protein Sequencing and Peptide Synthesis Facility, Medical University of South Carolina, Charleston, S.C.

Expression of TnT and reconstructed TnT fragment in *E. coli*. Intact mouse cTnT (TnT4) was expressed in *E. coli* culture. The construction of pAED4 expression plasmid from a cloned cDNA (40), large scale expression, and purified were done as described previously for the turkey cTnT (19).

Figure 4:
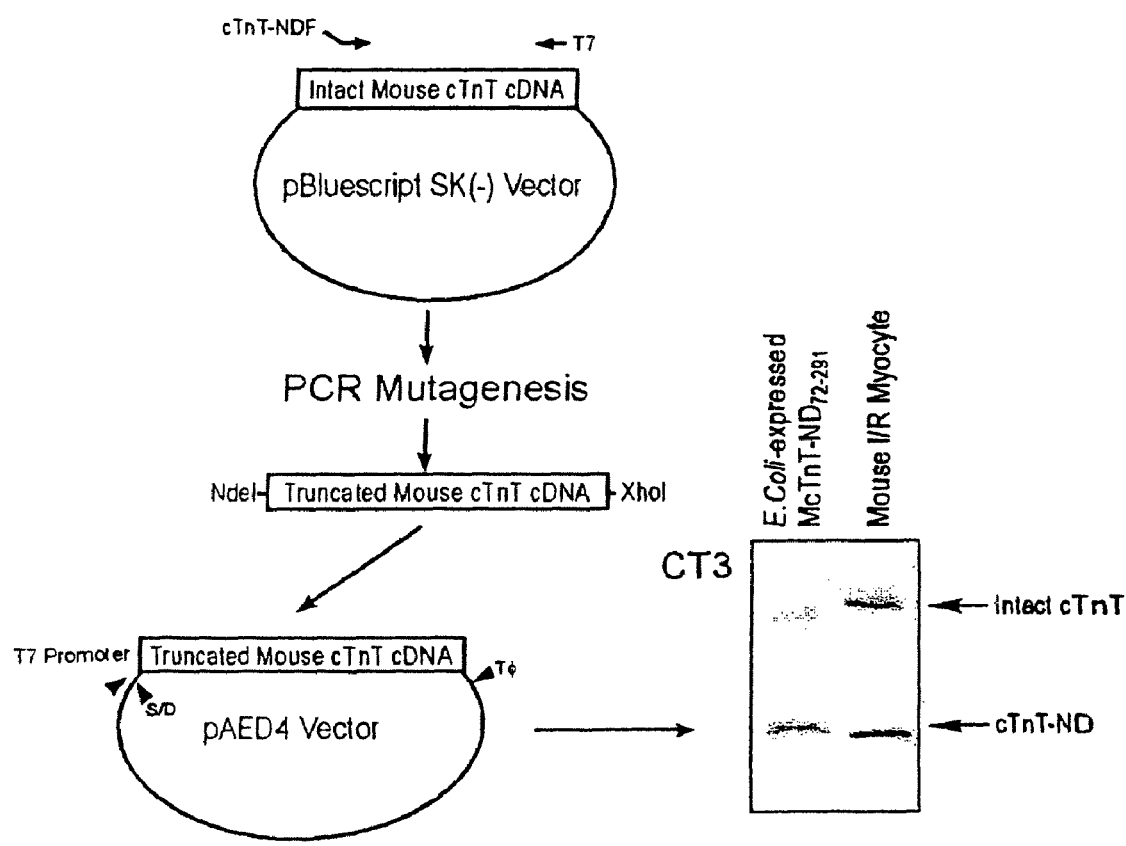
FIG. 4. Bacterial expression of the reconstructed cTnT fragment. 5'-truncated mouse cTnT cDNA was constructed according to the $NH_2$-terminal truncation site for protein expression in E. coli. The cTnT fragment expressed from the truncated cDNA shows a size identical to that of the cTnT fragment produced in ischemia-reperfused cardiac muscle (the slightly slower gel mobility seen in the blot may be due to the addition of an $NH_2$-terminal Met in the expression construct), indicating that the $NH_2$-terminal truncation is the only primary structure modification.

A cDNA template encoding an $NH_2$-terminal deleted mouse cTnT was engineered by polymerase chain reaction (PCR) mutagenesis to create a translational initiation codon prior to the cleavage site ($Leu_{72}$) as determined by $NH_2$-terminal sequencing. As shown in FIG. 4, cloned adult mouse cTnT cDNA in pBluescript SK(−) plasmid (40) was used as template and PCR was carried out using a custom designed 5' oligonucleotide primer that contained a NdeI restriction site (underlined), a translational initiation codon ATG, and the region complementary to the coding sequence for amino acid 72-77 (McTnT-NDF: 5'-AGCCC CATATGCTCTTCATGCCCAACTT-3'; SEQ ID NO:1). The PCR product was modified at the 5' and 3' ends by NdeI and XhoI cuts and cloned into the pAED4 expression plasmid (41). The cDNA insert was sequenced by dideoxy chain termination method to verify the construction and sequence authenticity.

The truncated mouse cTnT cDNA was expressed by transformation of BL21(DE3)pLyseS *E. coli* cells with the expression plasmid. Freshly transformed bacterial cells were cultured in 2×TY rich liquid media (16 g/L Tryptone, 10 g/L yeast extract, 5 g/L NaCl, 1.32 g/L $Na_2HPO_4$, pH 7.3) containing 100 mg/L ampicillin and 25 mg/L chloramphenicol at 37° C. with vigorous shaking and induced with 0.4 mM isopropyl-1-thiol-β-D-galactoside at mid-log phase. After three additional hours of culture, the bacterial cells were harvested by centrifugation at 4° C. The bacterial pellet was suspended in 2.5 mM EDTA, 50 mM tris-HCl, pH 8.0 and lysed by three passes through a French Press cell. The bacterial lysate was clarified by centrifugation and precipitated with ammonium sulfate to obtain the 0-35% saturation fraction. Following dialysis against 0.1 mM EDTA containing 6 mM β-mercaptoethanol, the 0-35% fraction was brought to 6 M urea, 0.1 mM EDTA, 6 mM β-mercaptoethanol, 20 mM sodium acetate, pH 6.0 and fractionated by chromatography on a CM52 cation-exchange column equilibrated in the same buffer. The column was eluted by a 0-500 mM linear KCl gradient and the protein peaks analyzed by SDS-PAGE. Fractions containing the $NH_2$-terminal truncated TnT were further purified by G75 gel filtration chromatography in 6 M urea, 500 mM KCl, 0.1 mM EDTA, 6 mM β-mercaptoethanol, 10 mM imidazole-HCl, pH 7.0. Protein peaks were analyzed by SDS-PAGE and the fractions containing pure $NH_2$-terminal truncated TnT were dialyzed against 0.1% formic acid and lyophilized. All purification steps were carried out at 4° C.

According to the $NH_2$-terminal truncation site (between Thr45 and Ala46) reported in rabbit fast TnT (32), an expression vector encoding $NH_2$-terminal truncated mouse fast skeletal muscle TnT was reconstructed by similar procedures and expressed in *E. coli* as described above.

TRITON® X-100 extraction of ventricular muscle strips. In an ice container, ventricular muscle was cut with a sharp razor blade into fine pieces approximately the size of isolated trabeculae. The muscle strips were washed in relaxing solution containing 0.1 KCl, 2 mM $MgCl_2$, 2 mM EGTA, 10 mM Tris, 0.5 mM DTT, 0.1 mM PMSF and 2 mM $Na_4P_2O_7$. After centrifugation at 2,800×g at 4° C. for 15 min, the pellet was skinned in relaxing solution plus 0.5% (w/w) TRITON® X-100 at 4° C. with rotation for 10 min. After centrifugation at 14,000×g at 4° C. for 20 min, the pellet was suspended in relaxing solution without TRITON® X-100 and incubated at 37° C. with rotation. Samples were collected at a series of time points for SDS-PAGE and Western blotting to examine the modifications of cTnT and other myofibrillar proteins.

Calpain inhibition. To test whether endogenous calpain in the cardiac muscle contributes to TnT $NH_2$-terminal modification, several different calpain inhibitors were applied to the TRITON® X-100 extraction procedure. It has been reported that μ-calpain proteolytic activity is strongly inhibited by the application of an oxidant, e.g. 100 μM of hydrogen peroxide (42). TRITON® X-100 treatment of mouse ventricular muscle strips was carried out as above in the presence or absence of 100 μM hydrogen peroxide and the effect on cTnT modification was examined by Western blotting.

The effects of two cell membrane-permissible nonpeptide calpain inhibitors, PD 150606 and PD 151746 (Calbiochem), were also tested. PD150606 exhibits similar apparent inhibition constants against μ-calpain ($K_i$ 0.21±0.01 μM) and m-calpain ($K_i$ 0.37±0.03 μM), whereas PD151746 has a 20-fold selectivity for μ-calpain ($K_i$ 0.26±0.03 μM) over m-calpain ($K_i$ 5.33±0.77 μM) (43). PD 150606 and PD 151745 were separately added to the relaxing solution before TRITON® X-100 treatment and incubated with the minced ventricular muscle at 4° C. for 10 minutes to allow the inhibitor to penetrate cell membrane and bind to calpain. After TRITON® X-100 extraction, samples were collected for SDS-PAGE and Western blotting to examine the effect on cTnT modification.

Muscle protein purifications. Bovine cTnT was purified from left ventricular muscle as previously described (8). Bovine cardiac TnI was purified from ventricular muscle as described previously (19). Rabbit α-tropomyosin was purified from ventricular muscle as described previously (44).

Preparation of cardiac myofibrils. Cardiac myofibrils were prepared from ventricular muscle according to the method described previously (45) with modifications. All steps were conducted at 4° C. The ventricular muscle was pulverized in a food blender in 10 volumes (w/v) of the above relaxing buffer. The homogenization was passed through two layers of cheesecloth, and centrifuged at 2,000×g for 15 min. After three washes using the relaxing buffer without $Na_4P_2O_7$, the pellet was suspended in the washing buffer containing 0.5% (w/w) TRITON® X-100 for 10 minutes with occasional stiffing. Four more washes were performed to remove Triton X-100. The myofibrils were stored −20° C. in the washing buffer containing 50% glycerol until use.

Isolation of troponin complex from cardiac muscle. Cardiac troponin complex was isolated by immunoaffinity chromatography using a mouse mAb (TnI-1) against the COOH-terminus of TnI (46). The TnI-1 epitope is exposed in the troponin complex and can be used as a handle to isolate the troponin complex from muscle homogenates (30). The TnI-1mAb (IgG1) was purified from hybridoma ascites fluid using a Protein G coupled to an agarose-based medium (Protein G-SEPHAROSE®) (Amersham Pharmacia Biotech) affinity column and coupled to CNBr-activated SEPHAROSE® 4B (Amersham Pharmacia Biotech) according to the manufacturer's protocols. Bovine left ventricular muscle was minced into small pieces and extracted by 20 volumes (w/v) of Guba-Straub solution containing 300 mM KCl, 100 mM $K_2HPO_4$, 50 mM $KH_2PO_4$, 2.5 mM $MgCl_2$, 1 mM EGTA, and 0.1 mM phenylmethylsulfonyl fluoride (PMSF), pH 6.5, on ice for 15 min. After centrifugation at 16,000×g at 4° C. for 20 min, the supernatant containing mainly myosin was removed. The pellet was extracted in 20 volumes (w/v) of 1 M KCl, 10 mM Tris-HCl, pH 8.0, 0.1 mM PMSF by stiffing on ice for 30 min. After centrifugation as above, the extract was diluted 5-fold in TBS and loaded on the TnI-1 mAb affinity column equilibrated in TBS. The column was washed with TBS, and the proteins bound to the TnI-1 affinity column were eluted with 0 mM glycine-HCl, pH 2.7. Fractions (0.3 ml) were collected into tubes containing 0.05 ml of neutralizing buffer containing 1 M Tris-HCl, 1.5 M NaCl, 1 mM EDTA, pH 8.0. The fractions were analyzed by SDS-PAGE and Western blotting as described above to identify the troponin peak. The fractions containing the three troponin subunits were examined by SEPHAROSE® G-75 column (Amersham Pharmacia Biotech) under non-denaturing conditions to verify their formation of troponin complex.

Mu-Calpain treatment of cTnT. Purified bovine cTnT and troponin complex were incubated at 37° C. in 50 mM sodium borate buffer, pH 7.5, containing 3 mM $MgCl_2$, 1.25 mM $CaCl_2$ and various concentrations (0.25 U/ml to 4 U/ml) of μ-calpain (Calbiochem). After 30 minutes incubation, the reaction was stopped by adding 3× SDS-PAGE sample buffer and heating at 80° C. for 5 min. The samples were analyzed by SDS-PAGE and Western blotting as described above.

The isolated bovine cardiac myofibrils were centrifuged at 3,000×g for 15 minutes to remove glycerol. The pellet was suspended in 50 mM sodium borate buffer, pH 7.5, containing 3 mM $MgCl_2$, and 1.25 mM $CaCl_2$. The calpain treatment conditions were same as that on purified proteins except for the use of higher concentrations of μ-calpain (5 U/ml to 20 U/ml). The effects on myofilament proteins were examined by SDS-PAGE and mAb CT3 Western blotting as above.

Protein binding assays. Enzyme-linked immunosorbant assay (ELISA) solid phase protein binding experiments (21) were performed to investigate the interactions of the $NH_2$-terminal truncated cTnT with TnI and tropomyosin. Purified intact and $NH_2$-terminal truncated mouse cTnT or BSA control were dissolved at 5 μg/mL in Buffer A (0.1 M KCl, 3 mM MgCl$_2$, 20 mM PIPES, pH 7.5) and coated onto 96-well microtiter plates by incubation at 4° C. overnight. After washes with Buffer T (Buffer A containing 0.05% polyoxyethylene 20 (TWEEN®20)) at pH 7.5 to remove the unbound protein, the plates were blocked with Buffer T at pH 7.0 or 6.2 containing 1% BSA. The immobilized cTnT was incubated with serial dilutions of bovine cardiac TnI or rabbit α-tropomyosin in Buffer T (at the blocking pH) containing 0.1% BSA at room temperature for 2 hours. After one wash with Buffer T of the blocking pH and two washes with Buffer T at pH 7.0, the bound TnI or tropomyosin was quantified via incubation at pH 7.0 and room temperature for 1 hour with the anti-TnI mAb TnI-1 (46) or an anti-tropomyosin mAb CH1 (47), respectively. The plates were then processed by a standard ELISA procedure, including pH 7.0 Buffer T washes, horse radish peroxidase-conjugated anti-mouse immunoglobulin second antibody (Sigma) incubation, and H$_2$O$_2$/2,2'-azinobis-(3-ethylbenzthiazolinesulfonic acid) substrate reaction (21). $A_{405\,nm}$ of each assay well was recorded at a series of time points by an automated microtiter plate reader (Bio-Rad Benchmark). The $A_{405\,nm}$ values in the linear course of the color development were used to plot the protein binding affinity curves. All experiments were done in triplicate.

Data analysis. The DNA and protein sequence analyses were done using computer programs from DNAStar. Statistical analysis of the SDS-gel and Western blot densitometry and the protein binding data was done by Student t test. All values are presented as mean±SD.

EXAMPLE 2

A cTnT fragment produced in myocardial ischemia-reperfusion. Western blots using mAb CT3 recognizing cardiac and slow TnT (23) detected a significant amount of a low $M_r$ protein band in ischemia-reperfused rat heart (FIG. 1A). This band has a significantly lower apparent molecular weight than that of the slow skeletal muscle TnT or any known alternatively spliced cTnT isoforms. This band is also recognized by several other anti-cTnT mAbs as well as the rabbit polyclonal anti-TnT antibody RATnT, indicating that it is a modified TnT protein. Considering the facts that slow and fast skeletal muscle TnT are not expressed in postnatal cardiac muscles (48), this low $M_r$ TnT is likely a proteolytic fragment of cTnT.

The cTnT fragment is present in normal cardiac muscle although at very low levels (FIG. 6B), suggesting a physiological relevance. Simple postmortal ischemia for up to 8 hours did not increase the cTnT fragmentation (FIG. 1B). There was no detectable change in the cTnT fragment in the rat heart after one-hour in vitro perfusion, demonstrating a correlation to the ischemia-reperfusion stress conditions.

EXAMPLE 3

Figure 2:
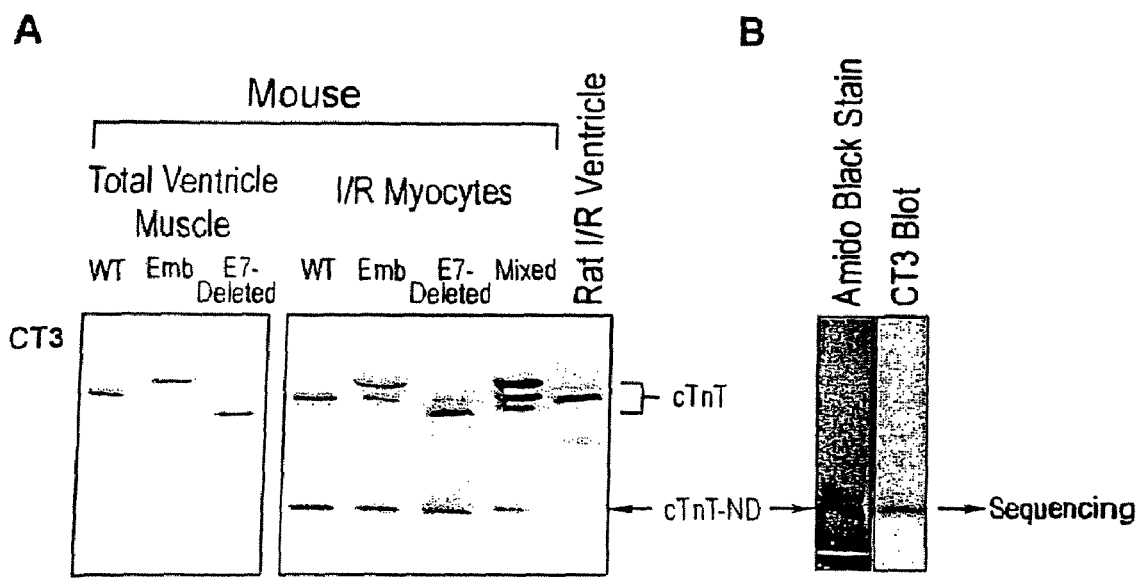
FIG. 2. Isolation of the cTnT fragment from ischemia-reperfused mouse cardiomyocytes to determine the $NH_2$-terminal sequence. A. The cTnT fragment was produced in isolated mouse cardiomyocytes that had undergone ischemia-reperfusion conditions. Samples from transgenic mouse hearts expressing embryonic cTnT and/or exon 7-deleted cTnT that differ from the endogenous adult cTnT in the $NH_2$-terminal region (FIG. 5) showed a cTnT fragment identical in size to that produced in the wild type adult mouse cardiomyocytes, indicating that a removal of the $NH_2$-terminal variable region produces the cTnT fragment. B. The cTnT fragment band isolated from low cross linker preparative SDS-PAGE gel (see Materials and Methods) was resolved on a high cross linker SDS-gel and transferred to PVDF membrane for N-terminal sequencing. Amido Black staining revealed the yield of the cTnT fragment that is confirmed by mAb CT3 Western blot.

The cTnT fragment is produced by a restricted NH$_2$-terminal truncation. Suggesting an NH$_2$-terminal deletion that produces the cTnT fragment, ischemia-reperfusion treatment of transgenic mouse cardiomyocytes expressing embryonic or exon 7-deleted cTnT that differ from the wild type cTnT only in the length of the NH$_2$-terminal variable region produced cTnT fragments with identical size (FIG. 2A).

The low molecular weight cTnT fragment was isolated from ischemia-reperfused mouse cardiomyocytes for NH$_2$-terminal sequencing. FIG. 2B shows the enrichment of the cTnT fragment by preparative SDS-PAGE. The NH$_2$-terminal sequencing result revealed that this low molecular weight TnT protein is indeed a cTnT fragment with a deletion of the NH$_2$-terminal amino acids 1-71 (FIG. 3).

To investigate the integrity of the COOH-terminus in the cTnT fragment, the NH$_2$-terminal truncation was constructed in mouse cTnT by generating a 5'-truncated mouse cTnT cDNA (FIG. 4). Expression of the truncated cDNA in E. coli produced a cTnT protein with a size identical to that of the cTnT fragment produced in ischemia-reperfused cardiac muscle. The results demonstrate that there was no COOH-terminal deletion in this cTnT fragment.

The NH$_2$-terminal truncation site (Arg$_{71}$-Leu$_{72}$) is not at an exon boundary and, therefore, the cTnT-ND$_{72-291}$ fragment is not generated by alternative RNA splicing but by proteolytic cleavage. Sequence alignment (FIG. 3) demonstrates that the cleavage site is different from the previously reported caspase cleavage site in cTnT (the rat 25-kDa cTnT) under ischemia-reperfusion conditions (29).

EXAMPLE 4

Figure 5:
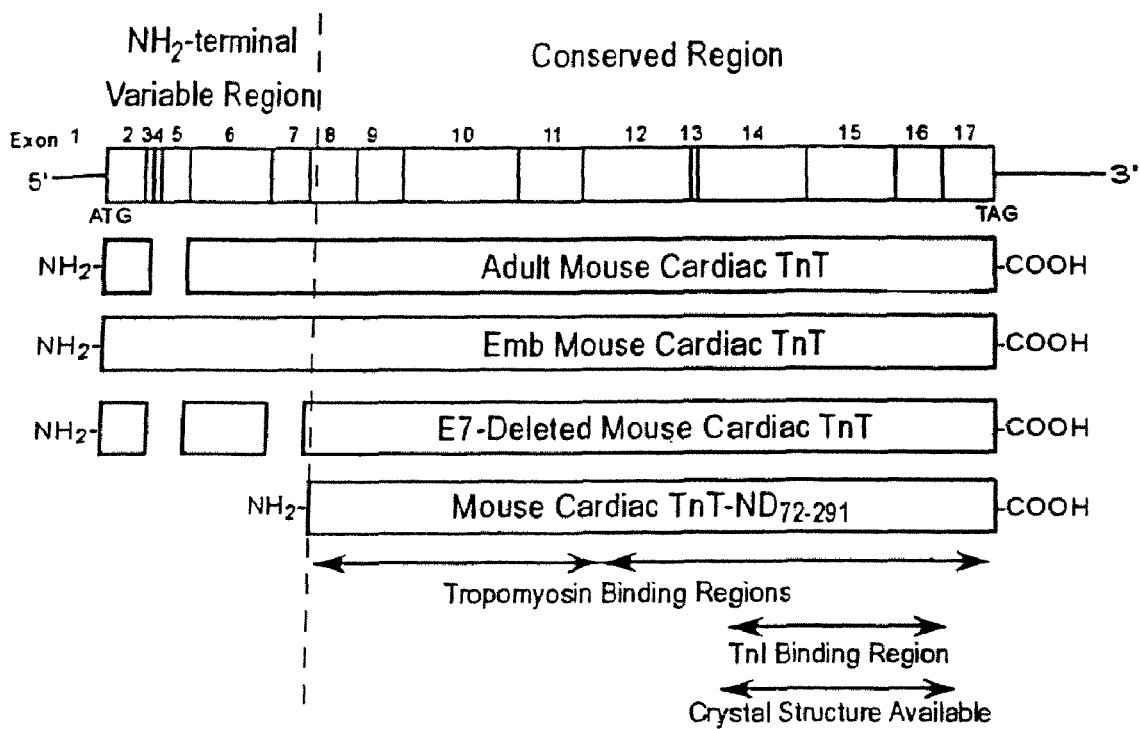
FIG. 5. Structural comparison of the $NH_2$-truncated cTnT with cTnT splicing variants. The $NH_2$-terminal and adjacent regions of intact wild type adult mouse cTnT and two alternatively spliced variants are aligned together with the $NH_2$-terminal truncated cTnT. The $NH_2$-terminal truncation specifically removes of the entire variable region that is alternatively spliced to produce the adult mouse cardiac TnT (Adult cTnT-4, exclusion of exons 4 and 5), embryonic isoform (Emb cTnT-1, contains all the exons), and E7-deleted mouse cardiac TnT (E7-deleted TnT, exclusion of exons 4, 5 and exon 7). The central and COOH-terminal conserved regions of TnT contain the core functional structure that binds other thin filament regulatory proteins, TnI, TnC and tropomyosin (Tm). These protein binding sites and the portion of TnT with X-ray crystallography structure available are outlined. The $NH_2$-terminal truncated cardiac ($McTnT-ND_{72-291}$) retains the integrity of the conserved core structure, implying a functional role in myocardial ischemia-reperfusion.

The restricted NH$_2$-terminal truncation of cTnT preserves the core functional structure of TnT. FIG. 5 compares the NH$_2$-terminal truncated cTnT with several intact cTnT variants and demonstrates that the NH$_2$-terminal cleavage of the cTnT polypeptide chain specifically removes the entirely hypervariable region encoded by exons 2 to 7. The central and COOH-terminal conserved regions that contain binding sites for other thin filament regulatory proteins, TnI, TnC and tropomyosin are preserved in this proteolytic modification. The integrity of the conserved core structure of TnT in the NH$_2$-terminal truncated cTnT (cTnT-ND$_{72-291}$) implies a functional effect in myocardial ischemia-reperfusion. This notion is consistent with the fact that cTnT-ND$_{72-291}$ was retained in the isolated cardiac myofibrils with a proportion identical to that in the total muscle extract, indicating its full ability to incorporate into the myofilament (FIG. 6A).

EXAMPLE 5

Figure 6:
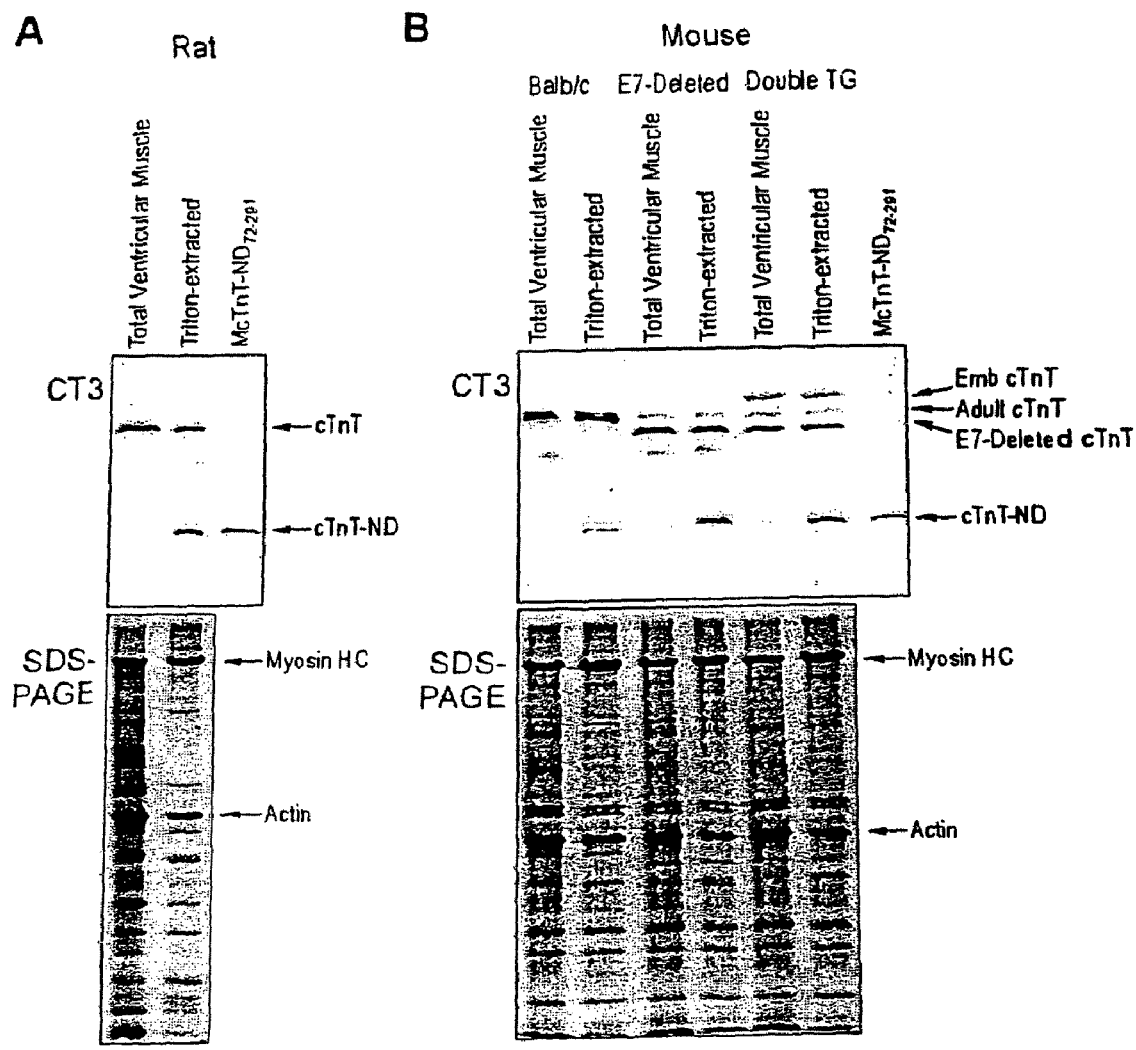
FIG. 6. 4-(1,1,3,3-Tetramethylbutyl)phenyl-polyethylene glycol) (TRITON® X-100) extraction promotes the production of the $NH_2$-terminal truncated cTnT. Rat (A) and mouse (B) ventricular muscle strips before and after TRITON® X-100 extraction were examined by SDS-PAGE and Western blot using anti-TnT mAb CT3. The results revealed that TRITON® X-100 extraction induced the production of a specific cTnT fragment in both rat and mouse cardiac muscle samples. In the mouse model, adult, exon 7 (E7)-deleted and embryonic (Emb) cTnTs with different $NH_2$-terminal structures produced a single fragment that has the same size as the reconstructed $McTnT-ND_{72-291}$ protein, consistent with a selective $NH_2$-terminal truncation. The production of $NH_2$-terminal truncated cTnT (cTnT-ND) by TRITON® X-100 extraction suggests the role of activating of a myofibril-associated protease. The accompanying SDS-PAGE showed comparable amounts of protein loading normalized to that of actin and that other major myofibril proteins were not affected by the TRITON® X-100 treatment.

TRITON® X-100 extraction of cardiac muscle activates an endogenous proteolytic activity that produces the NH$_2$-terminal truncated cardiac TnT. Western blotting using mAb CT3 demonstrated that TRITON® X-100 treatment of rat and mouse cardiac muscle strips reproduced the specific cTnT-ND fragment (FIG. 6). In the mouse model, TRITON® X-100 extraction of transgenic cardiac muscle containing wild type adult, embryonic and exon 7-deleted cTnTs that are different in the NH$_2$-terminal region produced a single fragment with the same size as that of McTnT-ND$_{72-291}$. This was most clearly shown in the double transgenic mouse heart that simultaneously expresses all of the three cTnT variants (FIG. 6B). This result indicates that the cTnT fragment produced by TRITON® X-100 extraction is the same as the identified NH$_2$-terminal truncated cTnT-ND$_{72-291}$. TRITON® X-100 treatment is known to remove lipid contents from the muscle fiber without disruption of the myofibril structure. SDS-PAGE in FIG. 6 showed that other major myofibril proteins were not affected by TRITON® X-100 treatment. The TRITON® X-100 treatment may have activated a myofibril-associated protease that is responsible for the specific production of cTnT-ND$_{72-291}$ under stress conditions.

EXAMPLE 6

The production of NH$_2$-terminal truncated cTnT by myofibril associated proteolytic activity is suppressed by calpain inhibitors. Calpain has been reported to cleave cTnT (36).

Figure 7:
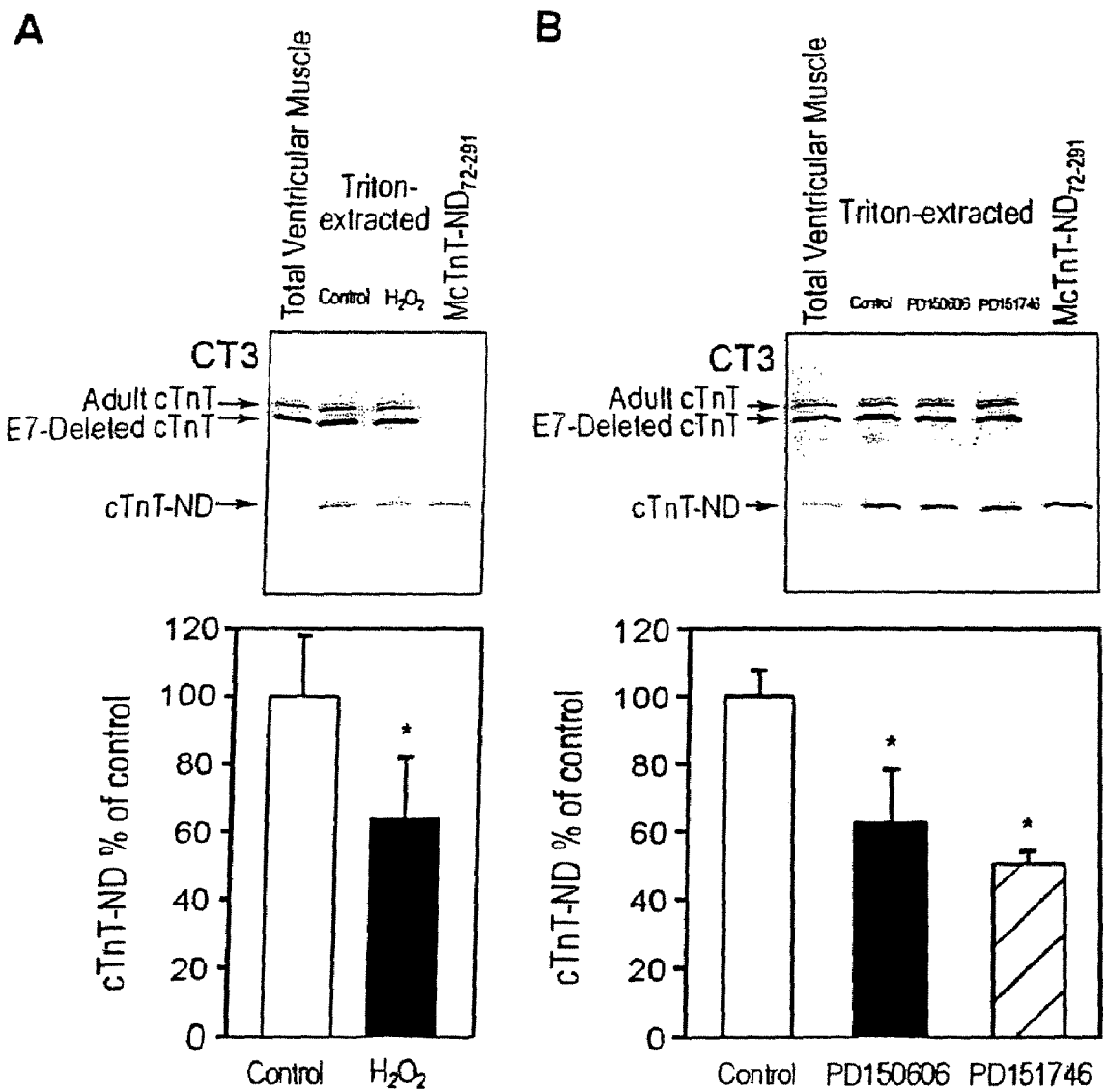
FIG. 7. Calpain inhibitors reduce the production of $NH_2$-terminal truncated cTnT by myofibril associated proteolytic activity. A. Western blots were used to examine TRITON® X-100 extracted exon 7 (E7)-deleted transgenic mouse ventricular muscle strips in the absence or presence of 100 μM hydrogen peroxide. Densitometric analysis showed that cTnT-ND production was reduced to 65% in the presence of hydrogen peroxide (*, P<0.01), indicating an effect of inhibiting the activity of μ-calpain (42). B. Calpain specific inhibitors, PD150606 and PD151746, also decreased the productions of cTnT-ND TRITON® X-100 extracted mouse cardiac muscle strips (to 63% and 50%, respectively, P<0.01), further supporting the role of myofibril associated μ-calpain in the production of cTnT-ND. Data are shown as mean ±S.D. The results were summarized from the three individual experiments.

Therefore, the effects of calpain inhibitors on the myofilament-associated endogenous proteolytic activity were tested. Western blot examination showed that the presence of 100 µM hydrogen peroxide decreased the TRITON® X-100-induced production of cTnT-ND$_{72-291}$ in mouse ventricular muscle strips (FIG. 7A). The addition of 100 µM of hydrogen peroxide resulted in an approximately 35% decrease in cTnT-ND$_{72-291}$. Hydrogen peroxide is known to inhibit the proteolytic activity of µ-calpain (42). Therefore, this result suggests that cardiac myofilament associated µ-calapin may be responsible for the production of cTnT-ND$_{72-291}$ fragment during ischemia-reperfusion.

Consistently, calpain specific inhibitors, PD150606 and PD151746, also decreased the productions of cTnT-ND$_{72-291}$ in TRITON® X-100 extracted mouse cardiac muscle strips (FIG. 7B). These specific calpain inhibitors resulted in an approximately 37% and an approximately 50% decreases in cTnT-ND$_{72-291}$ production, respectively, further supporting the role of myofibril associated µ-calpain.

EXAMPLE 7

µ-Calpain treatment of myofibrils reproduced the NH$_2$-terminal truncated cTnT fragment. The results in FIG. 8A demonstrate that µ-calpain treatment of purified bovine cTnT effectively decreased the level of intact cTnT in a dose-dependent manner, consistent with that observed in a previous study (36). However, no specific cTnT fragment was produced at a significant amount from µ-calpain treatment of purified cTnT, demonstrating a non-specific degradation effect.

On the other hand, µ-calpain treatment of bovine cardiac myofibril effectively reproduced the cTnT-ND$_{72-291}$ fragment (FIG. 8B). SDS-PAGE and the gel densitometry plots (FIG. 8B) further showed that other major myofibrillar proteins, including myosin, actin and tropomyosin, were not significantly affected by the µ-calpain treatment. This result supports the observation that the production of cTnT-ND$_{72-291}$ during myocardial ischemia-reperfusion is by endogenous µ-calpain cleavage. In contrast to the non-specific degradation of purified cTnT by µ-calpain, the specific re-production of cTnT-ND$_{72-291}$ by µ-calpain treatment of cardiac myofibrils demonstrates that this posttranslational modification of cTnT structure is dependent on the physiological structure of the myofilament, consistent with a physiological relevance.

Figure 9:
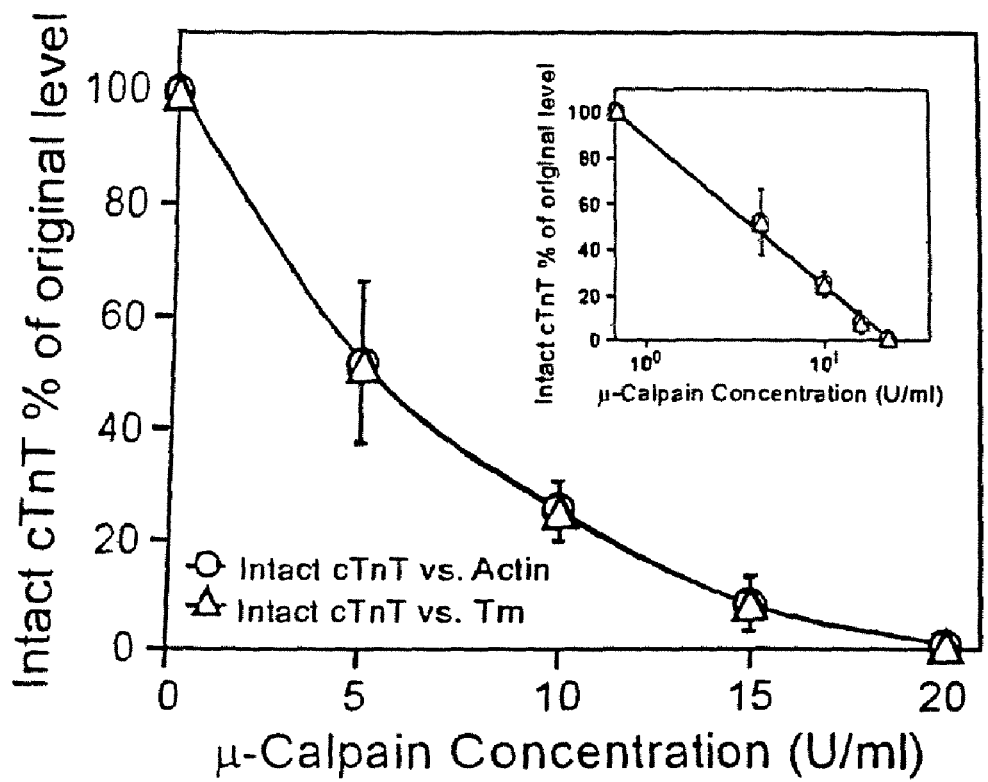
FIG. 9. μ-Calpain production of NH$_2$-terminal truncated cTnT suggests a restricted proteolytic modification. Densitometry analysis of multiple copies of mAb CT3 Western blots (FIG. 8) determined the relative amounts of intact and NH$_2$-terminal truncated cTnT in μ-calpain treated bovine cardiac myofibrils. The results show that intact cTnT decreased from 100% to 1.5% when the concentration of μ-calpain increased from 0 U/ml to 20 U/ml (A), while the amount of the NH$_2$-terminal truncated cardiac TnT, cTnT ND, increased from 0% to 98% of the total cTnT (truncated plus intact) (B). The reverse exponential dose responses of the cleavage of intact cTnT as shown by the semi-log plot inserts and the specific production of the NH$_2$-terminal truncated cTnT by μ-calpain treatment suggest a selective and restricted proteolytic modification.
Figure 9:
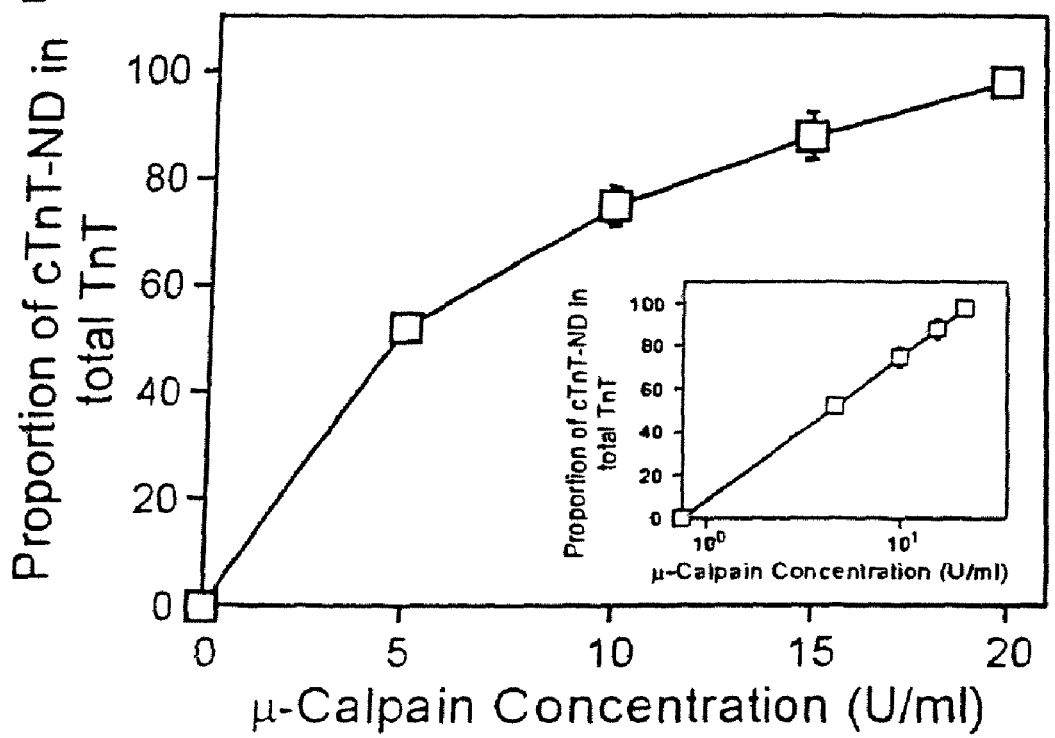

Quantitative densitometry analysis of the Western blots shows that the µ-calpain modification of cTnT in bovine cardiac myofibril had a non-linear (reverse exponential) dose relationship (FIG. 9). The sensitive responses to the initial increasing concentrations of µ-calpain imply a preferred selective cleavage of cTnT in the myofibrils. On the other hand, the reaching of a plateau at the higher concentration of µ-calpain suggests a restricted proteolytic modification.

Mu-Calpain treatment of isolated bovine cardiac troponin complex also showed a selective cleavage of the NH$_2$-terminal domain of TnT (FIG. 10). The difference between free TnT and troponin complex in µ-calpain proteolysis is consistent with the determining role of the substrate structural conformation. Nonetheless, the higher sensitivity and less effective preservation of the TnT core structure seen in the µ-calpain treatment of isolated troponin complex than that of intact myofibrils (FIG. 8B) suggest that this selective structural modification of TnT is most effective under physiological conditions.

EXAMPLE 8

Figure 11:
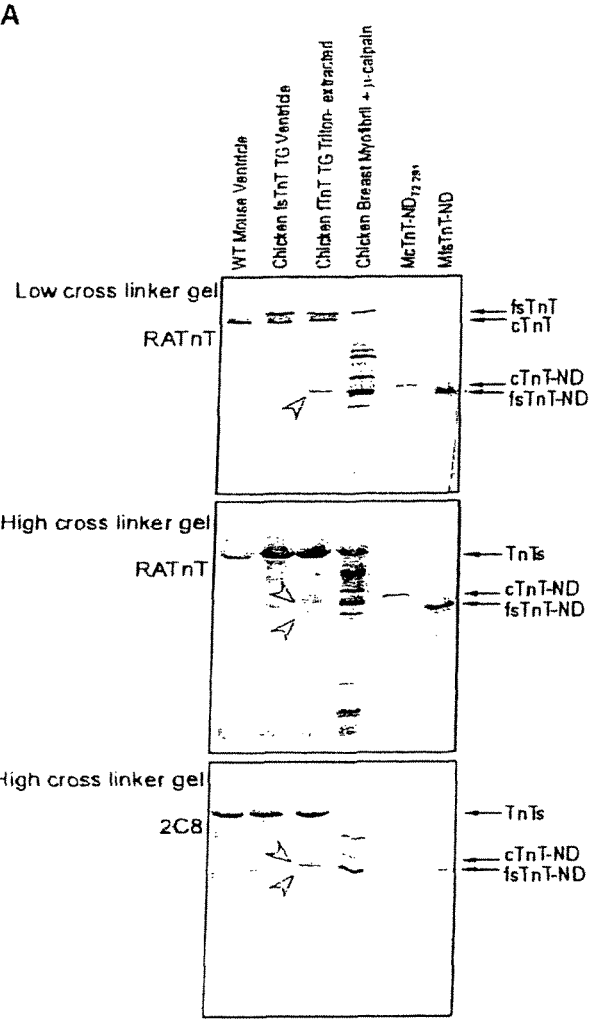
FIG. 11. Similar NH$_2$-terminal truncation of cardiac and fast skeletal muscle TnT by μ-calpain modification. A. Western blot using polyclonal antibody RATnT raised against chicken fast TnT and mAb 2C8 recognizing both cardiac and fast TnTs detected TnT-ND fragments (indicated by the arrowheads) in TRITON® X-100-treated transgenic mouse cardiac muscle strips containing endogenous cTnT and exogenous chicken fast skeletal muscle TnT (fsTnT) (38). While the blot using low cross linker SDS-gel (upper panel) showed only one TnT fragment band, the blot using high cross linker SDS-gel resolved two TnT fragments with distinct immunoreactivities to RATnT and 2C8 antibodies, indicating their cTnT and fast TnT origins. μ-Calpain-treated chicken breast muscle myofibrils and reconstructed mouse cTnT-ND and mouse fast TnT-ND was used as controls. B. Aligned amino acid sequences of the NH$_2$-terminal regions of mouse cardiac and chicken fast skeletal muscle TnTs flanking the truncation sites are shown. The predicted molecular weights of the NH$_2$-terminal truncated cTnT and fast TnT proteins are in agreement with the SDS-gel mobility of the protein fragments detected in A. The observation that endogenous cTnT and exogenous chicken fast skeletal TnT were modified similarly by μ-calpain cleavage suggests a dependence on myofibril structure rather than the amino acid sequences at the cutting sites.

Similar NH$_2$-terminal truncation of cardiac and fast skeletal muscle TnT by calpain proteolysis. After TRITON® X-100 extraction of transgenic mouse cardiac muscle strips containing both cTnT and chicken fast skeletal muscle TnT (38), Western blot using polyclonal antibody RATnT raised against chicken fast TnT and mAb 2C8 recognizing both cardiac and fast TnTs detected the production of both cardiac and fast skeletal TnT-ND fragments (FIG. 11). Mouse cTnT-ND and chicken fast TnT-ND have different molecular weights due to their amino acid composition in the core structure. While the blot using low cross linker SDS-gel (FIG. 11A) showed only one TnT-ND band, the blot using high cross linker SDS-gel resolved two TnT fragments with distinct immunoreactivities to RATnT and 2C8 antibodies indicating their cTnT and fast TnT origins. Although the amino acid sequences of the NH$_2$-terminal regions of mouse cardiac and chicken fast skeletal muscle TnTs flanking the truncation sites are very different, the similar modification of both endogenous cTnT and exogenous fast TnT upon the TRITON® X-100 extraction-activated µ-calpain cleavage suggests a dependence on myofibril structure rather than the amino acid sequences at the cutting sites. myofibril structure rather than the amino acid sequences at the cutting sites.

EXAMPLE 9

Selective removal of the NH$_2$-terminal variable region of cTnT preserves the binding of cTnT to TnI and tropomyosin with altered affinities. To examine the effect of the NH$_2$-terminal truncation on cTnT interactions within the thin filament regulatory system, the binding of intact and NH$_2$-terminal truncated cTnT to each of TnI and tropomyosin were compared. The results of ELISA solid phase protein binding experiments in FIG. 12A demonstrate that the NH$_2$-terminal truncated cTnT has an increased binding affinity for TnI compared to that of intact cTnT. This is observable in the lower concentration of TnI required to reach 50% of maximum binding (8.73±1.15 nM for cTnT ND versus 15.33±1.36 nM for intact cTnT, P<0.005), reflecting a higher K$_d$ during the initial phase of equilibrium binding. No significant difference in the maximum binding was observed (FIG. 12A insert), indicating no effect on the TnT-TnI coupling strength in the troponin complex. The higher K$_d$ in cTnT-ND-TnI binding may facilitate incorporation of the mutant cTnT into the troponin complex and the thin filament as well as affect the allosteric feature of the Ca$^{2+}$-regulatory system.

The binding of cTnT-ND to tropomyosin also exhibited a higher affinity than that of intact cTnT (FIG. 12B). The concentrations of tropomyosin for 50% maximum binding of cTnT-ND and intact cTnT were 9.73±0.185 nM and 13.50±1.38 nM, respectively (P<0.01). The level of maximum binding was not significantly changed (FIG. 12B insert). With no effect on the anchoring strength of TnT on tropomyosin, the altered binding affinity of NH$_2$-terminal truncated cTnT for tropomyosin may also affect the allosteric feature of the thin filament regulatory system, contributing to myocardial function during ischemia-reperfusion.

Figure 12:
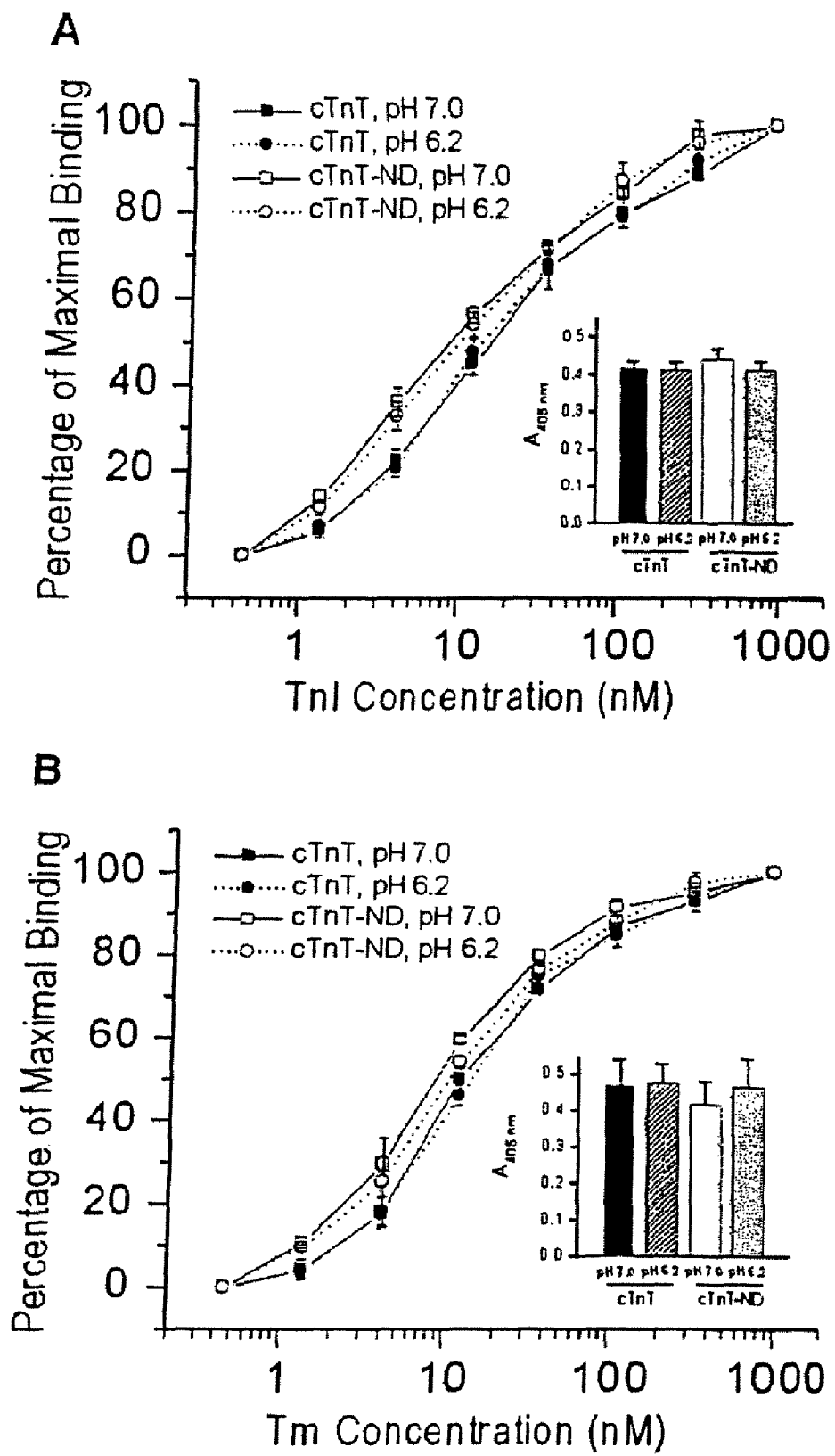
FIG. 12. Removal of the NH$_2$-terminal variable region preserves cTnT's binding to TnI and tropomyosin (Tm) with altered affinities. ELISA protein binding curves demonstrate that the NH$_2$-terminal truncated cTnT has an increased binding affinity for TnI as compared to that of intact cTnT (A). The concentrations of TnI required to reach 50% of maximum binding were 8.73±1.15 nM for cTnT ND and 15.33±1.36 nM for intact cTnT, P<0.005. No significant difference was seen between the maximum bindings of cTnT-ND and intact cTnT to TnI (Panel A insert). The binding of cTnT-ND to tropomyosin also exhibits a higher affinity than that of intact cTnT (B). The concentrations of tropomyosin for 50% maximum binding of cTnT ND and intact cTnT were 9.73±0.185 nM and 13.50±1.38 nM, respectively (P<0.01) The level of maximum binding was not significantly changed (Panel B insert). The decrease of pH from 7.0 to 6.2 did not result in significant change in the binding of both intact and NH$_2$-terminal truncated cTnT to TnI or α-tropomyosin.
Figure 13:
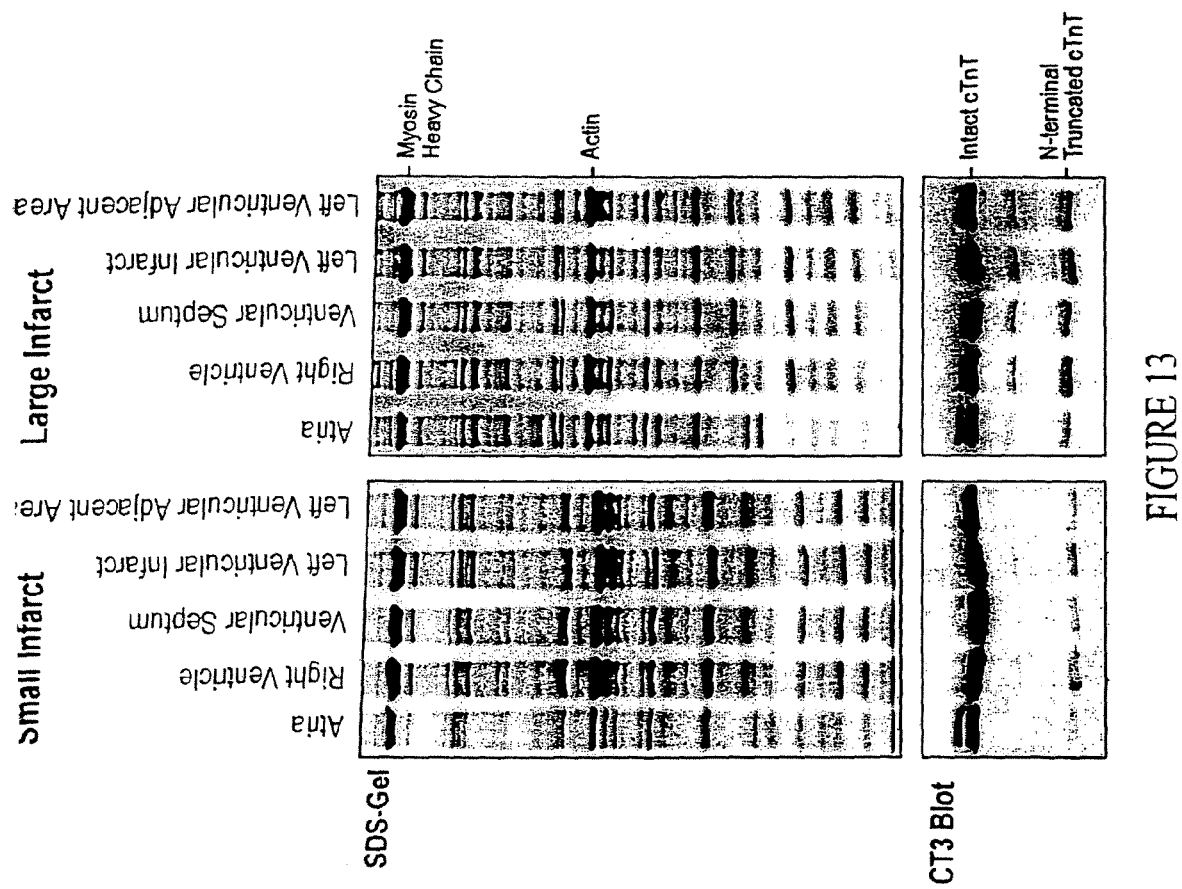
FIG. 13. A comparison of cardiac protein patterns following exposure of ex vivo working mouse hearts to conditions modeling small and large myocardial infarctions. The upper left panel (small infarct) and upper right panel (large infarct) present an unbiased protein expression pattern following SDS-PAGE gel fractionation. The lower left panel (small infarct) and lower right panel (large infarct) present Western blots of gel-fractionated cardiac proteins probed with the mAb CT3, which recognizes the central region of cardiac TnT, as described herein (see, e.g., Example 1). The results shown in the Figure demonstrate that the myocardial infarction models produced significant amounts of the N-terminal truncated cardiac TnT, not only in the infarct but also in the surrounding and remote areas of the ventricles. The response is more prominent in the large infarct model than in the small infarct model. This whole organ response has two-fold significance. First, the release of N-terminal fragment from cardiac TnT is expected to provide a sensitive early diagnostic marker since the production is not restricted to the infarct locus but is apparent in the whole ventricular mass, which would result in a higher serum level. Second, the whole organ responses is expected to have a pathophysiological significance related to the functional adaptation of the ventricles in acute myocardial infarction.
Figure 14:
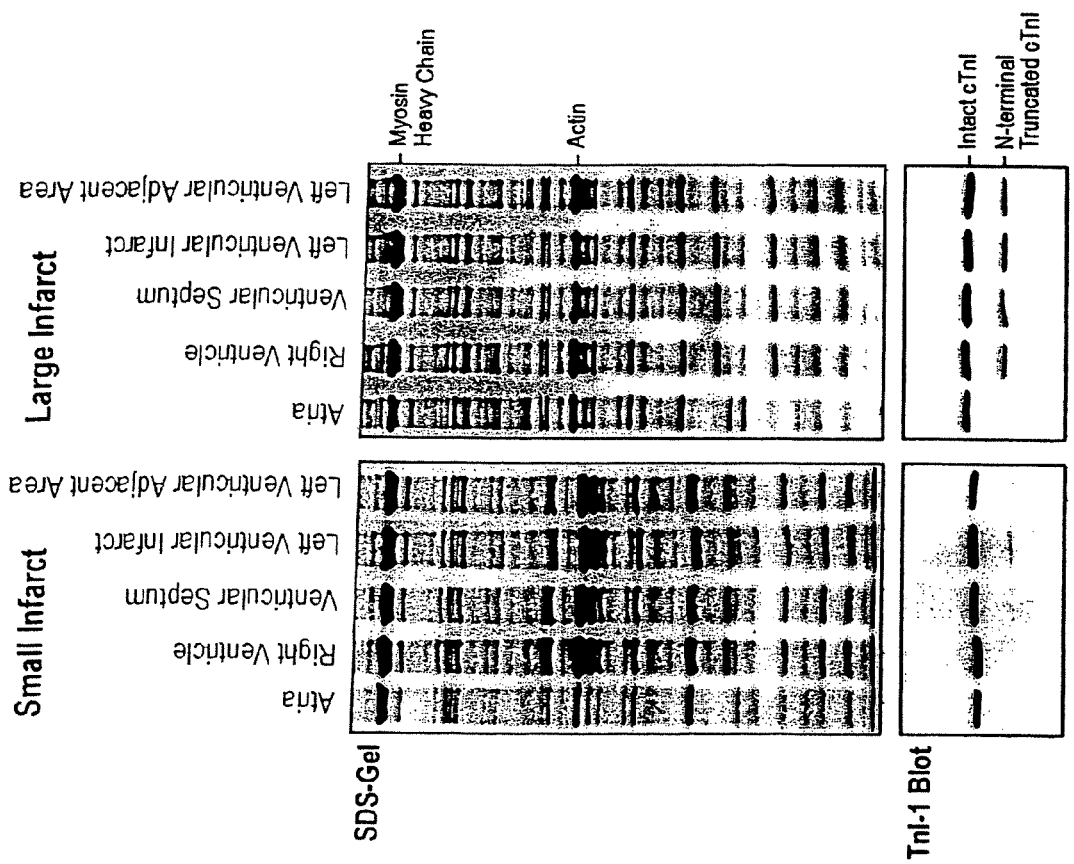
FIG. 14. A comparison of cardiac protein patterns following exposure of ex vivo working mouse hearts to conditions modeling small and large myocardial infarctions. The two upper and two lower panels are as described for FIG. 13, except that the Western blots in the lower panels were probed with TnI-1, which recognizes the C-terminal region of cardiac TnI (as described in reference 46). The results shown in the Figure demonstrate that the myocardial infarction models produced significant amounts of the N-terminal truncated cardiac TnI. Small infarcts produced N-terminal truncated cardiac TnI mainly at the infarct site, but large infarcts produced truncated TnI also in the surrounding and remote areas of the ventricles. The responses are more closely related to the infarct size than that shown by truncation of cardiac TnT (FIG. 13) and may provide a useful marker for the extent or magnitude of myocardial infarction. Similar to that described in FIG. 13, the release of N-terminal fragment of cardiac TnI is expected to provide a sensitive early diagnostic marker in large infarct patients, since the truncated products are not restricted to the infarct locus, appearing throughout the whole ventricular mass, which would result in a higher serum level. The whole-organ response is also expected to have a pathophysiological significance related to the functional adaptation of the ventricles in acute myocardial infarction.
Figure 15:
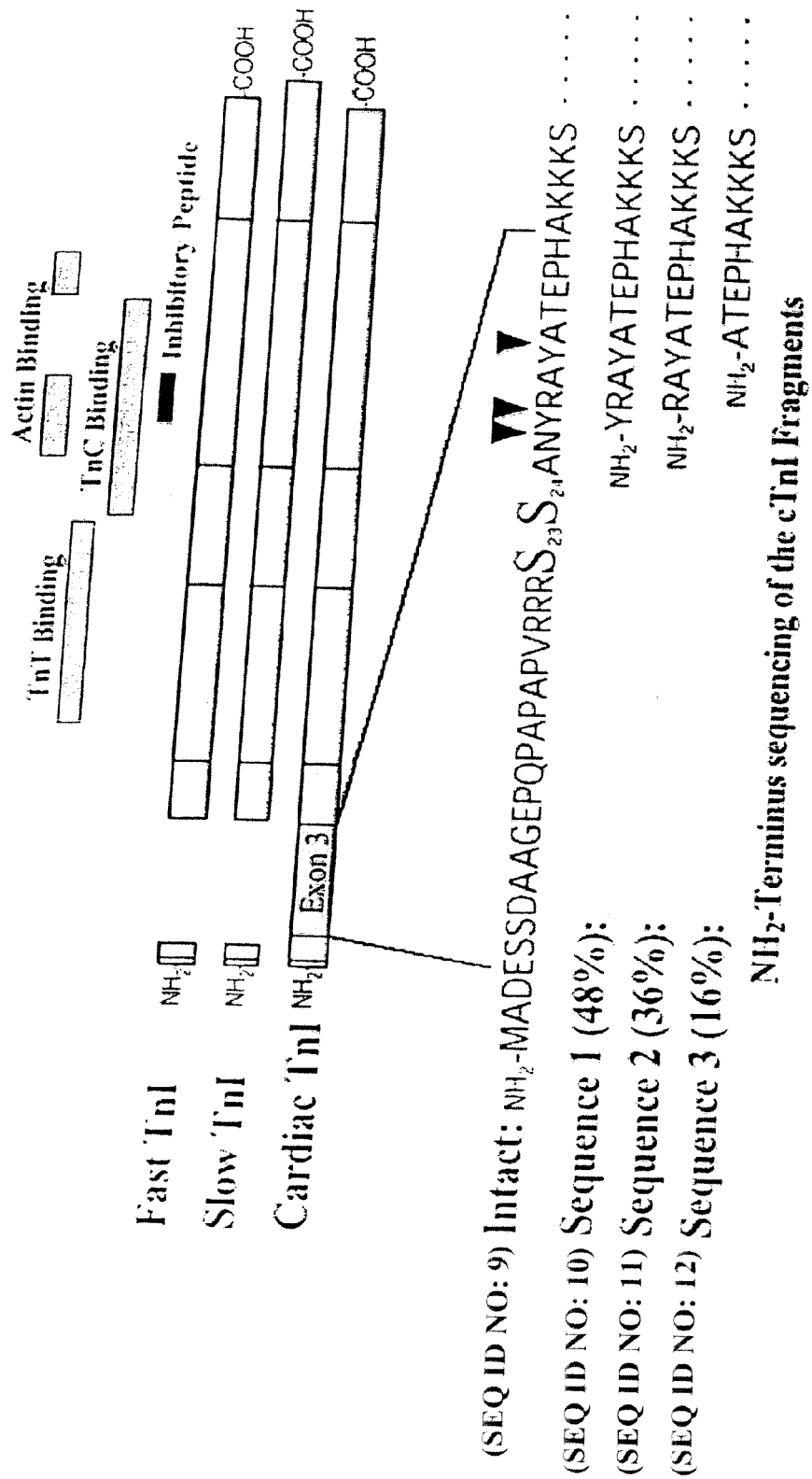
FIG. 15. A schematic map of the coding regions for fast and slow skeletal TnIs as well as for cardiac TnI are presented. Structural maps of rat fast skeletal muscle TnI, slow skeletal muscle TnI, and cTnI are aligned with the regions for the binding of TnC, TnT and actin, as well as the inhibitory peptide indicated. The segments encoded by different exons of the three TnI genes are outlined by the boxes. The cTnI-specific exon 3 is shown by a filled box. N-terminal amino acid sequences of cTnI fragments are presented below the schematic map. The three $NH_2$-terminal sequences determined from the purified rat cTnI fragment are shown and aligned with the sequence encoded by exons 1, 2 and 3 of the rat cTnI gene. The arrowheads indicate the three clustered cleavage sites. The two PKA substrate serine residues (S23 and S24) are highlighted.
Figure 16:
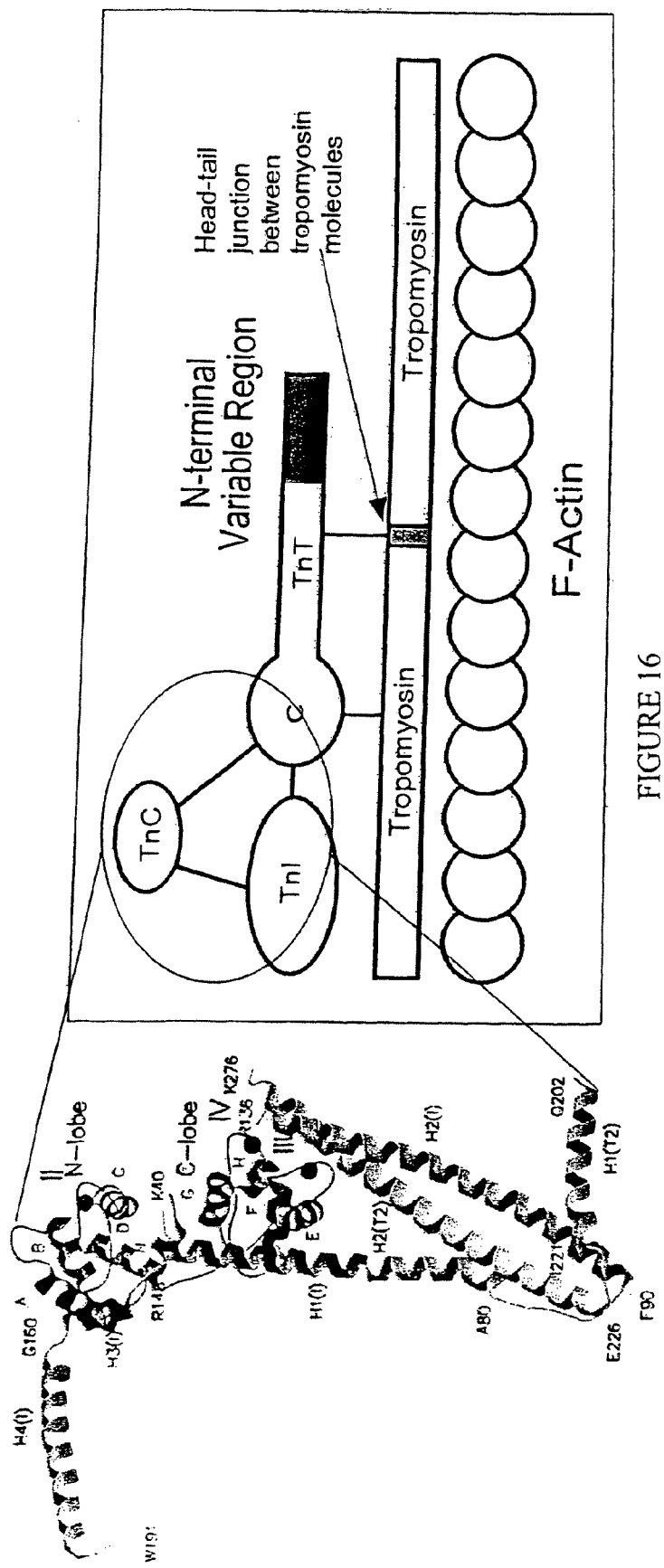
FIG. 16. Schematic structure and function of cardiac troponin T showing selective truncation of cardiac troponin T by μ-Calpain-mediated, myofibril-associated loss of the N-terminus of full-length cTnT in, e.g., ischemia-reperfusion.

Intracellular acidosis occurs in myocardial ischemic injury with a correlation to the function of troponin (49). Therefore, the response of cTnT-ND to lowered pH was compared to the response of intact cTnT. Decrease of pH from 7.0 to 6.2 did not result in significant change in the binary binding affinity of both intact and NH$_2$-terminal truncated cTnT to TnI or tropomyosin (FIG. 12). The results indicate that although environmental pH and the NH$_2$-terminal negative charge of TnT is known to affect the bindings of acidic and basic fast skeletal muscle TnT isoforms to skeletal muscle TnI and tropomyosin (50), the cardiac protein isoforms may have a higher resistance to acidosis. The removal of the entire NH$_2$- terminal variable region corresponding to a large amount of negative charges from cTnT did not convey the effect on the core structure and function seen in the fast TnT isoforms in response to the environmental pH. This observation presents an analogy to a feature of cardiac TnI in which proteolytic removal of the $NH_2$-terminal phosphorylation sites had a functional effect similar to that of protein kinase A phosphorylation (31).

EXAMPLE 10

Screening for modulators of cTnT function. Antigen-antibody interactions, including interactions involving antigenic peptides, are based on conformational fits between the antigenic epitope and the antibody variable region. The binding of a small molecule to a protein can alter the structural conformation of one or more epitopes at or near the binding site, in turn altering the binding affinity of the epitopes to their specific antibodies. Epitope affinity assays can detect such changes in binding affinity, providing a basis for detecting the binding of small molecules to protein structures of interest.

The use of polyclonal versus monoclonal antibodies in ELISA epitope conformational analysis provides some advantages over the homogeneous nature of monoclonal antibodies. A polyclonal antibody is able to detect changes in multiple epitopes on the target structure due to ligand binding. Therefore, a rabbit polyclonal antiserum raised against an N-terminal peptide of human cTnT is used for the initial screening of molecules that bind to the N-terminal region of cTnT. On the other hand, anti-cTnT monoclonal antibodies have been developed against the N-terminal peptide as well as epitopes known to be in regions distant from the N-terminal region. These monoclonal antibodies are used in ELISA epitope analyses to further select the cTnT N-terminal binding molecules for global conformational effects on cTnT structure prior to functional screenings.

To evaluate the capacity of the methods of the invention to detect overall conformational change in cTnT due to modification of the N-terminal structure, ELISA epitope analyses are undertaken using a polyclonal anti-TnT antibody. Mucalpain treatment of cTnT to produce N-terminal truncated cTnT is expected to result in detectable changes in binding affinity in other regions of cTnT. Such results are consistent with N-terminal truncation inducing allosteric change in cTnT, consistent with a role in modulating cardiac muscle contractility.

Any screening technique or method known in the art may be used to identify molecules that bind the N-terminal region of cTnT or cTnI for use in enhancing cardiac muscle relaxation. Preferred methods are the epitope affinity assays noted above. Proteolytic removal of the N-terminal 30 amino acids of cTnI enhances cardiac diastolic function. This effect is similar to the physiological effect resulting from cTnI phosphorylation at Ser23/Ser24 (in the N-terminal region of cTnI) induced by β-adrenergic stimulation. In contrast to the broad effects of β-adrenergic agonists, selective modification of the N-terminal structure of cTnI avoids many unwanted side effects. In like manner, N-terminal truncation of cTnT results in improved cardiac performance while avoiding undesired side effects. The enhancement of myocardial relaxation produces a higher cardiac output without a proportional increase in energy expenditure. Therefore, the N-terminal domain of cTnT and/or cTnI is a suitable target for developing a new generation of drugs for the treatment of heart failure. The screens for cTnT and/or cTnI modulators are expected to identify molecules that bind the N-terminal region of cTnT and/or cTnI, or that and enhance cardiac muscle relaxation.

High-throughput embodiment. In some embodiments, the ELISA epitope conformational analysis is implemented in a high throughput screening format to identify protein-binding molecules. Microtiter plate-based ELISA methodology is one of the most widely used enzyme immunoassays. Its high sensitivity, ability to simultaneously process large numbers of samples, amenability to automation, and use of non-radioactive reagents has led to its successful application in a variety of contexts. Accordingly, this aspect of the invention is not limited to assays for binding agents, e.g., modulators, of the N-terminal domain of cTnT and/or cTnI, but rather finds application to peptide or protein antigens in general.

ELISA methods can be classified as direct, indirect or sandwich assays. Various amplification systems may be added to the basic methods to enhance sensitivity. Generally, indirect ELISA with an antigen immobilized on, or coated on, the microtiter plate for interaction with a primary antibody and detection via an enzyme-labeled second antibody is the most commonly used method for measuring the reaction of specific antibodies to their antigens.

The antibody-antigen binding affinity is based on conformational fits between the antigenic epitope and the antibody variable region. Changes in the conformation of an antigenic epitope can alter its binding affinity for corresponding antibodies. When a protein or peptide binds to a ligand molecule, the structural conformation of the binding site and, often, nearby regions, changes, producing conformational changes in related epitope structures. Based on this mechanism, epitope affinity assays detect the binding of small molecules to a protein structure of interest.

ELISA-based methods have been developed that detect the binding of Zn(II) ions to the N-terminal region of avian breast muscle troponin T (Wang et al., 1998, Biochemistry 37:14519-14528, incorporated herein by reference). Direct conformational changes in the Zn(II) binding sites, and secondary conformational changes in remote regions, were sensitively detected as affinity changes of specific antibodies. This methodology also detects long-range conformational changes induced by the binding of a monoclonal antibody to the N-terminal region of a recombinant troponin T protein (Jin et al., 2000, Am. J. Physiol.: Cell Physiol. 279:C1067-1077) and epitopic conformational changes in the C-terminal domain of TnT induced by $Ca^{2+}$ binding to the troponin complex (Jin et al., 2001, Biochemistry 40, 2623-2631). Similarly, this methodology detects conformational changes in multiple epitopes on calponin (a smooth muscle and non-muscle cytoskeleton regulatory protein) resulting from phosphorylation at Ser175.

Initial high-throughput screens for modulators of the function of the N-terminal domain of cTnT or cTnI are expected to assess water-soluble molecules that are amenable to aqueous ELISA assays and that are amenable to aqueous-based therapeutic or pharmaceutical compositions. In one embodiment, the basic indirect ELISA method involves an initial coating of microtiter plate wells with a synthetic N-terminal peptide of human cTnT or cTnI. The synthetic peptide is coated onto 96-well microtiter plates at 100 μL per well in 50 mM sodium carbonate buffer, pH 9.6, by incubation at 4° C. overnight. Although the coating of peptides on microtiter plates is not as effective as coating with intact proteins, there is sufficient coating of various peptides to make use of the method. After washing and blocking the remaining plastic surfaces with 1% BSA and 0.05% TWEEN®20 in phosphate buffered saline, pH 7.4, (PBS), the immobilized N-terminal peptide is incubated at 37° C. for 1 hour with a candidate modulator dissolved in PBS at 10 μM. After washing away the unbound molecules, a predetermined dilution of an antibody specific to the N-terminal peptide, e.g., the rabbit anti-cTnI N-terminal peptide antiserum, is prepared in PBS containing 0.1% BSA. The diluted antibody is added to the plates at 100 μL per well and incubated at 37° C. for 1 hour. Following washes with PBS plus 0.05% TWEEN®20 (PBS-T) to remove unbound antibody, the plates are further incubated with horseradish peroxidase (HRP)-conjugated anti-rabbit IgG second antibody, followed by PBS-T washes and $H_2O_2$-2,2'-azinobis-(3-ethylbenzthiazolinesulfonic acid) (ABTS) substrate and the reaction is allowed to proceed in accordance with a standard protocol for this colorimetric assay that is known in the art. An $A_{405\ nm}$ curve for each assay well is recorded by an automated microplate reader (BioRad Benchmark). For molecules that precipitate in PBS or that are expected to react with a component of PBS, alternative buffer systems, such as Tris-HCl or imidazole-HCl, are available and suitable.

Pre-titration of the N-terminal peptide specific antibody is used to determine a dilution for each antibody to produce an $A_{405\ nm}$ of 0.5-0.7 under the experimental conditions in the absence of a candidate modulator. The binding of a molecule to the N-terminal peptide is expected to alter (most likely reduce) the binding affinity of the peptide for the polyclonal antibody and will typically result in a lower $A_{405\ nm}$ reading. The values in the linear range of enzymatic color development are used to evaluate whether the treatment of the cTnI-N-terminal peptide with a candidate modulator resulted in a change in the affinity to the anti-peptide antibody. A positive result is consistent with binding between the molecule and the N-terminal region.

The most time-consuming step in the ELISA screening procedure is the dilution and addition of individual molecules into the assay wells. All other steps can be performed with multiple channel pipetting or other equipment allowing multiple, simultaneous processing steps to be performed in parallel.

It is expected that the positive molecules will constitute a small portion of the molecular libraries being screened. Therefore, one approach to significantly increase the scale of the screening is to group the molecules into 10×10 arrays. Each of the 100 molecules is screened as 20 sets of mixtures containing 10 molecules each (with none of the 20 sets containing the same 10 molecules). From the results of the 20 sets, one can identify which, if any, of the 100 molecules is positive. This design is expected to increase screening efficiency 5-fold, with a concomitant increase in confirmatory power (each molecule is tested twice). A precaution in applying this approach is to make sure that the mixes of molecules will not result in chemical changes (e.g., reactions between mixed candidate modulators). It may also be necessary to adjust the total concentration of molecules in one sample to minimize nonspecific effects. One of skill in the art will recognize that the grouping of testing molecules or candidates can be based on a factor other than 10, and all such groupings are contemplated by the invention. Moreover, one of skill will recognize the general applicability of grouping candidate molecules in screens of a wide variety of types designed to reveal interactions between candidates and a wide variety of antigenic peptides or proteins of interest. The high-throughput screening method with the grouping of candidate molecules has been exemplified herein in the context of ELISA screens for modulators of the N-terminal domain of cTnT or cTnI.

In some assays, a candidate modulator may non-specifically bind immunoglobulin, resulting in altered affinity of the antibody and/or the HRP-labeled second antibody due to a false positive. To avoid, or minimize, false positives, positive molecules are examined in control ELISA assays using an unrelated antigen-antibody pair. If the control ELISA also shows that the testing molecule results in an altered, e.g. a decreased, $A_{405\ nm}$, the molecule can be avoided as a compound producing artefactual results.

Identification of candidates as modulators on the basis of binding the N-terminal region of cTnT or cTnI, as detected in the ELISA with a single antibody dilution, are preferably confirmed by comparing antibody affinity titration curves in the presence versus absence of the candidate modulator. The ELISA is carried out as above with, e.g., five serial dilutions of the anti-N-terminal peptide antibody (e.g., dilutions of $10^2$, $10^3$, $10^4$, $10^5$, and $10^6$). This series of dilutions has been found to be highly reliable in detecting changes in antibody affinity resulting from small molecule binding to the antigen.

The N-terminal peptide binding molecules, preferably confirmed as described above, are amenable to further evaluation of binding affinity. For example, indirect ELISA as described above is performed with serial dilutions of the binding molecule (Jin et al., 2000, Biochemistry 39:11702-11713). The initial testing concentrations are, e.g., 100 μM, 10 μM, 1 μM, 0.1 μM, and 10 nM. After identifying the affinity range, a finer gradient is optionally examined to construct the affinity titration curve and estimate the concentration required for reaching 50% maximum binding. This information reflects the potency of the molecule in physiological and pharmacological applications.

The screening of N-terminal peptide binding molecules will identify candidates that can induce functional changes in cTnT or cTnI to mimic the effect of N-terminal truncation or phosphorylation (in the case of cTnI) on cardiac muscle relaxation. Since the effect of N-terminal structure modification is conferred through allosteric effects on other regions of cTnT or cTnI, molecules binding to the N-terminal region may be further evaluated by ELISA conformational analyses using an antibody or antibodies against at least one non-N-terminal region epitope. The ELISA is carried out as described above using, in one embodiment, full-length or intact cTnT or cTnI protein coated onto the plates. See generally, Wang et al., 1998, Biochemistry 37:14519-14528; Jin et al., 2000, Biochem. J. 350:579-588; Jin et al., 2000, Biochemistry 39:11702-11713. Detection of long-range, global conformational changes upon binding of a candidate molecule to the N-terminal region is consistent with that molecule inducing functional changes in cTnT or cTnI.

To maximize throughput, the ELISA assay has been described in terms of initially testing a single concentration of the candidate modulators. This concentration (10 μM) will identify high affinity binding ligands for future use as pharmacological reagents. One of skill in the art will recognize that this concentration of candidates can be adjusted, for example by increasing the concentration to 50-100 μM if multiple screens fail to yield a positive result. Of course, post-screen modifications of the structure of any identified modulators can be used to prepare a derivative in which the binding affinity has been altered relative to the originally identified molecule. The conformational changes detected by ELISA epitope affinity analyses are amenable to confirmation by spectrometric measurements.

Beyond screens designed to identify modulators of cTnT or cTnI activity, the invention comprehends assays for other physiological effects that mimic the N-terminally truncated or phosphorylated forms of cTnI. For example, actomyosin MgATPase assays are performed to titrate the $Ca^{2+}$ sensitivity of mouse cardiac myofibrils in the presence versus absence of the candidate molecules. The assays are known in the art and are carried out using conventional protocols. For example, a microtiter plate-based method may be used (Barbato et al., 2005, J. Biol. Chem. 280:6602-6609). The assays reveal the effects of the candidate molecules on the $Ca^{2+}$ sensitivity of cardiac myofibrils. Molecules that decrease the $Ca^{2+}$ sensitivity of cTnI are identified as potential candidates that mimic the effect of physiological modifications of the cTnI N-terminal region.

The invention also contemplates modifications of modulators identified in the above-described screens. For hydrophilic compounds, e.g., modifications known in the art will be undertaken to facilitate effective penetration of the modulator into cardiac muscle cells. As an alternative, the modulators are delivered in a vehicle that promotes effective entry into the targeted cardiac muscle cells using techniques known in the art (e.g., targeted liposomes, benign viruses modified by linkage to the modulator, and the like).

Once the modulator has been engineered, if necessary, to ensure passage into the cardiac muscle cell or cardiomyocyte, the effects of the modulator on cardiac function is tested in isolated working mouse hearts. The measurements may suitably be done in 5-6-month-old mice using the Langendorff-Neely isolated working heart preparation, as known in the art (see Barbato et al., J. Biol. Chem., 2005, 280:6602-6609). The molecules are delivered to the working heart preparations through coronary perfusions and both cardiac muscle contractility and cardiac function are recorded to evaluate the pharmacological effects of the modulator on the velocity of myocardial relaxation, cardiac output versus energy expenditure, and tolerance to decreases in pre-load, providing information useful in administering the modulator as a therapeutic to humans and/or other animals.

Any subsequent chemical modification of a modulator, for example to lower or eliminate toxicity or other side effects, are accomplished using techniques well known in the medicinal chemistry field. The effect of such modifications are readily determined using the assays disclosed herein.

EXAMPLE 11

Diagnostic applications using a binding partner specific for the N-terminal domain of cTnT. Using the methods described herein, an antibody is generated that specifically recognized the N-terminal domain of cardiac TnT. Through routine antibody generation techniques and screening against full-length and N-terminally truncated forms of cTnT, as well as the N-terminal peptide of cTnT, one of skill would be able to identify an antibody that exhibited such selective binding characteristics. More generally, one of skill would be able to identify any specific binding partner demonstrating a detectable difference in affinity for binding the full-length and N-terminally truncated forms of cTnT. These selective binding molecules are useful in screening for the relative presence of full-length cTnT, N-terminally truncated cTnT, and/or an N-terminal fragment of cTnT. As a control, a binding partner specific for cTnT, regardless of whether its N-terminus is truncated or not, is used in some embodiments, to provide a measure of total cTnT. For example, an antibody recognizing a cTnT epitope that is not N-terminally disposed, or the natural binding partners of TnT (e.g., tropomyosin), would be suitable.

These screening methods provide the basis for diagnostic methods designed to reveal the relative proportion of cTnT that is truncated (or, conversely, full length), providing the basis for diagnosing a cardiac condition that involves post-translational adaptation in order to compensate for the reduced function. Thus, it is within the skill in the art to develop, e.g., an ELISA-based method using this strategy to detect structural modification in the N-terminal region of cardiac TnT. By measuring the relative amounts of the various cTnT forms (N-terminal fragment, N-terminally truncated fragment and full-length cTnT) produced in the presence versus the absence of a candidate modulator of posttranslational processing of cTnT, these methods and other methods known in the art can be used to screen for prophylactics and therapeutics useful in preventing, treating or ameliorating cardiovascular disease. Analogous methods, e.g., immunoassay methods, provide the basis of embodiments of the diagnostic methods according to the invention, providing an early, specific measure of cardiovascular distress characteristic of a variety of cardiovascular diseases and conditions such as myocardial infarction. The invention further comprehends diagnostic methods in which the relative amounts of the various cTnT forms are determined or measured in combination with determinations of the relative amounts of the various forms (e.g., full-length, N-terminally truncated, $Ser_{23}$-phosphorylated, $Ser_{24}$-phosphorylated) of cTnI, as disclosed in U.S. Ser. No. 11/311,472, incorporated herein by reference. These latter diagnostic methods are expected to provide an additional measure of protection in ensuring that the methods provide accurate and reliable indications of cardiovascular health.

The N-terminally truncated forms of cTnI used in combination therapies as disclosed herein, as well as various methodologies and other pertinent disclosures, are provided in U.S. patent application Ser. No. 11/311,472, incorporated herein by reference.

The following references have been cited throughout this document and each reference is incorporated herein by reference in its entirety.

REFERENCES

1. Leavis, P. C., and Gergly, J. (1984) Thin filament proteins and thin filament-linked regulation of vertebrate muscle contraction. *CRC Crit. Rev. Biochem.* 16, 235-305.
2. Zot, A. S., and Potter, J. D. (1987) Structural aspects of troponin-tropomyosin regulation of skeletal muscle contraction. *Annu. Rev. Biophys. Biophys. Chem.* 16, 535-559.
3. Tobacman, L. S. (1996) Thin filament-mediated regulation of cardiac contraction. *Annu. Rev. Physiol.* 58,447-481.
4. Perry, S. V. (1998) Troponin T: genetics, properties and function. *J. Muscle Res. Cell Motil.* 19, 575-602.
5. Breitbart, R. E, and Nadal-Ginard, B. (1986) Complete nucleotide sequence of the fast skeletal troponin T gene. Alternatively spliced exons exhibit unusual interspecies divergence. *J. Mol. Biol.* 188, 313-324.
6. Jin, J.-P., Huang, Q.-Q., Yeh, H.-I, and Lin, J. J.-C. (1992) Complete nucleotide sequence and structural organization of rat cardiac troponin T gene. A single gene generates embryonic and adult isoforms via developmentally regulated alternative splicing. *J. Mol. Biol.* 227, 1269-1276.
7. Huang, Q. Q., Chen, A., and Jin, J.-P. (1999) Genomic sequence and structural organization of mouse slow skeletal muscle troponin T gene. *Gene* 229, 1-10.
8. Jin J.-P., and Lin, J. J.-C. (1988) Rapid purification of mammalian cardiac troponin T and its isoform switching in rat hearts during development. *J. Biol. Chem.* 263, 7309-7315.
9. Wang, J., and Jin, J.-P. (1997) Primary structure and developmental acidic to basic transition of 13 alternatively spliced mouse fast skeletal muscle troponin T isoforms. *Gene* 193, 105-114.
10. Jin, J.-P., Chen, A., and Huang, Q. Q. (1998) Three alternatively spliced mouse slow skeletal muscle troponin T isoforms: conserved primary structure and regulated expression during postnatal development. *Gene* 214, 121-129.
11. Pearlstone, J. R., and Smillie, L. B. (1982) Binding of troponin-T fragments to several types of tropomyosin. Sensitivity to Ca2+ in the presence of troponin-C. *J. Biol. Chem.* 257, 10587-10592.
12. Pearlstone, J. R., and Smillie, L. B. (1985) The interaction of rabbit skeletal muscle troponin-T fragments with troponin-I. *Can. J. Biochem.* 63, 212-218.
13. Hinkle A., Goranson, A., Butters, C. A., Tobacman, L. S. (1999) Roles for the troponin tail domain in thin filament assembly and regulation. A deletional study of cardiac troponin T. *J. Biol. Chem.* 274, 7157-7164.
14. Pan, B.-S., Gordon, A. M., and Potter, J. D. (1991) Deletion of the first 45 NH2-terminal residues of rabbit skeletal troponin T strengthens binding of troponin to immobilized tropomyosin. *J. Biol. Chem.* 266, 12432-12438.
15. Fujita, S., Maéda, K., and Maéda, Y. (1992) Expression in *Escherichia coli* and a functional study of a beta-troponin T 25 kDa fragment of rabbit skeletal muscle. *J. Biochem.* 112, 306-308.
16. Chandra, M., Montgomery, D. E., Kim, J. J., and Solaro, R. J. (1999) The N-terminal region of troponin T is essential for the maximal activation of rat cardiac myofilaments. *J. Mol. Cell Cardiol.* 31, 867-880.
17. Gomes, A. V., Guzman, G., Zhao, J., and Potter, J. D. (2002) Cardiac troponin T isoforms affect the $Ca^{2+}$ sensitivity and inhibition of force development. Insights into the role of troponin T isoforms in the heart. *J. Biol. Chem.* 277, 35341-35349.
18. Anderson, P. A., Greig, A., Mark, T. A., Malouf, N. N., Oakeley, A. E., Ungerleider, R. M., Allen, P. D., and Kay, B. K. (1995) Molecular basis of human cardiac troponin T isoforms expressed in the developing, adult, and failing heart. *Circ. Res.* 76, 681-686.
19. Biesiadecki, B. J. and J.-P. Jin. (2002) Exon skipping in cardiac troponin T of turkeys with inherited dilated cardiomyopathy. *J. Biol. Chem.* 277, 18459-18468.
20. Biesiadecki, B. J., Elder, B. D., Yu, Z. B., and Jin, J. P. (2002) Cardiac troponin T variants produced by aberrant splicing of multiple exons in animals with high instances of dilated cardiomyopathy. *J. Biol. Chem.* 277, 50275-50285.
21. Wang, J., and Jin, J.-P. (1998) Conformational modulation of troponin T by configuration of the $NH_2$-terminal variable region and functional effects. *Biochemistry* 37, 14519-14528.
22. Jin, J.-P., and Root, D. D. (2000) Modulation of troponin T molecular conformation and flexibility by metal ion binding to the $NH_2$-terminal variable region. *Biochemistry* 39, 11702-11713.
23. Jin, J.-P., Chen, A., Ogut, O., and Huang, Q.-Q. (2000) Conformational modulation of slow skeletal muscle troponin T by an NH(2)-terminal metal-binding extension. *Am. J. Physiol. Cell Physiol.* 279, C1067-1077.
24. Yu, Z. B., Gao, F., Feng, H., and Jin. J.-P. (2002) Role of myofilament protein isoform regulation in the decreases in contractile force and tolerance to fatigue of slow skeletal muscles after unloading. *Biophys. J.* 82, 394a.
25. Sumandea, M. P., Burkart, E. M., Kobayashi, T., De Tombe, P. P., and Solaro, R. J. (2004) Molecular and integrated biology of thin filament protein phosphorylation in heart muscle. *Ann. NY Acad. Sci.* 1015,39-52.
26. Hirano, K., Hirano, M., and Kanaide, H. (2004) Regulation of myosin phosphorylation and myofilament $Ca^{2+}$ sensitivity in vascular smooth muscle. *J. Smooth Muscle Res.* 40, 219-236.
27. Layland J., Solaro, R. J., and Shah, A. M. (2005) Regulation of cardiac contractile function by troponin I phosphorylation. *Cardiovasc. Res.* 66, 12-21.
28. Murphy, A. M., Kogler, H., Georgakopoulos, D., McDonough, J. L., Kass, D. A., Van Eyk, J. E., Marban, E. (2000) Transgenic mouse model of stunned myocardium. *Science* 287, 488-491.
29. Communal, C., Sumandea, M., de Tombe, P., Narula, J., Solaro, R. J., Hajjar, R. J. (2002) Functional consequences of caspase activation in cardiac myocytes. *Proc. Natl. Acad. Sci. U.S.A.* 99, 6252-6256.
30. Yu, Z. B., Zhang, L. F., and Jin, J.-P. (2001) A proteolytic $NH_2$-terminal truncation of cardiac troponin I that is up-regulated in simulated microgravity. *J. Biol. Chem.* 276, 15753-15760.
31. Barbato, J. C., Huang, Q. Q., Hossain, M. M., Bond, M., Jin, J.-P. (2005) Proteolytic N-terminal truncation of cardiac troponin I enhances ventricular diastolic function. *J. Biol. Chem.* 280, 6602-6609.
32. Ohtsuki, I., Shiraishi, F., Suenaga, N., Miyata, T., Tanokura, M. (1984) A 26K fragment of troponin T from rabbit skeletal muscle. *J. Biochem.* 95, 1337-1342.
33. Kitamura, S., Muroya, S., Tanabe, S., Okumura, T., Chikuni, K., and Nishimura, T. (2005) Mechanism of production of troponin T fragments during postmortem aging of porcine muscle. *J. Agric. Food Chem.* 53, 4178-4181.
34. Goll, D. E., Thompson, V. F., Li, H., Wei, W., and Cong, J. (2003) The calpain system. *Physiol. Rev.* 83, 731-801.
35. Cong, J. Y., Goll, D. E., Peterson, A. M., and Kapprell, H. P. (1989) The role of autolysis in activity of the Ca2+-dependent proteinases (mu-calpain and m-calpain). *J. Biol. Chem.* 264, 10096-10103.
36. Di Lisa, F., De Tullio, R., Salamino, F., Barbato, R., Melloni, E., Siliprandi, N., Schiaffino, S., and Pontremoli, S. (1995) Specific degradation of troponin T and I by mu-calpain and its modulation by substrate phosphorylation. *Biochem. J.* 308, 57-61.
37. Biesiadecki, B. J. and Jin, J.-P. (2005) N-terminal truncation of cardiac troponin T by restricted proteolysis in myocardial ischemia-reperfusion. *Biophys. J.* 88, 360a.
38. Huang, Q.-Q., Brozovich, F. V., and Jin, J.-P. (1999) Fast skeletal muscle troponin T increases the cooperativity of transgenic mouse cardiac muscle contraction. *J. Physiol.* (*London*) 520, 231-242.
39. Jin, J.-P., Brotto, M. A., Hossain, M. M., Huang, Q. Q., Brotto, L. S., Nosek, T. M., Morton, D. H., Crawford, T. O. (2003) Truncation by Glu180 nonsense mutation results in complete loss of slow skeletal muscle troponin T in a lethal nemaline myopathy. *J. Biol. Chem.* 278, 26159-26165.
40. Jin, J.-P., Wang, J., and Zhang, J. (1996) Expression of cDNAs encoding mouse cardiac troponin T isoforms: characterization of a large sample of independent clones. *Gene* 168, 217-221.
41. Jin, J.-P. (1995) Cloned rat cardiac titin class I and class II motifs. Expression, purification, characterization, and interaction with F-actin. *J. Biol. Chem.* 270, 6908-6916.
42. Guttmann, R. P., Elce, J. S., Bell, P. D., Isbell, J. C., and Johnson, G. V. W. (1997) Oxidation inhibits substrate proteolysis by calpain I but not autolysis. *J. Biol. Chem.* 272, 2005-2012.
43. Wang, K. K., Nath, R., Posner, A., Raser, K. J., Buroker-Kilgore, M., Hajimohammadreza, I., Probert, A. W., Jr., Marcoux, F. W., Ye, Q., Takano, E., Hatanaka, M., Maki, M., Caner, H., Collins, J. L., Fergus, A., Lee, K. S., Lunney, E. A., Hays, S. J., and Yuen, P. (1996) An alpha-mercaptoacrylic acid derivative is a selective nonpeptide cell- 44. Smillie, L. B. (1982) Preparation and identification of alpha- and beta-tropomyosins. *Methods Enzymol.* 85, 234-241.
45. Solaro, R. J., Pang, D. C., and Briggs, F. N. (1971) The purification of cardiac myofibrils with Triton X-100. *Biochim. Biophys. Acta.* 245, 259-262.
46. Jin, J.-P., Yang, F. W., Yu, Z. B., Ruse, C., Bond, M., and Chen, A. (2001) The highly conserved COOH-terminus of troponin I forms a $Ca^{2+}$-modulated allosteric domain in the troponin complex. *Biochemistry* 40, 2623-2631.
47. Lin, J. J.-C., Chou, C.-S., and Lin, J. L.-C. (1985) Monoclonal antibodies against chicken tropomyosin isoforms: production, characterization, and application. *Hybridoma* 4, 223-242.
48. Wang, Q., Reiter, R. S., Huang, Q. Q., Jin, J.-P., and Lin, J. J. (2001) Comparative studies on the expression patterns of three troponin T genes during mouse development. *Anat. Rec.* 263, 72-84.
49. Murphy, A. M. (2006) Heart failure, myocardial stunning, and troponin: a key regulator of the cardiac myofilament. *Congest Heart Fail.* 12, 32-38; quiz 39-40.
50. Ogut, O., and Jin, J.-P. (1998) Developmentally regulated, alternative RNA splicing-generated pectoral muscle-specific troponin T isoforms and role of the $NH_2$-terminal hypervariable region in the tolerance to acidosis. *J. Biol. Chem.* 273, 27858-27866.
51. Takeda, S., Yamashita, A., Maeda, K., and Maeda, Y. (2003) Structure of the core domain of human cardiac troponin in the Ca(2+)-saturated form. *Nature* 424, 35-41.
52. Vinogradova, M. V., Stone, D. B., Malanina, G. G., Karatzaferi, C., Cooke, R., Mendelson, R. A., Fletterick, R. J. (2005) Ca(2+)-regulated structural changes in troponin. *Proc. Natl. Acad. Sci. U.S.A.* 102, 5038-5043.
53. Jin, J.-P., and Samanez, R. A. (2001) Evolution of a metal-binding cluster in the NH(2)-terminal variable region of avian fast skeletal muscle troponin T: functional divergence on the basis of tolerance to structural drifting. *J. Mol. Evol.* 52, 103-116.
54. Piper, H. M., Meuter, K., Schafer, C. (2003) Cellular mechanisms of ischemia-reperfusion injury. *Ann. Thorac. Surg.* 75, S644-S648.
55. Martin, A. F. (1981) Turnover of cardiac troponin subunits. Kinetic evidence for a precursor pool of troponin-I. *J. Biol. Chem.* 256, 964-968.
56. Colantonio, D. A., Van Eyk, J. E., and Przyklenk, K. (2004) Stunned peri-infarct canine myocardium is characterized by degradation of troponin T, not troponin I. *Cardiovasc. Res.* 63, 217-225.
57. Foster, D. B., Noguchi, T., VanBuren, P., Murphy, A. M., and Van Eyk, J. E. (2003) C-terminal truncation of cardiac troponin I causes divergent effects on ATPase and force: implications for the pathophysiology of myocardial stunning. *Circ. Res.* 93, 917-924.

Having thus described at least one embodiment of each of several aspects of the invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of determining the likelihood of developing or diagnosing a cardiac disease comprising
   (a) obtaining a biological sample of a body fluid from a mammalian subject;
   (b) measuring the level of at least one truncated form of cardiac troponin T in said sample; and
   (c) determining the likelihood of developing or diagnosing a cardiac disease based on the measured level of at least one truncated form of cardiac troponin T in said sample.

2. A method of determining the likelihood of developing or diagnosing a cardiac disease comprising
   (a) obtaining a biological sample of a body fluid from a subject;
   (b) measuring the level of at least one truncated form of cardiac troponin T in the sample resulting from a post-translational truncation of cardiac troponin T; and
   (c) determining the likelihood of developing or diagnosing a cardiac disease based on the measured level of at least one truncated form of cardiac troponin T in the sample.

3. A method of determining the likelihood of developing or diagnosing a cardiac disease comprising
   (a) obtaining a biological sample of a body fluid from a subject;
   (b) measuring the level of at least one truncated form of cardiac troponin T in the sample resulting from a proteolytic truncation of cardiac troponin T; and
   (c) determining the likelihood of developing or diagnosing a cardiac disease based on the measured level of at least one truncated form of cardiac troponin T in the sample.

4. A method of determining the likelihood of developing or diagnosing a cardiac disease comprising
   (a) obtaining a biological sample of a body fluid from a subject;
   (b) measuring the level of at least one truncated form of cardiac troponin T in the sample resulting from $NH_2$-terminal truncation of cardiac troponin T; and
   (c) determining the likelihood of developing or diagnosing a cardiac disease based on the measured level of at least one truncated form of cardiac troponin T in the sample.

5. The method according to claim 1, 2, 3 or 4 wherein the subject is a human patient.

6. The method according to claim 1, 2, 3 or 4 wherein the truncated form of cardiac troponin T is $cTnT_{72\text{-}291}$.

7. The method according to claim 1, 2, 3 or 4 wherein said measuring comprises an immunoassay.

8. The method according to claim 7 wherein said immunoassay comprises an antibody selectively binding to said truncated form of cardiac troponin T.

9. The method according to claim 8 wherein said truncated form of cardiac troponin T is $cTnT_{72\text{-}291}$.

10. The method according to claim 7 wherein said immunoassay comprises a differential measurement of a truncated cTnT based on measures of the levels of at least two forms of cTnT in said sample.

11. The method according to claim 10 wherein the differential measurement comprises detecting antibody binding and assessing cTnT size.

12. The method according to claim 11 wherein said differential measurement comprises a comparison of the measured quantities of a truncated cTnT and a full-length cTnT.

13. The method according to claim 1, 2, 3, or 4 wherein the truncated form of cardiac troponin T consists of an $NH_2$-terminal peptide of cTnT.

14. The method according to claim 1, 2, 3 or 4 wherein the truncated form of cardiac troponin T is $cTnT_{1\text{-}71}$.

15. The method according to claim 1, 2, 3, or 4 wherein the truncated form of cardiac troponin T consists of $NH_2$-terminal truncated cTnT.

* * * * *

SEQUENCE LISTING

```
<160> NUMBER OF SEQ ID NOS: 29

<210> SEQ ID NO 1
<211> LENGTH: 28
<212> TYPE: DNA
<213> ORGANISM: Artificial sequence
<220> FEATURE:
<223> OTHER INFORMATION: Synthetic primer

<400> SEQUENCE: 1
agccccatat gctcttcatg cccaactt                                          28

<210> SEQ ID NO 2
<211> LENGTH: 38
<212> TYPE: PRT
<213> ORGANISM: Mus musculus
<220> FEATURE:
<223> OTHER INFORMATION: N-Terminal amino acid sequence

<400> SEQUENCE: 2

Glu Gly Pro Val Glu Asp Thr Lys Pro Lys Pro Ser Arg Leu Phe Met
1               5                   10                  15

Pro Asn Leu Val Pro Pro Lys Ile Pro Asp Gly Glu Arg Val Asp Phe
            20                  25                  30

Asp Asp Ile His Arg Lys
        35

<210> SEQ ID NO 3
<211> LENGTH: 26
<212> TYPE: PRT
<213> ORGANISM: Mus musculus
<220> FEATURE:
```

```
<223> OTHER INFORMATION: N-Terminal amino acid sequence

<400> SEQUENCE: 3

Met Leu Phe Met Pro Asn Leu Val Pro Pro Lys Ile Pro Asp Gly Glu
1               5                   10                  15

Arg Val Asp Phe Asp Asp Ile His Arg Lys
            20                  25

<210> SEQ ID NO 4
<211> LENGTH: 20
<212> TYPE: PRT
<213> ORGANISM: Rattus norvegicus
<220> FEATURE:
<223> OTHER INFORMATION: N-Terminal amino acid sequence

<400> SEQUENCE: 4

Met Val Pro Pro Lys Ile Pro Glu Gly Glu Lys Val Asp Phe Asp Asp
1               5                   10                  15

Ile His Arg Lys
            20

<210> SEQ ID NO 5
<211> LENGTH: 18
<212> TYPE: PRT
<213> ORGANISM: Oryctolagus cuniculus
<220> FEATURE:
<223> OTHER INFORMATION: N-Terminal amino acid sequence

<400> SEQUENCE: 5

Ala Pro Lys Ile Pro Glu Gly Glu Lys Val Asp Phe Asp Asp Ile Gln
1               5                   10                  15

Lys Lys

<210> SEQ ID NO 6
<211> LENGTH: 5
<212> TYPE: PRT
<213> ORGANISM: Mus musculus
<220> FEATURE:
<223> OTHER INFORMATION: N-Terminal amino acid sequence

<400> SEQUENCE: 6

Asp Ile Gln Lys Lys
1               5

<210> SEQ ID NO 7
<211> LENGTH: 38
<212> TYPE: PRT
<213> ORGANISM: Mus musculus
<220> FEATURE:
<223> OTHER INFORMATION: N-Terminal amino acid sequence

<400> SEQUENCE: 7

Glu Gly Pro Val Glu Asp Thr Lys Pro Lys Pro Ser Arg Leu Phe Met
1               5                   10                  15

Pro Asn Leu Val Pro Pro Lys Ile Pro Asp Gly Glu Arg Val Asp Phe
            20                  25                  30

Asp Asp Ile His Arg Lys
            35

<210> SEQ ID NO 8
<211> LENGTH: 38
<212> TYPE: PRT
<213> ORGANISM: Gallus domesticus
<220> FEATURE:
<223> OTHER INFORMATION: N-Terminal amino acid sequence
```

<400> SEQUENCE: 8

Ala Glu Glu Val His Glu Pro Ala Pro Pro Glu Glu Lys Pro Arg
1               5                   10                  15

Ile Lys Leu Thr Ala Pro Lys Ile Pro Glu Gly Glu Lys Val Asp Phe
            20                  25                  30

Asp Asp Ile Gln Lys Lys
        35

<210> SEQ ID NO 9
<211> LENGTH: 40
<212> TYPE: PRT
<213> ORGANISM: Homo sapiens
<220> FEATURE:
<223> OTHER INFORMATION: N-Terminal amino acid sequence

<400> SEQUENCE: 9

Met Ala Asp Glu Ser Ser Asp Ala Ala Gly Glu Pro Gln Pro Ala Pro
1               5                   10                  15

Ala Pro Val Arg Arg Arg Ser Ser Ala Asn Tyr Arg Ala Tyr Ala Thr
            20                  25                  30

Glu Pro His Ala Lys Lys Lys Ser
        35                  40

<210> SEQ ID NO 10
<211> LENGTH: 14
<212> TYPE: PRT
<213> ORGANISM: Homo sapiens
<220> FEATURE:
<223> OTHER INFORMATION: N-Terminal amino acid sequence

<400> SEQUENCE: 10

Tyr Arg Ala Tyr Ala Thr Glu Pro His Ala Lys Lys Lys Ser
1               5                   10

<210> SEQ ID NO 11
<211> LENGTH: 13
<212> TYPE: PRT
<213> ORGANISM: Homo sapiens
<220> FEATURE:
<223> OTHER INFORMATION: N-Terminal amino acid sequence

<400> SEQUENCE: 11

Arg Ala Tyr Ala Thr Glu Pro His Ala Lys Lys Lys Ser
1               5                   10

<210> SEQ ID NO 12
<211> LENGTH: 10
<212> TYPE: PRT
<213> ORGANISM: Homo sapiens
<220> FEATURE:
<223> OTHER INFORMATION: N-Terminal amino acid sequence

<400> SEQUENCE: 12

Ala Thr Glu Pro His Ala Lys Lys Lys Ser
1               5                   10

<210> SEQ ID NO 13
<211> LENGTH: 787
<212> TYPE: DNA
<213> ORGANISM: Homo sapiens
<220> FEATURE:
<223> OTHER INFORMATION: N-Terminal amino acid sequence

<400> SEQUENCE: 13

```
ctgaaggtca cccgggcggc cccctcactg accctccaaa cgcccctgtc ctcgccctgc      60
ctcctgccat tcccggcctg agtctcagca tggcggatgg gagcagcgat gcggctaggg     120
aacctcgccc tgcaccagcc ccaatcagac gccgctcctc aactaccgc gcttatgcca      180 cggagccgca cgccaagaaa aaatctaaga tctccgcctc gagaaaattg cagctgaaga     240
ctctgctgct gcagattgca aagcaagagc tggagcgaga ggcggaggag cggcgcggag     300
agaaggggcg cgctctgagc acccgctgcc agccgctgga gttgaccggg ctgggcttcg     360
cggagctgca ggacttgtgc cgacagctcc acgcccgtgt ggacaaggtg gatgaagaga     420
gatacgacat agaggcaaaa gtcaccaaga acatcacgga gattgcagat ctgactcaga     480
agatctttga ccttcgaggc aagtttaagc ggcccaccct gcggagagtg aggatctctg     540
cagatgccat gatgcaggcg ctgctggggg cccgggctaa ggagtccctg gacctgcggg     600
cccacctcaa gcaggtgaag aaggaggaca ccgagaagga aaaccgggag gtgggagact     660
ggcggaagaa catcgatgca ctgagtggaa tggagggccg caagaaaaag tttgagagct     720
gagccttcct gcctactgcc cctgccctga ggagggccac tgaggaataa agcttctctc     780
tgagctg                                                               787

<210> SEQ ID NO 14
<211> LENGTH: 210
<212> TYPE: PRT
<213> ORGANISM: Homo sapiens
<220> FEATURE:
<223> OTHER INFORMATION: N-Terminal amino acid sequence

<400> SEQUENCE: 14

Met Ala Asp Gly Ser Ser Asp Ala Ala Arg Glu Pro Arg Pro Ala Pro
1               5                   10                  15

Ala Pro Ile Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80

Gln Pro Leu Glu Leu Thr Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser
    210
```

<210> SEQ ID NO 15
<211> LENGTH: 1132
<212> TYPE: DNA
<213> ORGANISM: Homo sapiens
<220> FEATURE:
<223> OTHER INFORMATION: N-Terminal amino acid sequence

<400> SEQUENCE: 15

| ccccgctgag actgagcaga cgcctccagg atctgtcggc agctgctgtt ctgagggaga | 60 |
| gcagagacca tgtctgacat agaagaggtg gtggaagagt acgaggagga ggagcaggaa | 120 |
| gaagcagctg ttgaagagca ggaggaggca gcggaagagg atgctgaagc agaggctgag | 180 |
| accgaggaga ccagggcaga agaagatgaa gaagaagagg aagcaaagga ggctgaagat | 240 |
| ggcccaatgg aggagtccaa accaaagccc aggtcgttca tgcccaactt ggtgcctccc | 300 |
| aagatccccg atggagagag agtggacttt gatgacatcc accggaagcg catggagaag | 360 |
| gacctgaatg agttgcaggc gctgatcgag gctcactttg agaacaggaa gaaagaggag | 420 |
| gaggagctcg tttctctcaa agacaggatc gagagacgtc gggcagagcg ggccgagcag | 480 |
| cagcgcatcc ggaatgagcg ggagaaggag cggcagaacc gcctggctga agagagggct | 540 |
| cgacgagagg aggaggagaa caggaggaag gctgaggatg aggcccggaa gaagaaggct | 600 |
| ttgtccaaca tgatgcattt tgggggttac atccagaagc aggcccagac agagcggaaa | 660 |
| agtgggaaga ggcagactga gcgggaaaag aagaagaaga ttctggctga gaggaggaag | 720 |
| gtgctggcca ttgaccacct gaatgaagat cagctgaggg agaaggccaa ggagctgtgg | 780 |
| cagagcatct ataacttgga ggcagagaag ttcgacctgc aggagaagtt caagcagcag | 840 |
| aaatatgaga tcaatgttct ccgaaacagg atcaacgata ccagaaagt ctccaagacc | 900 |
| cgcgggaagg ctaaagtcac cgggcgctgg aaatagagcc tggcctcctt caccaaagat | 960 |
| ctgctcctcg ctcgcacctg cctccggcct gcactccccc agttcccggg ccctcctggg | 1020 |
| caccccaggc agctcctgtt tggaaatggg gagctggcct aggtgggagc caccactcct | 1080 |
| gcctgccccc acacccactc cacaccagta ataaaaagcc accacacact ga | 1132 |

<210> SEQ ID NO 16
<211> LENGTH: 288
<212> TYPE: PRT
<213> ORGANISM: Homo sapiens
<220> FEATURE:
<223> OTHER INFORMATION: N-Terminal amino acid sequence

<400> SEQUENCE: 16

Met Ser Asp Ile Glu Glu Val Val Glu Glu Tyr Glu Glu Glu Glu Gln
1               5                   10                  15

Glu Glu Ala Ala Val Glu Glu Gln Glu Glu Ala Ala Glu Glu Asp Ala
            20                  25                  30

Glu Ala Glu Ala Glu Thr Glu Glu Thr Arg Ala Glu Glu Asp Glu Glu
        35                  40                  45

Glu Glu Glu Ala Lys Glu Ala Glu Asp Gly Pro Met Glu Glu Ser Lys
    50                  55                  60

Pro Lys Pro Arg Ser Phe Met Pro Asn Leu Val Pro Pro Lys Ile Pro
65                  70                  75                  80

Asp Gly Glu Arg Val Asp Phe Asp Asp Ile His Arg Lys Arg Met Glu
                85                  90                  95

Lys Asp Leu Asn Glu Leu Gln Ala Leu Ile Glu Ala His Phe Glu Asn
            100                 105                 110

Arg Lys Lys Glu Glu Glu Glu Leu Val Ser Leu Lys Asp Arg Ile Glu

```
              115                 120                 125
Arg Arg Arg Ala Glu Arg Ala Glu Gln Gln Arg Ile Arg Asn Glu Arg
130                 135                 140

Glu Lys Glu Arg Gln Asn Arg Leu Ala Glu Glu Arg Ala Arg Arg Glu
145                 150                 155                 160

Glu Glu Glu Asn Arg Arg Lys Ala Glu Asp Glu Ala Arg Lys Lys Lys
                165                 170                 175

Ala Leu Ser Asn Met Met His Phe Gly Gly Tyr Ile Gln Lys Gln Ala
                180                 185                 190

Gln Thr Glu Arg Lys Ser Gly Lys Arg Gln Thr Glu Arg Glu Lys Lys
                195                 200                 205

Lys Lys Ile Leu Ala Glu Arg Arg Lys Val Leu Ala Ile Asp His Leu
210                 215                 220

Asn Glu Asp Gln Leu Arg Glu Lys Ala Lys Glu Leu Trp Gln Ser Ile
225                 230                 235                 240

Tyr Asn Leu Glu Ala Gly Lys Phe Asp Leu Gln Glu Lys Phe Lys Gln
                245                 250                 255

Gln Lys Tyr Glu Ile Asn Val Leu Arg Asn Arg Ile Asn Asp Asn Gln
                260                 265                 270

Lys Val Ser Lys Thr Arg Gly Lys Ala Lys Val Thr Gly Arg Trp Lys
                275                 280                 285

<210> SEQ ID NO 17
<211> LENGTH: 279
<212> TYPE: PRT
<213> ORGANISM: Oryctolagus cuniculus
<220> FEATURE:
<223> OTHER INFORMATION: N-Terminal amino acid sequence

<400> SEQUENCE: 17

Met Ser Asp Glu Glu Val Glu His Val Glu Glu Gln Tyr Glu Glu Glu
1               5                   10                  15

Glu Glu Ala Gln Glu Glu Ala Pro Ser Pro Ala Glu Val His Glu Pro
                20                  25                  30

Ala Pro Glu Val His Val Pro Glu Glu Val His Glu Asp Ala Leu Glu
                35                  40                  45

Asp Met Arg Glu Glu Glu Glu Glu Glu Lys Pro Arg Pro Lys Leu
50                  55                  60

Thr Ala Pro Lys Ile Pro Glu Gly Glu Lys Val Asp Phe Asp Asp Ile
65                  70                  75                  80

Gln Lys Lys Arg Gln Asn Lys Asp Leu Met Glu Leu Gln Ala Leu Ile
                85                  90                  95

Asp Ser His Phe Glu Ala Arg Lys Lys Glu Glu Glu Glu Leu Val Ala
                100                 105                 110

Leu Lys Glu Arg Ile Glu Lys Arg Arg Ala Glu Arg Ala Glu Gln Gln
                115                 120                 125

Arg Ile Arg Ala Glu Lys Glu Arg Glu Arg Gln Asn Arg Leu Ala Glu
                130                 135                 140

Glu Lys Ala Arg Arg Glu Glu Glu Asp Ala Lys Arg Arg Ala Glu Glu
145                 150                 155                 160

Asp Leu Lys Lys Lys Lys Ala Leu Ser Ser Met Gly Ala Asn Tyr Ser
                165                 170                 175

Ser Tyr Leu Ala Lys Ala Asp Gln Lys Arg Gly Lys Lys Gln Thr Ala
                180                 185                 190

Arg Glu Met Lys Lys Lys Ile Leu Ala Glu Arg Arg Lys Pro Leu Asn
                195                 200                 205
```

```
Ile Asp His Leu Ser Asp Glu Lys Leu Arg Asp Lys Ala Lys Glu Leu
    210                 215                 220
Trp Asp Thr Leu Tyr Gln Leu Glu Thr Asp Lys Phe Glu Phe Gly Glu
225                 230                 235                 240
Lys Leu Lys Arg Gln Lys Tyr Asp Ile Met Asn Val Arg Ala Arg Val
                245                 250                 255
Glu Met Leu Ala Lys Phe Ser Lys Ala Gly Thr Thr Ala Lys Gly
            260                 265                 270
Lys Val Gly Gly Arg Trp Lys
        275
```

<210> SEQ ID NO 18
<211> LENGTH: 1264
<212> TYPE: DNA
<213> ORGANISM: Gallus domesticus
<220> FEATURE:
<223> OTHER INFORMATION: N-Terminal amino acid sequence

<400> SEQUENCE: 18

```
gcccctctgc agggagttcc gcgcctgtct ccacaccccc aaaaactcac tgccaacatg      60
tctgataccg aggaagtgga gcacggagag gctcatgaag cagaagaggt ccacgaagaa     120
gctcatcatg aggaagctca ccatgaggaa gctcatcatg aggaagctca tcatgcggaa     180
gctcaccatg cggaagctca ccatgaagaa gctcatgctc atgcggaaga agtccatgaa     240
ccagcccccc ctccagagga gaagcccaga ataaagctaa ctgctcctaa aataccagag     300
ggtgagaaag tagattttga tgacatccaa aagaagaggc agaacaaaga cctgattgaa     360
ctgcaggcct tgattgacag ccactttgag gccaggcgaa aggaagaaga agagctggtt     420
gcccttaagg agaggattga gaaacgcaga gctgaaagag cagagcaaca gagaatccgg     480
gctgagaagg agaaggagcg tcaagcacgg cttgcggagg aaaaggcacg agagaggaa      540
gaagatgcca agagaaaagc cgaggatgat ctcaagaaga gaaggctctg tcctccatg      600
ggtgcctcat acagcagcta tctggcaaag gctgatcaga agagagggaa gaagcaaaca     660
gctagagaga caaagaagaa ggtcctggca gagaggcgca agcccttgaa cattgaccat     720
cttaatgaag acaagctgag ggacaaggct aaggaactgt gggactggtt ataccagctg     780
cagactgaga agtatgactt tgctgagcaa ataaagagga aaaatatgag gattttaaca     840
ctacgttgca ggctgcagga gctttccaag ttcagcaaga aggcaggagc caaaggcaag     900
gttggcgggc gctggaagta aagacccagg caggatggcc cttagcgatg tgccgaaacc     960
ctgctggtct cttccttctt ccttcacaaa ccacttgtgt tcccgtgcct cagtgataac    1020
taaaattgca acatcagcct gtgttggcta ttgctgctgc ttttcttctt catggagggg    1080
tctggtggct tcctcgctca aagggaagca ggttccctgt ggaactgtgg agactccttg    1140
ctggcatctt caattcctgc tgagcatgtc ctttatcctc ctgacaccag ccctatgctg    1200
tcctgtagat tgctgtgtac aaatctctgg attttgtaaa taaagcgcaa ccagtaccta    1260
cttc                                                                 1264
```

<210> SEQ ID NO 19
<211> LENGTH: 287
<212> TYPE: PRT
<213> ORGANISM: Gallus domesticus
<220> FEATURE:
<223> OTHER INFORMATION: N-Terminal amino acid sequence

<400> SEQUENCE: 19

```
Met Ser Asp Thr Glu Glu Val Glu His Gly Glu Ala His Glu Ala Glu
1               5                   10                  15

Glu Val His Glu Glu Ala His His Glu Ala His His Glu Glu Glu Ala
            20                  25                  30

His His Glu Glu Ala His His Ala Glu Ala His His Ala Glu Ala His
        35                  40                  45

His Glu Glu Ala His Ala His Ala Glu Val His Glu Pro Ala Pro
    50                  55                  60

Pro Pro Glu Glu Lys Pro Arg Ile Lys Leu Thr Ala Pro Lys Ile Pro
65              70                  75                  80

Glu Gly Glu Lys Val Asp Phe Asp Ile Gln Lys Lys Arg Gln Asn
                85                  90                  95

Lys Asp Leu Ile Glu Leu Gln Ala Leu Ile Asp Ser His Phe Glu Ala
                100                 105                 110

Arg Lys Lys Glu Glu Glu Glu Leu Val Ala Leu Lys Glu Arg Ile Glu
            115                 120                 125

Lys Arg Arg Ala Glu Arg Ala Glu Gln Gln Arg Ile Arg Ala Glu Lys
            130                 135                 140

Glu Lys Glu Arg Gln Ala Arg Leu Ala Glu Glu Lys Ala Arg Arg Glu
145                 150                 155                 160

Glu Glu Asp Ala Lys Arg Lys Ala Glu Asp Asp Leu Lys Lys Lys Lys
                165                 170                 175

Ala Leu Ser Ser Met Gly Ala Ser Tyr Ser Ser Tyr Leu Ala Lys Ala
                180                 185                 190

Asp Gln Lys Arg Gly Lys Lys Gln Thr Ala Arg Glu Thr Lys Lys Lys
            195                 200                 205

Val Leu Ala Glu Arg Arg Lys Pro Leu Asn Ile Asp His Leu Asn Glu
210                 215                 220

Asp Lys Leu Arg Asp Lys Ala Lys Glu Leu Trp Asp Trp Leu Tyr Gln
225                 230                 235                 240

Leu Gln Thr Glu Lys Tyr Asp Phe Ala Glu Gln Ile Lys Arg Lys Lys
                245                 250                 255

Tyr Glu Ile Leu Thr Leu Arg Cys Arg Leu Gln Glu Leu Ser Lys Phe
            260                 265                 270

Ser Lys Lys Ala Gly Ala Lys Gly Lys Val Gly Gly Arg Trp Lys
        275                 280                 285

<210> SEQ ID NO 20
<211> LENGTH: 996
<212> TYPE: DNA
<213> ORGANISM: Mus musculus
<220> FEATURE:
<223> OTHER INFORMATION: N-Terminal amino acid sequence

<400> SEQUENCE: 20
gcctgctgct ggtcctgtcc acaaggagcc cccagccttt ctcagactca actacagata      60
caacccaccg ccactatgtc tgacgaggaa actgaacaag ttgaggagga ggcccaagag     120
gaagaagtcc aggaggaagc ccccgaacca gaggagaaac caagacccaa acttactgct     180
cctaagatcc cggaagggga gaaagtagac tttgatgaca tccagaagaa gcgtcaaaac     240
aaggacctca tggagctcca agccctcatt gacagccact tgaagctag aaagaaagaa     300 gaagaggagc taatcgcact taagaaaga attgagaagc gccgtgcaga gagggctgag     360
cagcaaagaa ttcgcgctga aggagcgg aacgccaga acagattggc ggaggagaag     420
gccagaagag aggaggagga tgccaagagg agagctgaag atgacatgaa gaagaaaaag     480
```

```
gctctgtcct ccatgggtgc caactacagc agctacctgg ccaaggctga ccagaagaga      540
ggcaagaaac agacagcccg ggaaatgaaa aagaagattc ttgccgaaag gcgcaagcct      600
ctgaacattg accatcttag cgatgacaag ctgagggaca aggccaagga actctgggat      660
accttgtacc aactggagac tgacaaattc gagtttgggg agaagctgaa acgtcagaaa      720
tatgatatca ccaccctcag gagccgcatt gaccaaaccc agaagcacag caagaaggcc      780
ggtgccacag ccaagggcaa agtcggtggg cgctggaagt aaaagagcag agaggtgcac      840
tgcagcagag accatcaacc ctgactcctg ccagggcccc ttattccagc tctgcactct      900
ccagccttca cgcccaggca tctttgggaa ctcaggaccc accctgctgc aatgccctca      960
ccttctgggg tctaggaata aagttatcag actccg                                996
```

<210> SEQ ID NO 21
<211> LENGTH: 248
<212> TYPE: PRT
<213> ORGANISM: Mus musculus
<220> FEATURE:
<223> OTHER INFORMATION: N-Terminal amino acid sequence

<400> SEQUENCE: 21

```
Met Ser Asp Glu Glu Thr Glu Gln Val Glu Glu Ala Gln Glu
1               5                   10                  15

Glu Val Gln Glu Glu Ala Pro Glu Pro Glu Lys Pro Arg Pro Lys
            20                  25                  30

Leu Thr Ala Pro Lys Ile Pro Glu Gly Glu Lys Val Asp Phe Asp Asp
        35                  40                  45

Ile Gln Lys Lys Arg Gln Asn Lys Asp Leu Met Glu Leu Gln Ala Leu
    50                  55                  60

Ile Asp Ser His Phe Glu Ala Arg Lys Lys Glu Glu Glu Leu Ile
65                  70                  75                  80

Ala Leu Lys Glu Arg Ile Glu Lys Arg Ala Glu Arg Ala Glu Gln
                85                  90                  95

Gln Arg Ile Arg Ala Glu Lys Glu Arg Glu Arg Gln Asn Arg Leu Ala
            100                 105                 110

Glu Glu Lys Ala Arg Arg Glu Glu Glu Asp Ala Lys Arg Arg Ala Glu
        115                 120                 125

Asp Asp Met Lys Lys Lys Ala Leu Ser Ser Met Gly Ala Asn Tyr
    130                 135                 140

Ser Ser Tyr Leu Ala Lys Ala Asp Gln Lys Arg Gly Lys Lys Gln Thr
145                 150                 155                 160

Ala Arg Glu Met Lys Lys Lys Ile Leu Ala Glu Arg Arg Lys Pro Leu
                165                 170                 175

Asn Ile Asp His Leu Ser Asp Asp Lys Leu Arg Asp Lys Ala Lys Glu
            180                 185                 190

Leu Trp Asp Thr Leu Tyr Gln Leu Glu Thr Asp Lys Phe Glu Phe Gly
        195                 200                 205

Glu Lys Leu Lys Arg Gln Lys Tyr Asp Ile Thr Thr Leu Arg Ser Arg
    210                 215                 220

Ile Asp Gln Thr Gln Lys His Ser Lys Lys Ala Gly Ala Thr Ala Lys
225                 230                 235                 240

Gly Lys Val Gly Gly Arg Trp Lys
                245
```

<210> SEQ ID NO 22
<211> LENGTH: 1116
<212> TYPE: DNA

<213> ORGANISM: Rattus norvegicus
<220> FEATURE:
<223> OTHER INFORMATION: N-Terminal amino acid sequence

<400> SEQUENCE: 22

```
gcagacacct caagtcctga gtgcaggtcc ctgttcagag aacggagaac atgtctgacg    60
ccgaggaaga ggtggtggag tacgaggagg aacaggaaga gcaagaggag cagtggagg    120
aggaggatgg tgaggccgag cctgatcccg agggtgaggc agaggcagag gaggacaagg    180
cagaagaggt tggtcctgat gaagaagcca gagatgctga agatggtcca gtagaggact    240
ccaaacccaa gcccagcagg ctcttcatgc ccaacttggt gccacccaag atccctgacg    300
gagagagagt ggactttgat gacatccaca ggaagcgcat ggagaaggac ctgaacgagc    360
tgcagactct gatcgaggct cacttcgaga acaggaagaa ggaggaagag gagctcattt    420
ctctcaaaga caggatcgaa aagcgtcggg cagagcgggc tgaacagcag cgtattcgca    480
atgaacgaga gaaggaaagg cagaaccgcc tggctgaaga gagggcccgg cgtgaggagg    540
aggagaacag gaggaaggct gaagatgagg cccggaagaa gaaggctctg tccaacatga    600
tgcattttgg agggtacatc cagaaggctc agacagagcg gaagagtggg aagagacaga    660
cagagcgaga gaagaagaag aagattctgg cagagaggag gaaggtgctg gccatcgacc    720
acctgaatga agaccagctg agagagaagg ccaaggagct atggcagagt atccacaacc    780
tagaggccga gaagttcgac ctgcaggaaa agttcaagca gcagaaatat gaaatcaacg    840
ttctgcgaaa caggatcaac gacaaccaga agtctccaa aactcgtggg aaggccaaag    900
tcaccgggcg ttggaaatag atggaactgt gttcgacaaa gctctgttcc ttgcctgtgc    960
ccttgccctg tgaatcccag ctctaggtct tgccaggcac ccgatgcaga ctcctgtctg   1020
gaaagtagga gctgacctag ctagaagcca gtactctgcc tgaccccctat gcccacacca   1080
cgtcaggaat aaaaagccag cacattgtgc acatgg                              1116
```

<210> SEQ ID NO 23
<211> LENGTH: 289
<212> TYPE: PRT
<213> ORGANISM: Rattus norvegicus
<220> FEATURE:
<223> OTHER INFORMATION: N-Terminal amino acid sequence

<400> SEQUENCE: 23

```
Met Ser Asp Ala Glu Glu Val Val Glu Tyr Glu Glu Glu Gln Glu
1               5                   10                  15

Glu Gln Glu Glu Ala Val Glu Glu Asp Gly Glu Ala Glu Pro Asp
            20                  25                  30

Pro Glu Gly Glu Ala Glu Ala Glu Asp Lys Ala Glu Glu Val Gly
        35                  40                  45

Pro Asp Glu Glu Ala Arg Asp Ala Glu Asp Gly Pro Val Glu Asp Ser
    50                  55                  60

Lys Pro Lys Pro Ser Arg Leu Phe Met Pro Asn Leu Val Pro Pro Lys
65                  70                  75                  80

Ile Pro Asp Gly Glu Arg Val Asp Phe Asp Asp Ile His Arg Lys Arg
                85                  90                  95

Met Glu Lys Asp Leu Asn Glu Leu Gln Thr Leu Ile Glu Ala His Phe
            100                 105                 110

Glu Asn Arg Lys Lys Glu Glu Glu Glu Leu Ile Ser Leu Lys Asp Arg
        115                 120                 125

Ile Glu Lys Arg Arg Ala Glu Arg Ala Glu Gln Gln Arg Ile Arg Asn
    130                 135                 140
```

```
Glu Arg Glu Lys Glu Arg Gln Asn Arg Leu Ala Glu Arg Ala Arg
145                 150                 155                 160

Arg Glu Glu Glu Glu Asn Arg Arg Lys Ala Glu Asp Glu Ala Arg Lys
            165                 170                 175

Lys Lys Ala Leu Ser Asn Met Met His Phe Gly Gly Tyr Ile Gln Lys
        180                 185                 190

Ala Gln Thr Glu Arg Lys Ser Gly Lys Arg Gln Thr Glu Arg Glu Lys
        195                 200                 205

Lys Lys Lys Ile Leu Ala Glu Arg Arg Lys Val Leu Ala Ile Asp His
        210                 215                 220

Leu Asn Glu Asp Gln Leu Arg Glu Lys Ala Lys Glu Leu Trp Gln Ser
225                 230                 235                 240

Ile His Asn Leu Glu Ala Glu Lys Phe Asp Leu Gln Glu Lys Phe Lys
                245                 250                 255

Gln Gln Lys Tyr Glu Ile Asn Val Leu Arg Asn Arg Ile Asn Asp Asn
            260                 265                 270

Gln Lys Val Ser Lys Thr Arg Gly Lys Ala Lys Val Thr Gly Arg Trp
        275                 280                 285

Lys

<210> SEQ ID NO 24
<211> LENGTH: 830
<212> TYPE: DNA
<213> ORGANISM: Rattus norvegicus
<220> FEATURE:
<223> OTHER INFORMATION: N-Terminal amino acid sequence

<400> SEQUENCE: 24
cgcttgagca gcacagaggg gacccaaccc tccaaggtca ccaggacaca ccttctaaga      60
ccctccagga atctgcaatc ccattctcta cctctggaga tcagcatggc ggatgagagc     120
agcgatgcgg ctggggaacc ccagccggcg cctgctcctg tccgacgtcg ctcctcggcc     180
aactaccgag cctatgccac cgagccacat gccaagaaaa agtctaagat ctccgcctcc     240
agaaaacttc agttgaagac tctgatgctg cagattgcga agcaggagat ggagcgtgag     300
gcagaggagc gacgtggaga aagggccgc gttctgagca cgcgttgcca gcccttggtg     360
ttggatgggc tgggctttga agagcttcag gacctatgcc ggcagcttca cgctcgtgtg     420
gacaaagtgg atgaagagag atacgacgtg gaagcaaaag tcaccaagaa catcactgag     480
attgcagatc tgacccagaa gatctatgac ctgcgtggca gtttaagcg cccactctc      540 cgaagagtga gaatctcagc agatgccatg atgcaggcac tactggggac ccgggccaag     600
gaatccttgg acctgagggc ccacctcaag caggtgaaga aggaggacat tgagaaggaa     660
aaccgggagg tgggagactg gcgcaagaat atcgatgcac taagtggaat ggaaggccga     720
aagaaaaagt ttgagggctg agcccatggc tctcacactg tgctctgaag gcatctctg     780 aggaataaat ttctttaaac tggaaaaaaa aaaaaaaaa aaaaaaaaa                 830

<210> SEQ ID NO 25
<211> LENGTH: 211
<212> TYPE: PRT
<213> ORGANISM: Rattus norvegicus
<220> FEATURE:
<223> OTHER INFORMATION: N-Terminal amino acid sequence

<400> SEQUENCE: 25

Met Ala Asp Glu Ser Ser Asp Ala Ala Gly Glu Pro Gln Pro Ala Pro
1               5                   10                  15
```

```
Ala Pro Val Arg Arg Ser Ser Ala Asn Tyr Arg Ala Tyr Ala Thr
            20                  25                  30
Glu Pro His Ala Lys Lys Ser Lys Ile Ser Ala Ser Arg Lys Leu
        35                  40                  45
Gln Leu Lys Thr Leu Met Leu Gln Ile Ala Lys Gln Glu Met Glu Arg
    50                  55                  60
Glu Ala Glu Arg Arg Gly Glu Lys Gly Arg Val Leu Ser Thr Arg
65                  70                  75                  80
Cys Gln Pro Leu Val Leu Asp Gly Leu Gly Phe Glu Glu Leu Gln Asp
                85                  90                  95
Leu Cys Arg Gln Leu His Ala Arg Val Asp Lys Val Asp Glu Arg
            100                 105                 110
Tyr Asp Val Glu Ala Lys Val Thr Lys Asn Ile Thr Glu Ile Ala Asp
            115                 120                 125
Leu Thr Gln Lys Ile Tyr Asp Leu Arg Gly Lys Phe Lys Arg Pro Thr
    130                 135                 140
Leu Arg Arg Val Arg Ile Ser Ala Asp Ala Met Met Gln Ala Leu Leu
145                 150                 155                 160
Gly Thr Arg Ala Lys Glu Ser Leu Asp Leu Arg Ala His Leu Lys Gln
                165                 170                 175
Val Lys Lys Glu Asp Ile Glu Lys Glu Asn Arg Glu Val Gly Asp Trp
            180                 185                 190
Arg Lys Asn Ile Asp Ala Leu Ser Gly Met Glu Gly Arg Lys Lys Lys
            195                 200                 205
Phe Glu Gly
    210

<210> SEQ ID NO 26
<211> LENGTH: 1112
<212> TYPE: DNA
<213> ORGANISM: Mus musculus
<220> FEATURE:
<223> OTHER INFORMATION: N-Terminal amino acid sequence

<400> SEQUENCE: 26
tacctcaaga cctgtgtgca gtccctgttc agagggagag ccgagagcat gtctgacgcc      60
gaggaggtgg tggaggagta cgaggaggaa caggaagagc aagaggaggc agtggaggag     120
gaggaggctg gtggggctga acctgagcct gagggtgagg ctgagacaga ggaggccaac     180
gtagaagagg ttggtcctga tgaagaagcc aaagatgctg aagaaggtcc agtagaggac     240
accaaaccca gcccagcag gctcttcatg cccaacttgg tgccacccaa gatccccgat     300
ggagagagag tggactttga tgacatccac aggaagcgcg tggagaagga cctgaatgag     360
ctacagactc tgatcgaggc tcacttcgag aacaggaaga aggaggaaga ggagctgatt     420
tccctcaaag acaggatcga aaagcgtcgg gcagagcggg ccgagcagca gcgtattcgc     480
aatgagcggg agaaggaaag gcagaaccgc ctggctgaag agagggcccg cgtgaggag      540
gaggagaaca ggaggaaggc tgaggatgag gcccggaaga agaaggctct gtccaacatg     600
atgcactttg gagggtacat ccagaagcaa gctcagacag agcggaagag tgggaagaga     660
cagacagaga gagagaagaa gaagaagatc ctggcagaga ggaggaaggc gctggccatc     720
gaccacctga tgaagaccca actgagagag aaggccaagg agctgtggca gagtattcac     780
aacctggagg ctgagaagtt cgacctgcag gaaaagttca gcagcagaa atacgaaatc     840
aacgttctgc gaaaccggat caatgacaac cagaaagtct ccaaaactcg tgggaaggcc     900
```

-continued

```
aaagtcaccg  ggcgttggaa  atagatgaaa  ctgttctcgt  caaagctgtg  cccctgctt      960 gtgtccttgc  cccgtgcatc  ccagctctgg  gtcctccttg  gcacccaatg  cagactcctg    1020
tttggatagt  gggagctggc  ttagctagaa  gccagtactc  tgcctgaccc  ctatgcccgc    1080
actatgccag  caataaaaag  ccaacacact  gc                                    1112
```

<210> SEQ ID NO 27
<211> LENGTH: 291
<212> TYPE: PRT
<213> ORGANISM: Mus musculus
<220> FEATURE:
<223> OTHER INFORMATION: N-Terminal amino acid sequence

<400> SEQUENCE: 27

```
Met Ser Asp Ala Glu Val Val Glu Tyr Glu Glu Gln Glu
1               5                   10                  15

Glu Gln Glu Glu Ala Val Glu Glu Glu Ala Gly Gly Ala Glu Pro
                20                  25                  30

Glu Pro Glu Gly Glu Ala Glu Thr Glu Glu Ala Asn Val Glu Val
            35                  40                  45

Gly Pro Asp Glu Glu Ala Lys Asp Ala Glu Gly Pro Val Glu Asp
        50                  55                  60

Thr Lys Pro Lys Pro Ser Arg Leu Phe Met Pro Asn Leu Val Pro Pro
65                  70                  75                  80

Lys Ile Pro Asp Gly Glu Arg Val Asp Phe Asp Asp Ile His Arg Lys
                85                  90                  95

Arg Val Glu Lys Asp Leu Asn Glu Leu Gln Thr Leu Ile Glu Ala His
                100                 105                 110

Phe Glu Asn Arg Lys Lys Glu Glu Glu Glu Leu Ile Ser Leu Lys Asp
            115                 120                 125

Arg Ile Glu Lys Arg Arg Ala Glu Arg Ala Glu Gln Gln Arg Ile Arg
        130                 135                 140

Asn Glu Arg Glu Lys Glu Arg Gln Asn Arg Leu Ala Glu Glu Arg Ala
145                 150                 155                 160

Arg Arg Glu Glu Glu Glu Asn Arg Arg Lys Ala Glu Asp Glu Ala Arg
                165                 170                 175

Lys Lys Lys Ala Leu Ser Asn Met Met His Phe Gly Gly Tyr Ile Gln
            180                 185                 190

Lys Gln Ala Gln Thr Glu Arg Lys Ser Gly Lys Arg Gln Thr Glu Arg
        195                 200                 205

Glu Lys Lys Lys Lys Ile Leu Ala Glu Arg Arg Lys Ala Leu Ala Ile
    210                 215                 220

Asp His Leu Asn Glu Asp Gln Leu Arg Glu Lys Ala Lys Glu Leu Trp
225                 230                 235                 240

Gln Ser Ile His Asn Leu Glu Ala Glu Lys Phe Asp Leu Gln Glu Lys
                245                 250                 255

Phe Lys Gln Gln Lys Tyr Glu Ile Asn Val Leu Arg Asn Arg Ile Asn
            260                 265                 270

Asp Asn Gln Lys Val Ser Lys Thr Arg Gly Lys Ala Lys Val Thr Gly
        275                 280                 285

Arg Trp Lys
    290
```

<210> SEQ ID NO 28
<211> LENGTH: 636
<212> TYPE: DNA
<213> ORGANISM: Mus musculus
<220> FEATURE:
<223> OTHER INFORMATION: N-Terminal amino acid sequence

<400> SEQUENCE: 28

```
atggctgatg aaagcagcga tgcggctggg gaaccgcagc ctgcgcctgc tcctgtccga      60
cgccgctcct ctgccaacta ccgagcctat gccaccgagc cacacgccaa gaaaaagtct     120
aagatctccg cctccagaaa acttcagttg aagactctga tgctgcagat tgcgaagcag     180
gagatggaac gagaggcaga agagcgacgt ggagagaagg ggcgcgttct gaggactcgt     240
tgccagcctt tggagttgga tgggctgggc tttgaagagc ttcaggactt atgccgacag     300
cttcacgctc gggtggacaa agtggatgaa gagagatatg acgtggaagc aaaagtcacc     360
aagaacatca ctgagattgc agatctgacc cagaagatct atgacctccg tggcaagttt     420
aagcggccca ccctccgaag agtgaggatc tctgcagatg ccatgatgca ggcgctgctg     480
gggacccggg ccaaggaatc cttggacctg agggcccacc tcaagcaggt gaagaaggag     540
gacattgaga aggaaaaccg ggaggtggga gactggcgca agaatatcga tgcactgagt     600
ggcatggaag ccgcaagaa aaagtttgag ggctga                                636
```

<210> SEQ ID NO 29

<211> LENGTH: 211
<212> TYPE: PRT
<213> ORGANISM: Mus musculus
<220> FEATURE:
<223> OTHER INFORMATION: N-Terminal amino acid sequence

<400> SEQUENCE: 29

```
Met Ala Asp Glu Ser Ser Asp Ala Ala Gly Glu Pro Gln Pro Ala Pro
1               5                   10                  15

Ala Pro Val Arg Arg Ser Ser Ala Asn Tyr Arg Ala Tyr Ala Thr
            20                  25                  30

Glu Pro His Ala Lys Lys Lys Ser Lys Ile Ser Ala Ser Arg Lys Leu
        35                  40                  45

Gln Leu Lys Thr Leu Met Leu Gln Ile Ala Lys Gln Glu Met Glu Arg
    50                  55                  60

Glu Ala Glu Glu Arg Arg Gly Glu Lys Gly Arg Val Leu Arg Thr Arg
65                  70                  75                  80

Cys Gln Pro Leu Glu Leu Asp Gly Leu Gly Phe Glu Glu Leu Gln Asp
                85                  90                  95

Leu Cys Arg Gln Leu His Ala Arg Val Asp Lys Val Asp Glu Glu Arg
            100                 105                 110

Tyr Asp Val Glu Ala Lys Val Thr Lys Asn Ile Thr Glu Ile Ala Asp
        115                 120                 125

Leu Thr Gln Lys Ile Tyr Asp Leu Arg Gly Lys Phe Lys Arg Pro Thr
    130                 135                 140

Leu Arg Arg Val Arg Ile Ser Ala Asp Ala Met Met Gln Ala Leu Leu
145                 150                 155                 160

Gly Thr Arg Ala Lys Glu Ser Leu Asp Leu Arg Ala His Leu Lys Gln
                165                 170                 175

Val Lys Lys Glu Asp Ile Glu Lys Glu Asn Arg Glu Val Gly Asp Trp
            180                 185                 190

Arg Lys Asn Ile Asp Ala Leu Ser Gly Met Glu Gly Arg Lys Lys Lys
        195                 200                 205

Phe Glu Gly
    210
```